US012797485B2

(12) United States Patent
Asokan et al.

(10) Patent No.: US 12,797,485 B2
(45) Date of Patent: Nov. 17, 2026

(54) COMPOSITIONS AND METHODS FOR EVADING HUMORAL IMMUNITY

(71) Applicant: Duke University, Durham, NC (US)

(72) Inventors: Aravind Asokan, Durham, NC (US); Zachary Elmore, Durham, NC (US)

(73) Assignee: Duke University, Durham, NC (US)

( * ) Notice: Subject to any disclaimer, the term of this patent is extended or adjusted under 35 U.S.C. 154(b) by 1027 days.

(21) Appl. No.: 17/425,765

(22) PCT Filed: Jan. 28, 2020

(86) PCT No.: PCT/US2020/015386
§ 371 (c)(1),
(2) Date: Jul. 26, 2021

(87) PCT Pub. No.: WO2020/159970
PCT Pub. Date: Aug. 6, 2020

(65) Prior Publication Data

US 2022/0143213 A1 May 12, 2022

Related U.S. Application Data

(60) Provisional application No. 62/914,682, filed on Oct. 14, 2019, provisional application No. 62/797,495, filed on Jan. 28, 2019.

(51) Int. Cl.
*A61K 48/00* (2006.01)
*C12N 9/64* (2006.01)
*C12N 15/86* (2006.01)

(52) U.S. Cl.
CPC .......... *A61K 48/005* (2013.01); *C12N 9/6472* (2013.01); *C12N 15/86* (2013.01); *C12N 2750/14143* (2013.01)

(58) Field of Classification Search
None
See application file for complete search history.

(56) References Cited

U.S. PATENT DOCUMENTS

| | | | |
|---|---|---|---|
| 2009/0317417 A1 | 12/2009 | Vandenberghe et al. | |
| 2021/0228738 A1* | 7/2021 | Lacroix-Desmazes | C12N 9/24 |

FOREIGN PATENT DOCUMENTS

| | | | |
|---|---|---|---|
| CA | 3106368 | A1 | 1/2020 |
| CN | 107532158 | | 1/2018 |
| JP | 2018510622 | A | 4/2018 |
| WO | 0028004 | A1 | 5/2000 |
| WO | 2016/128559 | | 8/2016 |
| WO | 2017058892 | A2 | 4/2017 |
| WO | 2019028306 | A2 | 2/2019 |
| WO | 2019195423 | A1 | 10/2019 |
| WO | 2019195444 | A1 | 10/2019 |
| WO | 2019195449 | A1 | 10/2019 |
| WO | 2020/016318 | | 1/2020 |

OTHER PUBLICATIONS

Longping V Tse et al., "Strategies to circumvent humoral immunity to adeno-associated viral vectors", Expert Opinion on Biological Therapy, May 19, 2015, pp. 845-855, vol. 15, No. 6.
Vedell Louis Jeune et al., "Pre-existing Anti-Adeno-Associated Virus Antibodies as a Challenge in AAV Gene Therapy", Human Gene Therapy Methods, Apr. 1, 2013, pp. 59-67, vol. 24, No. 2.
Anna Majowicz et al., "Successful Repeated Hepatic Gene Delivery in Mice and Non-human Primates Achieved by Sequential Administration of AAV5 ch and AAV1", Molecular Therapy, Aug. 1, 2017, pp. 1831-1842, vol. 25, No. 8.
Winstedt Lena et al., "Complete Removal of Extracellular IgG Antibodies in a Randomized Dose-Escalation Phase I Study with the Bacterial Enzyme IdeS—A Novel Therapeutic Opportunity", PLOS ONE, Jul. 15, 2015, p. e0132011, vol. 10, No. 7.
Nandakumar et al., "Therapeutic cleavage of IgG: new avenues for treating inflammation", Trends in Immunology, Elsevier Ltd. Trends Journals, Mar. 6, 2008, pp. 173-178, vol. 29, No. 4.
Randall J. Brezski et al., "Cleavage of IgGs by proteases associated with invasive diseases", Landes Bioscience, May 1, 2010, pp. 212-220, vol. 2, No. 3.
Extended European Search Report mailed Aug. 18, 2022 for EP Application No. 20749331.3 (Applicant—Duke University // Inventors—Aravind Asokan et al.) (12 pages).
Dimattia M.A., et al., "Structural Insight into the Unique Properties of Adeno-Associated Virus Serotype 9," Journal of Virology, Jun. 2012, vol. 86, No. 12, pp. 6947-6958.
Elmore Z.C., et al., "Rescuing AAV Gene Transfer from Neutralizing Antibodies with an IgG-Degrading Enzyme," JCI Insight, Oct. 2, 2020, vol. 5, No. 19, 12 pages.
First Office Action and Search Report for Chinese Patent Application No. 2020800197668, dated Dec. 1, 2023, 13 pages.
Gao G., et al., "Clades of Adeno-Associated Viruses Are Widely Disseminated in Human Tissues," Journal of Virology, Jun. 2004, vol. 78, No. 12, pp. 6381-6388.
Govindasamy L., et al., "Structural Insights into Adeno-Associated Virus Serotype 5," Journal of Virology, Oct. 2013, vol. 87, No. 20, pp. 11187-11199.
Govindasamy L., et al., "Structurally Mapping the Diverse Phenotype of Adeno-Associated Virus Serotype 4," Journal of Virology, Dec. 2006, vol. 80, No. 23, pp. 11556-11570.
Hauck B., et al., "Characterization of Tissue Tropism Determinants of Adeno-Associated Virus Type 1," Journal of Virology, Feb. 2003, vol. 77, No. 4, pp. 2768-2774.
Kailasan S., et al., "Structure of an Enteric Pathogen, Bovine Parvovirus," Journal of Virology, Mar. 2015, vol. 89, No. 5, pp. 2603-2614.
Lerch T.F., et al., "The Structure of Adeno-Associated Virus Serotype 3B (AAV-3B): Insights into Receptor Binding and Immune Evasion," Virology, Jul. 20, 2010, vol. 403, No. 1, pp. 26-36.

(Continued)

*Primary Examiner* — Robert J Yamasaki
*Assistant Examiner* — Charles Zoltan Constantine
(74) *Attorney, Agent, or Firm* — Polsinelli PC

(57) ABSTRACT

The present disclosure provides, in part, compositions and methods for transient removal of neutralizing antibodies directed to AAV vectors. Such compositions and methods expand the patient cohort eligible for gene therapy and also for redosing/re-administration of AAV in patients previously treated with AAV vectors.

16 Claims, 18 Drawing Sheets

Specification includes a Sequence Listing.

(56) References Cited

OTHER PUBLICATIONS

Mcleod B., et al., "Characterization of IdeZ Protease," New England Biolabs Poster, Jan. 2016, 2 pages.
Mori S., et al., "Two Novel Adeno-Associated Viruses from Cynomolgus Monkey: Pseudotyping Characterization of Capsid Protein," Virology, Dec. 20, 2004, vol. 330, No. 2, pp. 375-383.
Nam H.J., et al., "Structure of Adeno-Associated Virus Serotype 8, a Gene Therapy Vector," Journal of Virology, Nov. 2007, vol. 81, No. 22, pp. 12260-12271.
Ng R., et al., "Structural Characterization of the Dual Glycan Binding Adeno-Associated Virus Serotype 6," Journal of Virology, Dec. 2010, vol. 84, No. 24, pp. 12945-12957.
Office Action for Canadian Application No. 3,127,950, mailed on Feb. 13, 2024, 7 pages.
Office Action for Japanese Patent Application No. 2021-543205, mailed on Jan. 30, 2024, 6 pages.
Tsao J., et al., "The Three-Dimensional Structure of Canine Parvovirus and Its Functional Implications," Science, Mar. 22, 1991, vol. 251, No. 5000, pp. 1456-1464.
Wang L., et al., "Expanding the Genetic Code," Angewandte Chemie International Edition, 2005, vol. 44, No. 1, pp. 34-66.
Wang L., et al., "Expanding the Genetic Code," Annual Review of Biophysics and Biomolecular Structure, 2006, vol. 35, pp. 225-249.
Wang L., et al., "Expanding the Genetic Code," Chemical Communication, 2002, vol. 1, pp. 1-11.
Xie Q., et al., "Canine Parvovirus Capsid Structure, Analyzed at 2.9 A Resolution," Journal of Molecular Biology, Dec. 6, 1996, vol. 264, No. 3, pp. 497-520.
Xie Q., et al., "The Atomic Structure of Adeno-Associated Virus (AAV-2), a Vector for Human Gene Therapy," Proceedings of the National Academy of Sciences of the United States of America, Aug. 6, 2002, vol. 99, No. 16, pp. 10405-10410.
Foster MH, et al. (2019) Emerging immunotherapies for autoimmune kidney disease. Hum Vaccin Immunother. 15(4):876-890.
International Search Report mailed Apr. 27, 2020 for PCT/US2020/015386 (f/d Jan. 28, 2020) (Applicant—Duke University) (4 pages).
Written Opinion mailed Apr. 27, 2020 for PCT/US2020/015386 (f/d Jan. 28, 2020) (Applicant—Duke University) (9 pages).
NCBI Ref. No. WP_012515503.1 for IgG-degrading enzyme/Mac-1 IdeZ (1 page).

* cited by examiner

COMPOSITIONS AND METHODS FOR EVADING HUMORAL IMMUNITY

CROSS REFERENCE TO RELATED APPLICATIONS

This application is a national phase application of International Application No. PCT/US2020/015386 filed Jan. 28, 2020, which claims priority to U.S. Provisional Patent Application Ser. No. 62/797,495, filed Jan. 28, 2019, and to U.S. Provisional Patent Application Ser. No. 62/914,682, filed Oct. 14, 2019, the contents of each of which are hereby incorporated by reference in their entirety.

STATEMENT REGARDING FEDERALLY SPONSORED RESEARCH OR DEVELOPMENT

This invention was made with government support under R01 HL089221, and R01 GM127708 awarded by the National Institutes of Health. The government has certain rights in the invention.

DESCRIPTION OF THE TEXT FILE SUBMITTED ELECTRONICALLY

The contents of the text file submitted electronically herewith are incorporated by reference in their entirety: a computer readable format copy of the Sequence Listing (filename: STRD_014_02WO_SeqList_ST25.txt, date recorded Jan. 28, 2020, file size ~180 kilobytes).

TECHNICAL FIELD

This application is generally related to the fields of gene therapy, for example, gene therapy using adeno-associated virus (AAV) vectors. More specifically, the disclosure is related to compositions and methods for improving the effectiveness of a treatment with a recombinant AAV using compositions and methods that reduce neutralizing antibodies against the recombinant AAV.

BACKGROUND

Adeno-associated viruses (AAVs) are helper-dependent parvoviruses that may be used for therapeutic gene delivery in humans. Since the regulatory approval of the first AAV1-based gene therapy in 2012, encouraging results from clinical trials involving recombinant AAV vectors for gene therapy in Leber congenital amaurosis, hemophilia, and other diseases have been reported.

Although they use different natural AAV isolates, these gene therapy trials share the same exclusion criteria, requiring low or undetectable anti-AAV neutralizing antibody (NAb) titers in prospective patients seeking to enroll. This eligibility criterion was established owing to the high prevalence of pre-existing anti-AAV NAbs in the human population arising from natural exposure; for instance, the overall prevalence of human subjects with cardiac failure positive for anti-AAV1 NAbs at titers >1:2 is ~60%. Furthermore, most patients with high NAb titers against AAV serotype 2 also have measurable titers to AAV1, suggesting cross-reactivity between serotypes. NAbs can substantially reduce gene transfer efficiency of AAV vectors by opsonization, which then accelerates clearance, alters biodistribution, blocks cell surface receptor binding, and/or adversely impacts the post-attachment steps essential for efficient transduction.

Efforts to develop strategies to overcome pre-existing anti-AAV Nabs have focused on AAV capsid engineering and decoys, transient pharmacological immunomodulation, and plasmapheresis. These approaches have demonstrated limited potential for enhancing AAV gene transfer by circumventing or reducing the pre-existing NAbs in preclinical animal models and in humans.

Thus, there is a need in the art for compositions and methods for reducing, eliminating, or inactivating pre-existing anti-AAV NAbs and the generation of antibodies against AAV vectors after administration thereof to a subject in order to improve the effectiveness of gene delivery using AAV vectors.

SUMMARY

Provided herein are compositions and methods for reducing, in a subject in need thereof, the amount of one or more neutralizing antibodies against a recombinant adeno-associated virus (AAV) vector. The compositions and methods described herein may improve the effectiveness of gene delivery, for example by increasing the circulation time and/or infectivity of AAV in a subject. The compositions and methods described herein may also allow for the re-dosing of a subject with a therapeutic AAV, wherein the subject has previously been administered a therapeutic AAV. In some embodiments, a wildtype or mutant form of an antibody-degrading enzyme such as IdeZ (or a fragment thereof) is administered to reduce NAbs in a subject in need thereof.

In some embodiments, the disclosure provides a method for reducing, in a subject in need thereof, the amount of a neutralizing antibody against a recombinant adeno-associated virus (AAV) vector, the method comprising administering to the subject an effective amount of a composition that promotes the degradation of the neutralizing antibody.

Also provided is a method for preparing a subject in need thereof for treatment with a recombinant adeno-associated virus (AAV) vector, the method comprising administering to the subject an effective amount of a composition that (a) promotes the degradation of a neutralizing antibody against the AAV vector, and/or (b) reduces the binding of the neutralizing antibody to an Fc receptor.

Also provided is a method for treating a subject in need thereof with a recombinant adeno-associated virus (AAV) vector, the method comprising: (i) administering to the subject an effective amount of a composition that (a) promotes the degradation of a neutralizing antibody against the AAV vector, and/or (b) reduces the binding of the neutralizing antibody to an Fc receptor; and (ii) administering to the subject an effective amount of the AAV vector.

Also provided is a method for treating a subject in need thereof with a second recombinant adeno-associated virus (AAV) vector, wherein the subject has previously been treated with a first recombinant AAV, the method comprising: (i) administering to the subject an effective amount of a composition that (a) promotes the degradation of a neutralizing antibody against the first and/or the second recombinant AAV vector, and/or (b) reduces the binding of the neutralizing antibody to an Fc receptor; and (ii) administering to the subject an effective amount of the second recombinant AAV vector.

Also provided is a method for reducing neutralizing antibodies against an adeno-associated virus (AAV) vector comprising a heterologous nucleic acid in a subject in need thereof, comprising administering to the subject an effective amount of the AAV vector, and a composition that (a) promotes the degradation of an antibody against the AAV vector, or a recombinant protein encoded by the heterologous nucleic acid; and/or (b) reduces the binding of the antibody to an Fc receptor.

The compositions described herein may comprise, for example, an antibody-degrading enzyme or a fragment thereof. In some embodiments, the compositions comprise a vector comprising a polynucleotide encoding an antibody-degrading enzyme or fragment thereof. In some embodiments, the antibody-degrading enzyme or fragment thereof has cysteine protease activity. In some embodiments, the antibody-degrading enzyme specifically cleaves IgG. In some embodiments, the antibody-degrading enzyme has at least 90%, at least 95%, at least 96%, at least 97%, at least 98%, at least 99%, or 100% sequence identity to the amino acid sequence of SEQ ID NO: 1.

These and other embodiments will be described in more detail below.

BRIEF DESCRIPTION OF THE DRAWINGS

FIG. 1A provides a map of a GST-IdeZ expression vector. Using this vector, recombinant GST-IdeZ was expressed in *E. coli* and purified using glutathione sepharose. FIG. 1B provides an image of a gel used to visualize purified GST-IdeZ.

FIG. 2B provides an image of a similarly stained SDS-PAGE gel showing banding patterns of mouse serum, primate serum, and human serum samples that were either untreated (−) or treated (+) with rIdeZ. In FIGS. 2A and 2B, * indicate IgG heavy chain cleavage product (~31 kDa). FIG. 2C shows the result of a similar experiment wherein recombinant IdeZ was shown to cleave serum IgG from dogs, and FIG. 2D shows IdeZ cleavage of serum IgG from human patients.

FIG. 3A provides an image of a Western Blot showing that IdeZ cleaves human IVIG in vivo in mice. * indicate cleavage products. FIG. 3B provides an image of a Coomassie stained SDS-PAGE gel showing banding patterns after human IVIG samples were treated with IdeZ in vitro.

FIG. 5 depicts a crystal structure for the IdeZ protein. Each panel displays a different view.

In FIG. 6, the indicated serum samples were untreated (−) or treated (+) with recombinant GST-IdeZ (1 μg) for 3 hours at 37° C. The reactions were diluted 1:10 and analyzed by SDS-PAGE under reducing conditions. Gels were then stained with Coomassie blue. * indicate IgG heavy chain cleavage product (~31 kDa).

FIG. 7 shows the results of an experiment wherein mice were injected intraperitoneally with 8 mg of human IVIG. The same mice were injected intravenously 24 hours later with PBS (−) or recombinant GST-IdeZ (2.5 mg/kg) (+). Blood samples were taken prior to IVIG injection, and 24 hours, 48 hours, and 72 hours post IVIG injection. Blood samples were analyzed by SDS-PAGE and western blotting. IVIG was probed with goat anti-human IgG conjugated to HRP secondary (1:10,000). Each lane represents a blood sample from an individual mouse.

FIG. 8A-8B show the results of an experiment wherein mice were injected intraperitoneally with 8 mg of human IVIG. The same mice were injected intravenously 24 hours later with PBS (−) (FIG. 8A, left panel) or recombinant GST-IdeZ at a dose of 0.25 mg/kg (FIG. 8A, right panel), 1 mg/kg (FIG. 8B, left panel) or 2.5 mg/kg (FIG. 8B, right panel) (+). Blood samples were taken 72 hours post IVIG injection and analyzed by SDS-PAGE and western blotting. IVIG was probed with goat anti-human IgG conjugated to HRP secondary (1:10,000). Each lane represents a blood sample from an individual mouse.

FIG. 9 shows the results of an experiment wherein mice were injected intraperitoneally with 8 mg of human IVIG. The same mice were injected intravenously 24 hours later with PBS (−) or recombinant GST-IdeZ (1 mg/kg) (+). Blood samples were taken 72 hours post IVIG injection and analyzed by SDS-PAGE and western blotting. IVIG was probed with goat ant-human IgG conjugated to HRP secondary (1:10,000) or goat anti-human IgG Fc conjugated to HRP secondary (1:10,000).

FIG. 10 provides a neutralization profile of AAV8-Luc with human IVIG. Human IVIG samples were either left untreated, or treated with GST-IdeZ (1 μg), and were serially diluted in two-fold increments from 1:1000 to 1:102,400. Subsequently, the samples were co-incubated with AAV8-Luc in vitro (100,000 vg/cell). Solid lines represent relative transduction efficiencies of AAV8-Luc treated with IVIG and AAV8-Luc treated with IVIG preincubated with GST-IdeZ in different dilutions of IVIG. Error bars represent SEM (n=3).

FIG. 11 shows liver copy number of AAV8-Luc in mice. Each bar represents a different mouse. The first 8 bars represent mice injected with AAV8 only (PBS-PBS-AAV8). The next 6 bars represent mice injected with recombinant IdeZ and AAV8-Luc (PBS-IdeZ-AAV8). The following 6 bars represent mice injected with IVIG, and subsequently injected with AAV8-Luc (IVIG-PBS-AAV8). The final 8 bars represent mice injected with IVIG, and subsequently injected with both IdeZ and AAV8-Luc (IVIG-IdeZ-AA8). Vector genome copy numbers per cell were calculated.

FIG. 13A-13B shows percent transduction in liver (FIG. 13A) and heart (FIG. 13B). Serum samples were obtained from 18 human patients. 100 μl of each human patient serum sample was injected intraperitoneally into two different mice. Mice were then injected intravenously 72 hours later with PBS or recombinant GST-IdeZ (2.5 mg/kg). Mice were subsequently injected intravenously 72 hrs post-IdeZ treatment with AAV9-Luc ($2\times10^{11}$ vg/mouse). Liver and heart transduction levels were analyzed 4 weeks post-injection. Transduction levels were normalized to control mice that were injected with AAV9-Luc ($2\times10^{11}$ vg/mouse) without serum treatment.

DETAILED DESCRIPTION

Figure 1A:
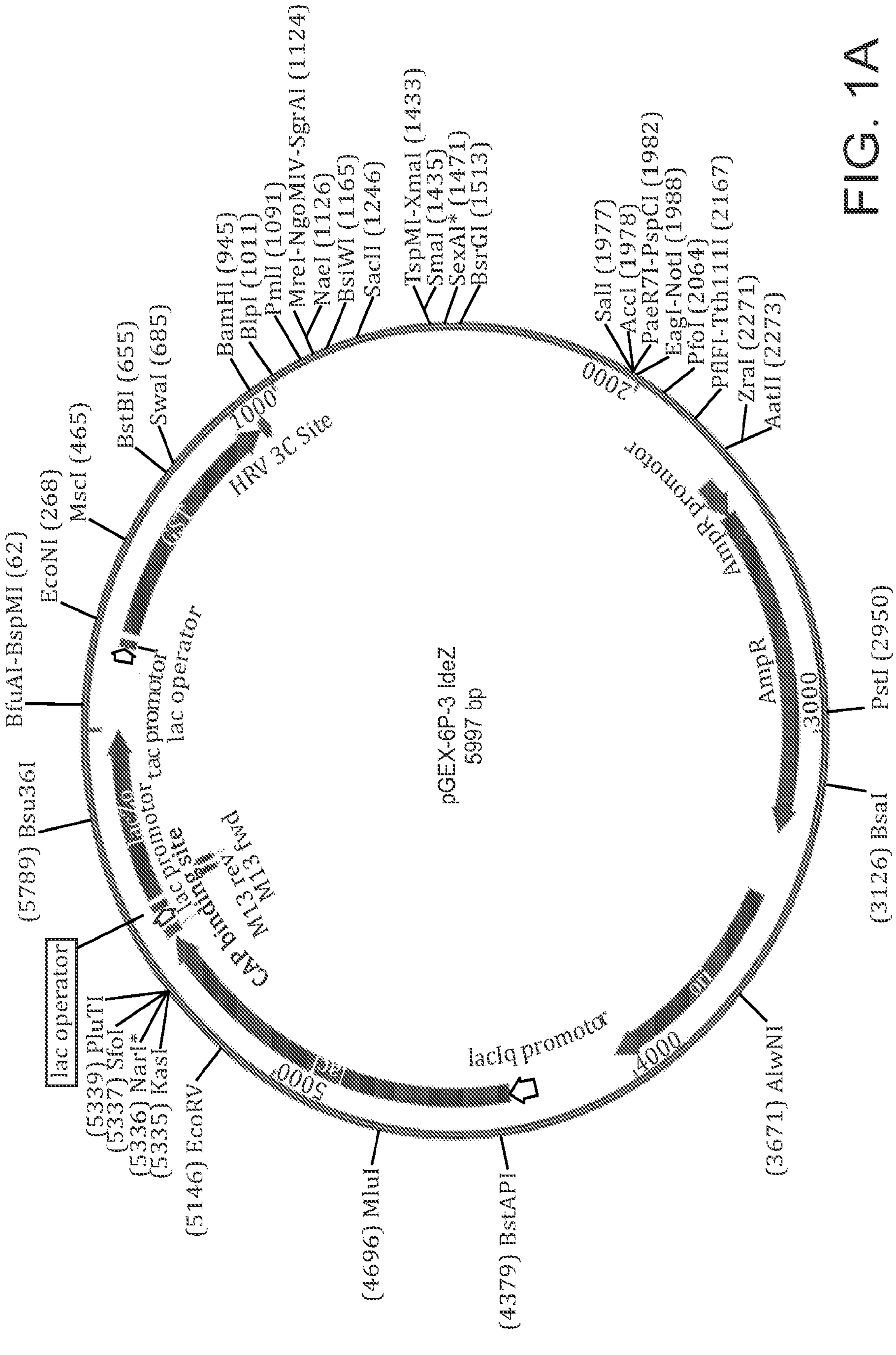
FIG. 1A-1B.

Unless otherwise defined, all technical and scientific terms used herein have the same meaning as commonly understood by one of ordinary skill in the art to which this disclosure belongs. The terminology used in the detailed description herein is for the purpose of describing particular embodiments only and is not intended to be limiting.

All publications, patent applications, patents, GenBank or other accession numbers and other references mentioned herein are incorporated by reference herein in their entirety.

The designation of all amino acid positions in the AAV capsid proteins in the disclosure and the appended claims is with respect to VP1 capsid subunit numbering. It will be understood by those skilled in the art that the modifications described herein if inserted into the AAV cap gene may result in modifications in the VP1, VP2 and/or VP3 capsid subunits. Alternatively, the capsid subunits can be expressed independently to achieve modification in only one or two of the capsid subunits (VP1, VP2, VP3, VP1+VP2, VP1+VP3, or VP2+VP3).

Unless the context indicates otherwise, it is specifically intended that the various features described herein can be used in any combination.

Definitions

The following terms are used in the description herein and the appended claims:

The singular forms "a," "an" and "the" are intended to include the plural forms as well, unless the context clearly indicates otherwise.

Furthermore, the term "about" as used herein when referring to a measurable value such as an amount of the length of a polynucleotide or polypeptide sequence, dose, time, temperature, and the like, is meant to encompass variations of ±20%, ±10%, ±5%, ±1%, ±0.5%, or even ±0.1% of the specified amount.

Also as used herein, "and/or" refers to and encompasses any and all possible combinations of one or more of the associated listed items, as well as the lack of combinations when interpreted in the alternative ("or").

Recitation of ranges of values herein are merely intended to serve as a shorthand method of referring individually to each separate value falling within the range, unless otherwise-indicated herein, and each separate value is incorporated into the specification as if it were individually recited herein. For example, if a concentration range is stated as 1% to 50%, it is intended that values such as 2% to 40%, 10% to 30%, or 1% to 3%, etc., are expressly enumerated in this specification. These are only examples of what is specifically intended, and all possible combinations of numerical values between and including the lowest value and the highest value enumerated are to be considered to be expressly stated in this disclosure.

As used herein, the term "adeno-associated virus" (AAV), includes but is not limited to, AAV type 1, AAV type 2, AAV type 3 (including types 3A and 3B), AAV type 4, AAV type 5, AAV type 6, AAV type 7, AAV type 8, AAV type 9, AAV type 10, AAV type 11, AAV type 12, AAV type 13, AAV type rh32.33, AAV type rh8, AAV type rh10, AAV type rh74, AAV type hu.68, avian AAV, bovine AAV, canine AAV, equine AAV, ovine AAV, snake AAV, bearded dragon AAV, AAV2i8, AAV2g9, AAV-LK03, AAV7m8, AAV Anc80, AAV PHP.B, and any other AAV now known or later discovered. See, e.g., BERNARD N. FIELDS et al., VIROLOGY, volume 2, chapter 69 (4th ed., Lippincott-Raven Publishers). A number of AAV serotypes and clades have been identified (see, e.g., Gao et al, (2004) J. Virology 78:6381-6388; Moris et al, (2004) Virology 33-:375-383; and Table 2). In some embodiments, an AAV vector is selected from any of the AAV vectors disclosed in Table 1 of WO 2019/028306, which is incorporated by reference herein in its entirety.

As used herein, the term "chimeric AAV" refers to an AAV comprising a capsid protein with regions, domains, individual amino acids that are derived from two or more different serotypes of AAV. In some embodiments, a chimeric AAV comprises a capsid protein comprised of a first region that is derived from a first AAV serotype and a second region that is derived from a second AAV serotype. In some embodiments, a chimeric AAV comprises a capsid protein comprised of a first region that is derived from a first AAV serotype, a second region that is derived from a second AAV serotype, and a third region that is derived from a third AAV serotype. In some embodiments, the chimeric AAV may comprise regions, domains, individual amino acids derived from two or more of AAV1, AAV2, AAV3, AAV4, AAV5, AAV6, AAV7, AAV8, AAV9, AAV10, AAV11, and/or AAV12. For example, the chimeric AAV may include regions, domains, and/or individual amino acids from a first and a second AAV serotype as shown below (Table 1), wherein AAVX+Y indicates a chimeric AAV including sequences derived from AAVX and AAVY.

TABLE 1

Chimeric AAVs

| | | Second AAV Serotype | | | | | |
|---|---|---|---|---|---|---|---|
| | | AAV1 | AAV2 | AAV3 | AAV4 | AAV5 | AAV6 |
| First | AAV1 | x | AAV1 + 2 | AAV1 + 3 | AAV1 + 4 | AAV1 + 5 | AAV1 + 6 |
| AAV | AAV2 | AAV2 + 1 | x | AAV2 + 3 | AAV2 + 4 | AAV2 + 5 | AAV2 + 6 |
| Sertoype | AAV3 | AAV3 + 1 | AAV3 + 2 | x | AAV3 + 4 | AAV3 + 5 | AAV3 + 6 |
| | AAV4 | AAV4 + 1 | AAV4 + 2 | AAV4 + 3 | x | AAV4 + 5 | AAV4 + 6 |
| | AAV5 | AAV5 + 1 | AAV5 + 2 | AAV5 + 3 | AAV5 + 4 | x | AAV5 + 6 |
| | AAV6 | AAV6 + 1 | AAV6 + 2 | AAV6 + 3 | AAV6 + 4 | AAV6 + 5 | x |
| | AAV7 | AAV7 + 1 | AAV7 + 2 | AAV7 + 3 | AAV7 + 4 | AAV7 + 5 | AAV7 + 6 |
| | AAV8 | AAV8 + 1 | AAV8 + 2 | AAV8 + 3 | AAV8 + 4 | AAV8 + 5 | AAV8 + 6 |
| | AAV9 | AAV9 + 1 | AAV9 + 2 | AAV9 + 3 | AAV9 + 4 | AAV9 + 5 | AAV9 + 6 |

TABLE 1-continued

| Chimeric AAVs | | | | | | | |
|---|---|---|---|---|---|---|---|
| | AAV10 | AAV10 + 1 | AAV10 + 2 | AAV10 + 3 | AAV10 + 4 | AAV10 + 5 | AAV10 + 6 |
| | AAV11 | AAV11 + 1 | AAV11 + 2 | AAV11 + 3 | AAV11 + 4 | AAV11 + 5 | AAV11 + 6 |
| | AAV12 | AAV12 + 1 | AAV12 + 2 | AAV12 + 3 | AAV12 + 4 | AAV12 + 5 | AAV12 + 6 |

| | | Second AAV Serotype | | | | | |
|---|---|---|---|---|---|---|---|
| | | AAV7 | AAV8 | AAV9 | AAV10 | AAV11 | AAV12 |
| First AAV Sertoype | AAV1 | AAV1 + 7 | AAV1 + 8 | AAV1 + 9 | AAV1 + 10 | AAV1 + 11 | AAV1 + 12 |
| | AAV2 | AAV2 + 7 | AAV2 + 8 | AAV2 + 9 | AAV2 + 10 | AAV2 + 11 | AAV2 + 12 |
| | AAV3 | AAV3 + 7 | AAV3 + 8 | AAV3 + 9 | AAV3 + 10 | AAV3 + 11 | AAV3 + 12 |
| | AAV4 | AAV4 + 7 | AAV4 + 8 | AAV4 + 9 | AAV4 + 10 | AAV4 + 11 | AAV4 + 12 |
| | AAV5 | AAV5 + 7 | AAV5 + 8 | AAV5 + 9 | AAV5 + 10 | AAV5 + 11 | AAV5 + 12 |
| | AAV6 | AAV6 + 7 | AAV6 + 8 | AAV6 + 9 | AAV6 + 10 | AAV6 + 11 | AAV6 + 12 |
| | AAV7 | x | AAV7 + 8 | AAV7 + 9 | AAV7 + 10 | AAV7 + 11 | AAV7 + 12 |
| | AAV8 | AAV8 + 7 | x | AAV8 + 9 | AAV8 + 10 | AAV8 + 11 | AAV8 + 12 |
| | AAV9 | AAV9 + 7 | AAV9 + 8 | x | AAV9 + 10 | AAV9 + 11 | AAV9 + 12 |
| | AAV10 | AAV10 + 7 | AAV10 + 8 | AAV10 + 9 | x | AAV10 + 11 | AAV10 + 12 |
| | AAV11 | AAV11 + 7 | AAV11 + 8 | AAV11 + 9 | AAV11 + 10 | x | AAV11 + 12 |
| | AAV12 | AAV12 + 7 | AAV12 + 8 | AAV12 + 9 | AAV12 + 10 | AAV12 + 11 | x |

By including individual amino acids or regions from multiple AAV serotypes in one capsid protein, capsid proteins that have multiple desired properties that are separately derived from the multiple AAV serotypes may be obtained.

The genomic sequences of various serotypes of AAV and the autonomous parvoviruses, as well as the sequences of the native terminal repeats (TRs), Rep proteins, and capsid subunits are known in the art. Such sequences may be found in the literature or in public databases such as GenBank. See, e.g., GenBank Accession Numbers NC_002077, NC_001401, NC_001729, NC_001863, NC_001829, NC_001862, NC_000883, NC_001701, NC_001510, NC_006152, NC_006261, AF063497, U89790, AF043303, AF028705, AF028704, J02275, J01901, J02275, X01457, AF288061, AH009962, AY028226, AY028223, NC_001358, NC_001540, AF513851, AF513852, AY530579; the disclosures of which are incorporated by reference herein for teaching parvovirus and AAV nucleic acid and amino acid sequences. See also, e.g., Srivistava et al., (1983) J. Virology 45:555; Chiorini et al, (1998) J Virology 71:6823; Chiorini et al., (1999) J. Virology 73: 1309; Bantel-Schaal et al., (1999) J Virology 73:939; Xiao et al, (1999) J Virology 73:3994; Muramatsu et al., (1996) Virology 221:208; Shade et al, (1986) J. Virol. 58:921; Gao et al, (2002) Proc. Nat. Acad. Sci. USA 99:11854; Moris et al, (2004) Virology 33:375-383; international patent publications WO 00/28061, WO 99/61601, WO 98/11244; and U.S. Pat. No. 6,156,303; the disclosures of which are incorporated by reference herein for teaching parvovirus and AAV nucleic acid and amino acid sequences. See also Table 2. The capsid structures of autonomous parvoviruses and AAV are described in more detail in BERNARD N. FIELDS et al., VIROLOGY, volume 2, chapters 69 & 70 (4th ed., Lippincott-Raven Publishers). See also, description of the crystal structure of AAV2 (Xie et al., (2002) Proc. Nat. Acad. Sci. 99: 10405-10), AAV9 (DiMattia et al., (2012) J. Virol. 86:6947-6958), AAV8 (Nam et al, (2007) J. Virol. 81: 12260-12271), AAV6 (Ng et al., (2010) J. Virol. 84:12945-12957), AAV5 (Govindasamy et al. (2013) J. Virol. 87, 11187-11199), AAV4 (Govindasamy et al. (2006) J. Virol. 80:11556-11570), AAV3B (Lerch et al., (2010) Virology 403:26-36), BPV (Kailasan et al., (2015) J. Virol. 89:2603-2614) and CPV (Xie et al, (1996) J. Mol. Biol. 6:497-520 and Tsao et al, (1991) Science 251:1456-64).

TABLE 2

| Complete Genomes | GenBank Accession Number |
|---|---|
| Adeno-associated virus 1 | NC_002077, AF063497 |
| Adeno-associated virus 2 | NC_001401 |
| Adeno-associated virus 3 | NC_001729 |
| Adeno-associated virus 3B | NC_001863 |
| Adeno-associated virus 4 | NC_001829 |
| Adeno-associated virus 5 | Y18065, AF085716 |
| Adeno-associated virus 6 | NC_001862 |
| Avian AAV ATCC VR-865 | AY186198, AY629583, NC_004828 |
| Avian AAV strain DA-1 | NC_006263, AY629583 |
| Bovine AAV | NC_005889, AY388617, AAR26465 |
| AAV11 | AA146339, AY631966 |
| AAV12 | AB116639, DQ813647 |
| Clade A | |
| AAV1 | NC_002077, AF063497 |
| AAV6 | NC_001862 |
| Hu.48 | AY530611 |
| Hu 43 | AY530606 |
| Hu 44 | AY530607 |
| Hu 46 | AY530609 |
| Clade B | |
| Hu. 19 | AY530584 |
| Hu. 20 | AY530586 |
| Hu 23 | AY530589 |
| Hu22 | AY530588 |
| Hu24 | AY530590 |
| Hu21 | AY530587 |
| Hu27 | AY530592 |
| Hu28 | AY530593 |
| Hu 29 | AY530594 |
| Hu63 | AY530624 |
| Hu64 | AY530625 |

TABLE 2-continued

| Complete Genomes | GenBank Accession Number |
|---|---|
| Hu13 | AY530578 |
| Hu56 | AY530618 |
| Hu57 | AY530619 |
| Hu49 | AY530612 |
| Hu58 | AY530620 |
| Hu34 | AY530598 |
| Hu35 | AY530599 |
| AAV2 | NC_001401 |
| Hu45 | AY530608 |
| Hu47 | AY530610 |
| Hu51 | AY530613 |
| Hu52 | AY530614 |
| Hu T41 | AY695378 |
| Hu S17 | AY695376 |
| Hu T88 | AY695375 |
| Hu T71 | AY695374 |
| Hu T70 | AY695373 |
| Hu T40 | AY695372 |
| Hu T32 | AY695371 |
| Hu T17 | AY695370 |
| Hu LG15 | AY695377 |
| Clade C | |
| Hu9 | AY530629 |
| Hu10 | AY530576 |
| Hu11 | AY530577 |
| Hu53 | AY530615 |
| Hu55 | AY530617 |
| Hu54 | AY530616 |
| Hu7 | AY530628 |
| Hu18 | AY530583 |
| Hu15 | AY530580 |
| Hu16 | AY530581 |
| Hu25 | AY530591 |
| Hu60 | AY530622 |
| Ch5 | AY243021 |
| Hu3 | AY530595 |
| Hu1 | AY530575 |
| Hu4 | AY530602 |
| Hu2 | AY530585 |
| Hu61 | AY530623 |
| Clade D | |
| Rh62 | AY530573 |
| Rh48 | AY530561 |
| Rh54 | AY530567 |
| Rh55 | AY530568 |
| Cy2 | AY243020 |
| AAV7 | AF513851 |
| Rh35 | AY243000 |
| Rh37 | AY242998 |
| Rh36 | AY242999 |
| Cy6 | AY243016 |
| Cy4 | AY243018 |
| Cy3 | AY243019 |
| Cy5 | AY243017 |
| Rh13 | AY243013 |
| Clade E | |
| Rh38 | AY530558 |
| Hu66 | AY530626 |
| Hu42 | AY530605 |
| Hu67 | AY530627 |
| Hu40 | AY530603 |
| Hu41 | AY530604 |
| Hu37 | AY530600 |
| Rh40 | AY530559 |
| Rh2 | AY243007 |
| Bb1 | AY243023 |
| Bb2 | AY243022 |
| Rh10 | AY243015 |
| Hu17 | AY530582 |
| Hu6 | AY530621 |
| Rh25 | AY530557 |
| Pi2 | AY530554 |
| Pi1 | AY530553 |

TABLE 2-continued

| Complete Genomes | GenBank Accession Number |
|---|---|
| Pi3 | AY530555 |
| Rh57 | AY530569 |
| Rh50 | AY530563 |
| Rh49 | AY530562 |
| Hu39 | AY530601 |
| Rh58 | AY530570 |
| Rh61 | AY530572 |
| Rh52 | AY530565 |
| Rh53 | AY530566 |
| Rh51 | AY530564 |
| Rh64 | AY530574 |
| Rh43 | AY530560 |
| AAV8 | AF513852 |
| Rh8 | AY242997 |
| Rh1 | AY530556 |
| Clade F | |
| Hu14 (AAV9) | AY530579 |
| Hu31 | AY530596 |
| Hu32 | AY530597 |
| HSC1 | M1332400.1 |
| HSC2 | MI332401.1 |
| HSC3 | MI332402.1 |
| HSC4 | M1332403.1 |
| HSC5 | M1332405.1 |
| HSC6 | M1332404.1 |
| HSC7 | M1332407.1 |
| HSC8 | M1332408.1 |
| HSC9 | M1332409.1 |
| HSC11 | M1332406.1 |
| HSC12 | M1332410.1 |
| HSC13 | M1332411.1 |
| HSC14 | M1332412.1 |
| HSC15 | M1332413.1 |
| HSC16 | M1332414.1 |
| HSC17 | M1332415.1 |
| Hu68 | |
| Clonal Isolate | |
| AAV5 | Y18065, AF085716 |
| AAV 3 | NC_001729 |
| AAV 3B | NC_01863 |
| AAV4 | NC_001829 |
| Rh34 | AY243001 |
| Rh33 | AY243002 |
| Rh32 | AY243003 |
| Others | |
| Rh74 | |
| Bearded Dragon AAV | |
| Snake AAV | NC_006148.1 |

The term "tropism" as used herein refers to preferential entry of the virus into certain cells or tissues, optionally followed by expression (e.g., transcription and, optionally, translation) of a sequence(s) carried by the viral genome in the cell, e.g., for a recombinant virus, expression of a heterologous nucleic acid(s) of interest.

Those skilled in the art will appreciate that transcription of a heterologous nucleic acid sequence from the viral genome may not be initiated in the absence of trans-acting factors, e.g., for an inducible promoter or otherwise regulated nucleic acid sequence. In the case of a rAAV genome, gene expression from the viral genome may be from a stably integrated provirus, from a non-integrated episome, as well as any other form in which the virus may take within the cell.

As used here, "systemic tropism" and "systemic transduction" (and equivalent terms) indicate that the virus capsid or virus vector of the disclosure exhibits tropism for or transduces, respectively, tissues throughout the body (e.g., brain, lung, skeletal muscle, heart, liver, kidney and/or pancreas). In embodiments, systemic transduction of muscle tissues (e.g., skeletal muscle, diaphragm and cardiac muscle) is observed. In other embodiments, systemic transduction of skeletal muscle tissues achieved. For example, in particular embodiments, essentially all skeletal muscles throughout the body are transduced (although the efficiency of transduction may vary by muscle type). In particular embodiments, systemic transduction of limb muscles, cardiac muscle and diaphragm muscle is achieved. Optionally, the virus capsid or virus vector is administered via a systemic route (e.g., systemic route such as intravenously, intra-articularly or intra-lymphatically). Alternatively, in other embodiments, the capsid or virus vector is delivered locally (e.g., to the footpad, intramuscularly, intradermally, subcutaneously, topically).

Unless indicated otherwise, "efficient transduction" or "efficient tropism," or similar terms, can be determined by reference to a suitable control (e.g., at least about 50%, about 60%, about 70%, about 80%, about 85%, about 90%, about 95% or more of the transduction or tropism, respectively, of the control). In some embodiments, the virus vector efficiently transduces or has efficient tropism for skeletal muscle, cardiac muscle, diaphragm muscle, pancreas (including (3-islet cells), spleen, the gastrointestinal tract (e.g., epithelium and/or smooth muscle), cells of the central nervous system, lung, joint cells, and/or kidney. Suitable controls will depend on a variety of factors including the desired tropism profile. For example, AAV8 and AAV9 are highly efficient in transducing skeletal muscle, cardiac muscle and diaphragm muscle, but have the disadvantage of also transducing liver with high efficiency. Thus, viral vectors can be identified that demonstrate the efficient transduction of skeletal, cardiac and/or diaphragm muscle of AAV8 or AAV9, but with a much lower transduction efficiency for liver. Further, because the tropism profile of interest may reflect tropism toward multiple target tissues, it will be appreciated that a suitable vector may represent some tradeoffs. To illustrate, a virus vector of the disclosure may be less efficient than AAV8 or AAV9 in transducing skeletal muscle, cardiac muscle and/or diaphragm muscle, but because of low level transduction of liver, may nonetheless be very desirable.

Similarly, it can be determined if a virus "does not efficiently transduce" or "does not have efficient tropism" for a target tissue, or similar terms, by reference to a suitable control. In particular embodiments, the virus vector does not efficiently transduce (i.e., has does not have efficient tropism) for liver, kidney, gonads and/or germ cells. In particular embodiments, undesirable transduction of tissue(s) (e.g., liver) is about 20% or less, about 10% or less, about 5% or less, about 1% or less, about 0.1% or less of the level of transduction of the desired target tissue(s) (e.g., skeletal muscle, diaphragm muscle, cardiac muscle and/or cells of the central nervous system).

As used herein, the term "polypeptide" encompasses both peptides and proteins, unless indicated otherwise.

A "polynucleotide" is a sequence of nucleotide bases, and may be RNA, DNA or DNA-RNA hybrid sequences (including both naturally occurring and non-naturally occurring nucleotide), but in representative embodiments are either single or double stranded DNA sequences.

As used herein, an "isolated" polynucleotide (e.g., an "isolated DNA" or an "isolated RNA") means a polynucleotide at least partially separated from at least some of the other components of the naturally occurring organism or virus, for example, the cell or viral structural components or other polypeptides or nucleic acids commonly found associated with the polynucleotide. In representative embodiments an "isolated" nucleotide is enriched by at least about 10-fold, about 100-fold, about 1000-fold, about 10,000-fold or more as compared with the starting material.

Likewise, an "isolated" polypeptide means a polypeptide that is at least partially separated from at least some of the other components of the naturally occurring organism or virus, for example, the cell or viral structural components or other polypeptides or nucleic acids commonly found associated with the polypeptide. In representative embodiments an "isolated" polypeptide is enriched by at least about 10-fold, about 100-fold, about 1000-fold, about 10,000-fold or more as compared with the starting material.

As used herein, by "isolate" or "purify" (or grammatical equivalents) a polypeptide or a virus vector, it is meant that the polypeptide or the virus vector is at least partially separated from at least some of the other components in the starting material. In representative embodiments an "isolated" or "purified" polypeptide or virus vector is enriched by at least about 10-fold, about 100-fold, about 1000-fold, about 10,000-fold or more as compared with the starting material.

The compositions and methods disclosed herein find use in both veterinary and medical applications. Suitable subjects include both avians and mammals. The term "avian" as used herein includes, but is not limited to, chickens, ducks, geese, quail, turkeys, pheasant, parrots, parakeets, and the like. The term "mammals" as used herein includes, but is not limited to, humans, non-human primates, bovines, ovines, caprines, equines, felines, canines, lagomorphs, etc. Human subjects include neonates, infants, juveniles, adults and geriatric subjects. In some embodiments, a human subject can be less than 6 months old, less than 2 years old, less than 5 years old, less than 10 years old, 10-18 years old, 19-29 years old, 30-35 years old, 36-40 years old, or older than 40 years old. In representative embodiments, the subject is "in need" of the methods described herein. The terms "subject" and "patient" are used interchangeably herein in reference to a human subject.

A "therapeutic polypeptide" is a polypeptide that can alleviate, reduce, prevent, delay and/or stabilize symptoms that result from an absence or defect in a protein in a cell or subject and/or is a polypeptide that otherwise confers a benefit to a subject, e.g., anti-cancer effects or improvement in transplant survivability.

By the terms "treat," "treating" or "treatment of" (and grammatical variations thereof) it is meant that the severity of the subject's condition is reduced, at least partially improved or stabilized and/or that some alleviation, mitigation, decrease or stabilization in at least one clinical symptom is achieved and/or there is a delay in the progression of the disease or disorder.

The terms "prevent," "preventing" and "prevention" (and grammatical variations thereof) refer to prevention and/or delay of the onset of a disease, disorder and/or a clinical symptom(s) in a subject and/or a reduction in the severity of the onset of the disease, disorder and/or clinical symptom(s) relative to what would occur in the absence of the methods of the disclosure. The prevention can be complete, e.g., the total absence of the disease, disorder and/or clinical symptom(s). The prevention can also be partial, such that the occurrence of the disease, disorder and/or clinical symptom(s) in the subject and/or the severity of onset is less than what would occur in the absence of the present disclosure.

"Effective amount" refers to an amount that, when administered to a subject for treating a disease, disorder or condition, is sufficient to affect or alleviate one or more symptoms of the disease, disorder, or condition. The "effective amount" may vary depending, for example, on the disease, disorder, or condition, and/or symptoms thereof, the severity of the disease, disorder, condition and/or symptoms thereof, the age, weight, and/or health of the subject, and the judgment of the prescribing physician. An appropriate amount in any given instance may be ascertained by those skilled in the art or capable of determination by routine experimentation. In some embodiments, the effective amount is a therapeutically effective amount.

As used herein, the terms "virus vector," or "gene delivery vector" refer to a virus (e.g., AAV) particle that functions as a nucleic acid delivery vehicle, and which comprises the vector genome (e.g., viral DNA [vDNA]) packaged within a virion. Alternatively, in some contexts, the term "virus vector" may be used to refer to the viral vector genome/vDNA alone.

A "rAAV vector genome" or "rAAV genome" is an AAV genome (i.e., vDNA) that comprises one or more heterologous nucleic acid sequences. rAAV vectors generally require only the terminal repeat(s) (TR(s)) in cis to generate virus. All other viral sequences are dispensable and may be supplied in trans. Typically, the rAAV vector genome will only retain the one or more TR sequence so as to maximize the size of the transgene that can be efficiently packaged by the vector. The structural and non-structural protein coding sequences may be provided in trans (e.g., from a vector, such as a plasmid, or by stably integrating the sequences into a packaging cell). In embodiments, the rAAV vector genome comprises at least one TR sequence (e.g., AAV TR sequence), optionally two TRs (e.g., two AAV TRs), which typically will be at the 5' and 3' ends of the vector genome and flank the heterologous nucleic acid, but need not be contiguous thereto. The TRs can be the same or different from each other.

The term "terminal repeat" or "TR" includes any viral terminal repeat or synthetic sequence that forms a hairpin structure and functions as an inverted terminal repeat (i.e., mediates the desired functions such as replication, virus packaging, integration and/or provirus rescue, and the like). The TR can be an AAV TR or a non-AAV TR. For example, a non-AAV TR sequence such as those of other parvoviruses (e.g., canine parvovirus (CPV), mouse parvovirus (MVM), human parvovirus B-19) or any other suitable virus sequence (e.g., the SV40 hairpin that serves as the origin of SV40 replication) can be used as a TR, which can further be modified by truncation, substitution, deletion, insertion and/or addition. Further, the TR can be partially or completely synthetic.

An "AAV terminal repeat" or "AAV TR" may be from any AAV, including but not limited to serotypes 1, 2, 3, 4, 5, 6, 7, 8, 9, 10, 11, 12, 13 or any other AAV now known or later discovered (see, e.g., Table 2). An AAV terminal repeat need not have the native terminal repeat sequence (e.g., a native AAV TR sequence may be altered by insertion, deletion, truncation and/or missense mutations), as long as the terminal repeat mediates the desired functions, e.g., replication, virus packaging, integration, and/or provirus rescue, and the like.

The virus vectors of the disclosure can further be "targeted" virus vectors (e.g., having a directed tropism) and/or a "hybrid" parvovirus (i.e., in which the viral TRs and viral capsid are from different parvoviruses). The virus vectors of the disclosure can further be duplexed parvovirus particles. Thus, in some embodiments, double stranded (duplex) genomes can be packaged into the virus capsids of the disclosure. Further, the viral capsid or genomic elements can contain other modifications, including insertions, deletions and/or substitutions.

As used herein, the term "amino acid" encompasses any naturally occurring amino acid, modified forms thereof, and synthetic amino acids.

Naturally occurring, levorotatory (L-) amino acids are shown in Table 3.

TABLE 3

Amino acid residues and abbreviations.

| Amino Acid Residue | Abbreviation: Three-Letter Code | Abbreviation: One-Letter Code |
|---|---|---|
| Alanine | Ala | A |
| Arginine | Arg | R |
| Asparagine | Asn | N |
| Aspartic acid (Aspartate) | Asp | D |
| Cysteine | Cys | C |
| Glutamine | Gln | Q |
| Glutamic acid (Glutamate) | Glu | E |
| Glycine | Gly | G |
| Histidine | His | H |
| Isoleucine | Ile | I |
| Leucine | Leu | L |
| Lysine | Lys | K |
| Methionine | Met | M |
| Phenylalanine | Phe | F |
| Proline | Pro | P |
| Serine | Ser | S |
| Threonine | Thr | T |
| Tryptophan | Trp | W |
| Tyrosine | Tyr | Y |
| Valine | Val | V |

Alternatively, the amino acid can be a modified amino acid residue (nonlimiting examples are shown in Table 4) and/or can be an amino acid that is modified by post-translational modification (e.g., acetylation, amidation, formylation, hydroxylation, methylation, phosphorylation or sulfatation).

TABLE 4

Modified Amino Acid Residues

| Modified Amino Acid Residue | Abbreviation |
|---|---|
| Amino Acid Residue Derivatives | |
| 2-Aminoadipic acid | Aad |
| 3-Aminoadipic acid | bAad |
| beta-Alanine, beta-Aminoproprionic acid | bAla |
| 2-Aminobutyric acid | Abu |
| 4-Aminobutyric acid, Piperidinic acid | 4Abu |
| 6-Aminocaproic acid | Acp |
| 2-Aminoheptanoic acid | Ahe |
| 2-Aminoisobutyric acid | Aib |
| 3-Aminoisobutyric acid | bAib |
| 2-Aminopimelic acid | Apm |
| t-butylalanine | t-BuA |
| Citrulline | Cit |
| Cyclohexylalanine | Cha |
| 2,4-Diaminobutyric acid | Dbu |
| Desmosine | Des |
| 2,21-Diaminopimelic acid | Dpm |
| 2,3-Diaminoproprionic acid | Dpr |
| N-Ethylglycine | EtGly |
| N-Ethylasparagine | EtAsn |
| Homoarginine | hArg |
| Homocysteine | hCys |
| Homoserine | hSer |

TABLE 4-continued

| Modified Amino Acid Residues | |
|---|---|
| Modified Amino Acid Residue | Abbreviation |
| Amino Acid Residue Derivatives | |
| Hydroxylysine | Hyl |
| Allo-Hydroxylysine | aHyl |
| 3-Hydroxyproline | 3Hyp |
| 4-Hydroxyproline | 4Hyp |
| Isodesmosine | Ide |
| allo-Isoleucine | aIle |
| Methionine sulfoxide | MSO |
| N-Methylglycine, sarcosine | MeGly |
| N-Methyl isoleucine | MeIle |
| 6-N-Methyllysine | MeLys |
| N-Methylvaline | MeVal |
| 2-Naphthylalanine | 2-Nal |
| Norvaline | Nva |
| Norleucine | Nle |
| Ornithine | Orn |
| 4-Chlorophenylalanine | Phe(4-C1) |
| 2-Fluorophenylalanine | Phe(2-F) |
| 3-Fluorophenylalanine | Phe(3-F) |
| 4-Fluorophenylalanine | Phe(4-F) |
| Phenylglycine | Phg |
| Beta-2-thienylalanine | Thi |

Further, the non-naturally occurring amino acid can be an "unnatural" amino acid (as described by Wang et al., Annu Rev Biophys Biomol Struct. 35:225-49 (2006)). These unnatural amino acids can advantageously be used to chemically link molecules of interest to the AAV capsid protein.

The term "domain" as used herein is intended to encompass a part of a protein sequence and structure that can evolve, function, and exist independently of the rest of the protein chain. A domain is capable of forming a compact three-dimensional structure and often can be independently stable and folded. One domain may appear in a variety of evolutionarily related proteins. Domains vary in length from between about 25 amino acids up to about 500 amino acids in length. A "domain" can also encompass a domain from a wild-type protein that has had an amino acid residue, or residues, replaced by conservative substitution. Because they are self-stable in a protein milieu, domains can be "swapped" by genetic engineering between one protein and another to make chimeric proteins.

The terms "mutant," "mutants," "variant" or "variants," as used herein, are intended to designate a native protein or AAV, wherein one or more amino acids of the parent protein or AAV have been substituted by another amino acid and/or wherein one or more amino acids of the parent AAV protein have been deleted and/or wherein one or more amino acids have been inserted in the protein or AAV and/or wherein one or more amino acids have been added to the parent protein or AAV. Such additions can take place either at the N-terminal end or at the C-terminal end of the parent protein or both, as well as internally. In some embodiments, the amino acid sequence of a variant is at least 40%, at least 50%, at least 60% or at least 70% identical with the amino acid sequence of the native protein.

The term "vector," as used herein, means any nucleic acid entity capable of amplification in a host cell. Thus, the vector may be an autonomously replicating vector, i.e., a vector, which exists as an extrachromosomal entity, the replication of which is independent of chromosomal replication, e.g., a plasmid. Alternatively, the vector may be one which, when introduced into a host cell, is integrated into the host cell genome and replicated together with the chromosome(s) into which it has been integrated. The choice of vector will often depend on the host cell into which it is to be introduced. Vectors include, but are not limited to plasmid vectors, phage vectors, viruses or cosmid vectors. Vectors usually contain a replication origin and at least one selectable gene, i.e., a gene which encodes a product which is readily detectable or the presence of which is essential for cell growth.

The term "gene therapy" refers to a method of changing the expression of an endogenous gene by exogenous administration of a gene. As used herein, "gene therapy" also refers to the replacement of defective gene encoding a defective protein, or replacement of a missing gene, by introducing a functional gene corresponding to the defective or missing gene into somatic or stem cells of an individual in need. Gene therapy can be accomplished by ex vivo methods, in which differentiated or somatic stem cells are removed from the individual's body followed by the introduction of a normal copy of the defective gene into the explanted cells using a viral vector as the gene delivery vehicle. In addition, in vivo direct gene transfer technologies allow for gene transfer into cells in the individual in situ using a broad range of viral vectors, liposomes, protein DNA complexes or naked DNA in order to achieve a therapeutic outcome. The term "gene therapy" also refers to the replacement of a defective gene encoding a defective protein by introducing a polynucleotide that functions substantially the same as the defective gene or protein should function if it were not defective into somatic or stem cells of an individual in need.

The term "gene editing" refers to the insertion, deletion, or replacement of DNA at a specific site in the genome of an organism or cell. Gene editing may be performed using one or more targeted nuclease systems, such as a CRISPR/Cas system, a CRISPR/Cpf1 system a Zn finger nuclease, a TALEN, a homing endonuclease, etc.

As used herein, the term "Fc receptor" refers to Fc gamma immunoglobulin receptors (FcγRs) which are present on cells. In humans, FcγR refers to one, some, or all of the family of receptors comprising FcγRI (CD64), FcγRIIA (CD32A), FcγRIIB (CD32B), FcγRIIIA (CD16a) and FcγRIIIB (CD16b). As used herein, the term FcγR includes naturally occurring polymorphisms of FcγRI (CD64), FcγγRIIA (CD32A), FcγRIIB (CD32B), FcγRIIIA (CD16a) and FcγRIIIB (CD16b).

As described herein, a cysteine protease is an enzyme that degrades a protein. Cysteine proteases generally have a common catalytic mechanism that involves a nucleophilic cysteine thiol in a catalytic triad or dyad. In some embodiments, a cysteine protease is an IgG cysteine protease which cleaves IgG such that the antigen binding domains (Fab) and constant domains (Fc) are separated from each other.

Compositions for Reducing Neutralizing Antibodies Against a Biologic

The disclosure provides compositions that can reduce neutralizing antibodies against a recombinant biologic or a drug entity in a subject. In some embodiments, the recombinant biologic comprises a vector comprising a heterologous nucleic acid encoding one or more recombinant proteins. In some embodiments, the vector is a recombinant virus vector, such as a recombinant AAV vector.

In some embodiments, the compositions reduce neutralizing antibodies against a recombinant biologic or a drug entity in a subject by promoting the clearance or degradation of an antibody against the recombinant biologic or the drug entity; and/or by reducing the binding of an antibody against the recombinant biologic or the drug entity to an Fc receptor. In some embodiments, the compositions reduce neutralizing antibodies against an AAV vector comprising a heterologous nucleic acid in a subject by promoting the clearance or degradation of an antibody against the AAV vector, or one or more recombinant proteins encoded by the heterologous nucleic acid; and/or by reducing the binding of an antibody against the AAV vector to an Fc receptor.

In some embodiments, the compositions comprise an antibody-degrading enzyme, or a fragment thereof, that can degrade antibodies recognizing adeno-associated viral (AAV) capsid proteins or virions; or prevent neutralization of recombinant AAV vectors. In some embodiments, the compositions comprise a vector comprising a polynucleotide encoding an antibody-degrading enzyme, or a fragment thereof. In some embodiments, the antibodies comprise IgG (including IgG1, IgG2a, IgG2b, and/or IgG3), IgM, IgE and/or IgA. In exemplary embodiments, the antibodies comprise IgGs. Therefore, in some embodiments, the composition comprises an IgG-degrading enzyme, or a fragment thereof. In some embodiments, the IgG-degrading enzyme, or a fragment thereof has cysteine protease activity.

In some embodiments, the IgG-degrading enzyme, or the fragment thereof is isolated or derived from bacteria, such as from a bacteria of the genus *Streptococcus*. In some embodiments, the IgG-degrading enzyme comprises an amino acid sequence of at least about 50% (for example, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or 100%, including all values and subranges that lie therebetween) identity to the following amino acid sequence of *S. equi* set forth in SEQ ID NO:1 below:

```
MKTIAYPNKPHSLSAGLLTAIAIFSLASSNITYADDYQRNATEAYA
KEVPHQITSVWSKGVTPLTPEQFRYNNEDVIHAPYLAHQGWYDIT
KAFDGKDNLLCGAATAGNMLHWWFDQNKTEIEAYLSKHPEKQKI
IFNNQELFDLKAAIDTKDSQTNSQLFNYFRDKAFPNLSARQLGVMP
DLVLDMFINGYYLNVFKTQSTDVNRPYQDKDKRGGIFDAVFTRG
DQTTLLTARHDLKNKGLNDISTIIKQELTEGRALALSHTYANVSISH
VINLWGADFNAEGNLEAIYVTDSDANASIGMKKYFVGINAHGHV
AISAKKIEGENIGAQVLGLFTLSSGKDIWQKLS.
```

Figure 5:
FIG. 5.

The sequence of SEQ ID NO: 1 corresponds to the IdeZ protein. An exemplary crystal structure for the IdeZ protein is shown in FIG. 5 in which each panel shows a different view.

The IdeZ protein, disclosed herein, is a cysteine protease identified in group A Streptococci, which inactivates IgG antibodies by cleaving IgG at the lower hinge region of the heavy chain producing one F(ab')2 and one homodimeric Fc fragment. This IgG-degrading enzymes have a short half-life and are mostly cleared from circulation rapidly along with highly efficient but transient IgG removal.

In some embodiments, the IgG-degrading enzyme, or the fragment thereof is isolated or derived from *S. pyogenes*. In some embodiments, the IgG-degrading enzyme comprises an amino acid sequence of at least about 50% (for example, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or 100%, including all values and subranges that lie therebetween) identity to SEQ ID NO:13 or SEQ ID NO: 14.

In some embodiments, the IgG-degrading enzyme, or the fragment thereof, is a synthetic enzyme. In some embodiments, the IgG-degrading enzyme comprises a sequence of at least about 50% (for example, about 55%, about 60%, about 65%, about 70%, about 75%, about 80%, about 85%, about 90%, about 91%, about 92%, about 93%, about 94%, about 95%, about 96%, about 97%, about 98%, about 99%, about 99.5%, or 100%, including all values and subranges that lie therebetween) identity to any one of SEQ ID NO: 15-52.

The compositions for reducing neutralizing antibodies described herein may comprise a fusion protein comprising the antibody-degrading enzyme, or a fragment thereof; and a second protein. In some embodiments, the second protein is an IgG protease.

In some embodiments, the compositions for reducing neutralizing antibodies reduce the binding of an antibody against the AAV vector to an Fc receptor. In some embodiments, the compositions promote rapid clearance of an antibody against the AAV vector by binding to an Fc receptor for the antibody. For instance, the compositions may promote rapid clearance of IgGs against the AAV vector by binding to a receptor for IgGs (for example, FcRN), thereby, also promoting the internalization and degradation of the IgG receptor. In some embodiments, the compositions comprise a therapeutic antibody. In some embodiments, the therapeutic antibody is an IgG. In some embodiments, the therapeutic antibody is rozanolixizumab. In some embodiments, the dose of the therapeutic antibody is 0.05 mg/kg to about 150 mg/kg, for example, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 110 mg/kg, about 120 mg/kg, about 130 mg/kg, about 140 mg/kg, or about 150 mg/kg, including all values and subranges that lie therebetween.

In some embodiments, the compositions for reducing neutralizing antibodies reduce and/or inhibit complement activation. For example, the composition may cleave the neutralizing antibody, thereby preventing C1q from binding to an antigen-antibody complex (e.g., an AAV-antibody complex). By reducing and/or inhibiting complement activation, downstream processes in the complement cascade are prevented, such as recruitment of inflammatory cells and opsonization (e.g., of the AAV). In some embodiments, treatment of a subject with a composition for reducing neutralizing antibodies prior to treatment with an AAV prevents complement activation in the patient upon administration of the AAV, and in some embodiments complement activation is reduced by at least 50%, at least 60%, at least 70%, at least 80%, at least 90%, at least 95%, at least 96%, at least 97%, at least 98%, or at least 99% upon administration of the AAV. In some embodiments, treatment of a patient a composition for reducing neutralizing antibodies concurrently with treatment with an AAV prevents complement activation in the patient due to the AAV treatment, and in some embodiments, complement activation is reduced by at least 50%, at least 60%, at least 70%, at least 80%, at least 90%, at least 95%, at least 96%, at least 97%, at least 98%, or at least 99%. In some embodiments, treatment of a patient with one of the composition for reducing neutralizing antibodies after with treatment with an AAV reduces complement activation in the patient, and in some embodiments, complement activation is reduced by at least 50%, at least 60%, at least 70%, at least 80%, at least 90%, at least 95%, at least 96%, at least 97%, at least 98%, or at least 99%.

In some embodiments, the compositions disclosed herein further comprise at least one pharmaceutically acceptable carrier, excipient, and/or vehicle, for example, solvents, buffers, solutions, dispersion media, coatings, antibacterial and antifungal agents, isotonic and absorption delaying agents. In some embodiments, the pharmaceutically acceptable carrier, excipient, and/or vehicle may comprise saline, buffered saline, dextrose, water, glycerol, sterile isotonic aqueous buffer, phosphate buffered solutions, amino acid-based buffers, bicarbonate buffered solutions, and combinations thereof. In some embodiments, the pharmaceutically acceptable carrier, excipient, and/or vehicle comprises phosphate buffered saline, sterile saline, lactose, sucrose, calcium phosphate, dextran, agar, pectin, peanut oil, sesame oil, pharmaceutical grades of mannitol, lactose, starch, magnesium stearate, sodium saccharine, cellulose, magnesium carbonate, polyol (e.g., glycerol, propylene glycol, and liquid polyethylene glycol, and the like) or suitable mixtures thereof. In some embodiments, the compositions disclosed herein further comprise minor amounts of emulsifying or wetting agents, or pH buffering agents. Formulations of compositions disclosed herein may be prepared for storage by mixing with physiologically acceptable carriers, excipients, or stabilizers in the form of, e.g., lyophilized powders, slurries, aqueous solutions or suspensions (see, e.g., Hardman, et al. (2001) Goodman and Gilman's The Pharmacological Basis of Therapeutics, McGraw-Hill, New York, N.Y.; Gennaro (2000) Remington: The Science and Practice of Pharmacy, Lippincott, Williams, and Wilkins, New York, N.Y.; Avis, et al. (eds.) (1993) Pharmaceutical Dosage Forms: Parenteral Medications, Marcel Dekker, NY; Lieberman, et al. (eds.) (1990) Pharmaceutical Dosage Forms: Tablets, Marcel Dekker, NY; Lieberman, et al. (eds.) (1990) Pharmaceutical Dosage Forms: Disperse Systems, Marcel Dekker, NY; Weiner and Kotkoskie (2000) Excipient Toxicity and Safety, Marcel Dekker, Inc., New York, N.Y.).

In some embodiments, the compositions disclosed herein further comprise other conventional pharmaceutical ingredients, such as preservatives, or chemical stabilizers, such as chlorobutanol, potassium sorbate, sorbic acid, sulfur dioxide, propyl gallate, the parabens, ethyl vanillin, glycerin, phenol, parachlorophenol or albumin. In some embodiments, the compositions disclosed herein may further comprise antibacterial and antifungal agents, such as, parabens, chlorobutanol, phenol, sorbic acid or thimerosal; isotonic agents, such as, sugars or sodium chloride and/or agents delaying absorption, such as, aluminum monostearate and gelatin.

In some embodiments, the compositions of the present disclosure are formulated in a neutral or salt form. Pharmaceutically-acceptable salts include, for example, acid addition salts (formed with the free amino groups of the protein) derived from inorganic acids, e.g., hydrochloric or phosphoric acids, or from organic acids, e.g., acetic, oxalic, tartaric, mandelic, and the like. In some embodiments, the salts formed with the free carboxyl groups of the protein may be derived from inorganic bases (e.g., sodium, potassium, ammonium, calcium, or ferric hydroxides) or from organic bases (e.g., isopropylamine, trimethylamine, histidine, procaine) and the like.

In some embodiments, the composition is in a solid form, such as a lyophilized powder suitable for reconstitution, a liquid solution, suspension, emulsion, tablet, pill, capsule, sustained release formulation, or powder. In some embodiments, the composition may be formulated for delivery using liposomes, nanocapsules, microparticles, microspheres, lipid particles, vesicles, liposome, nanosphere, nanoparticle and the like.

Dosage and Modes of Administration of Compositions for Reducing Neutralizing Antibodies Administration of any one of the compositions disclosed herein for reducing neutralizing antibodies against a biologic may be performed by an injection, infusion, or a combination thereof. A pharmaceutical composition comprising any one of the compositions described herein may be administered at a dosage of about 0.05 mg/kg to about 150 mg/kg, for example, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 110 mg/kg, about 120 mg/kg, about 130 mg/kg, about 140 mg/kg, or about 150 mg/kg, including all values and subranges that lie therebetween.

A therapeutically effective amount of any one of the compositions disclosed herein may be given in one dose, but is not restricted to one dose. Thus, the administration can be in 1 to 50 doses, for example, 2 doses, 5 doses, 10 doses, 15 doses, 20 doses, 25 doses, 30 doses, 35 doses, 40 doses, 45 doses, or 50 doses, including all values and subranges that lie therebetween. Where there is more than one administration in the present methods, the administrations can be spaced by time intervals of about 1 minute to about 1 month, for example, about one minute, about two minutes, about three minutes, about four minutes, about five minutes, about six minutes, about seven minutes, about eight minutes, about nine minutes, about ten minutes, about 20 minutes, about 40 minutes, about one hour, about two hours, about three, about four, about five, about six, about seven, about eight, about nine, about ten, about 15, about 20, about 24 hours, about two days, about five days, about ten days, about 15 days, about 20 days, including all sub ranges and values that lie therebetween. The invention is not limited to dosing intervals that are spaced equally in time, but encompass doses at non-equal intervals, such as a priming schedule consisting of administration at 1 day, 4 days, 7 days, and 25 days, just to provide a non-limiting example.

A dosing schedule of, for example, once/week, twice/week, three times/week, four times/week, five times/week, six times/week, seven times/week, once every two weeks, once every three weeks, once every four weeks, once every five weeks, and the like, is available for the invention. The dosing schedules encompass dosing for a total period of time of about one day to about one year, for example, one week, two weeks, three weeks, four weeks, five weeks, six weeks, two months, three months, four months, five months, six months, seven months, eight months, nine months, ten months, eleven months, and twelve months, including all values and subranges that lie therebetween.

Provided are examples of cycles of the above dosing schedules. The cycle can be repeated about, e.g., every seven days; every 14 days; every 21 days; every 28 days; every 35 days; 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like.

The compositions disclosed herein may be administered with one or more additional therapeutic agents. Methods for co-administration with an additional therapeutic agent are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.).

Subjects to be treated herein include mammals, such as humans and non-human primates. In some embodiments, the subjects may be selected from humans, non-human primates, bovines, ovines, caprines, equines, felines, canines, and lagomorphs.

Methods of Reducing Neutralizing Antibodies Against a Biologic

The disclosure provides methods of reducing neutralizing antibodies against a recombinant biologic or a drug entity in a subject, comprising administering to the subject a therapeutically effective amount of the recombinant biologic or a drug entity, and any one of the compositions disclosed herein that (a) promotes the degradation of an antibody against the recombinant biologic or a drug entity; and/or (b) reduces the binding of the antibody to an Fc receptor.

In some embodiments, a method of reducing in a subject the amount of a neutralizing antibody against a recombinant adeno-associated virus (AAV) vector comprises administering to the subject a therapeutically effective amount of a composition that promotes the degradation of the neutralizing antibody.

In some embodiments, a method of preparing a subject for treatment with a recombinant adeno-associated virus (AAV) vector comprises administering to the subject a therapeutically effective amount of a composition that (a) promotes the degradation of a neutralizing antibody against the AAV vector, and/or (b) reduces the binding of the neutralizing antibody to an Fc receptor.

In some embodiments, a method of treating a subject in need thereof with a recombinant adeno-associated virus (AAV) vector comprises: (i) administering to the subject a therapeutically effective amount of a composition that (a) promotes the degradation of a neutralizing antibody against the AAV vector, and/or (b) reduces the binding of the neutralizing antibody to an Fc receptor; and (ii) administering to the subject a therapeutically effective amount of the AAV vector.

In some embodiments, a method of treating a subject with a second recombinant adeno-associated virus (AAV) vector, wherein the subject has previously been treated with a first recombinant AAV, comprises: (i) administering to the subject a therapeutically effective amount of a composition that (a) promotes the degradation of a neutralizing antibody against the first and/or the second recombinant AAV vector, and/or (b) reduces the binding of the neutralizing antibody to an Fc receptor; and (ii) administering to the subject a therapeutically effective amount of the second recombinant AAV vector.

In some embodiments, a method of reducing neutralizing antibodies against an adeno-associated virus (AAV) vector comprising a heterologous nucleic acid in a subject comprises administering to the subject a therapeutically effective amount of the AAV vector, and a composition that (a) promotes the degradation of an antibody against the AAV vector, or a recombinant protein encoded by the heterologous nucleic acid; and/or (b) reduces the binding of the antibody to an Fc receptor.

In some embodiments, a method of reducing neutralizing antibodies against any one of the adeno-associated virus (AAV) vectors disclosed herein in a subject comprises administering to the subject a therapeutically effective amount of the AAV vector, and any one of the compositions disclosed herein that (a) promotes the degradation of an antibody against the AAV vector, or a recombinant protein encoded by the heterologous nucleic acid; and/or (b) reduces the binding of the antibody to an Fc receptor.

The composition that (a) promotes the degradation of a neutralizing antibody against the first and/or the second recombinant AAV vector, and/or (b) reduces the binding of the neutralizing antibody to an Fc receptor may comprise an antibody-degrading enzyme or a fragment thereof. In some embodiments, the composition comprises a vector comprising a polynucleotide encoding an antibody-degrading enzyme or a fragment thereof. In some embodiments, the antibody-degrading enzyme, or the fragment thereof, may have cysteine protease activity. In some embodiments, the antibody-degrading enzyme specifically cleaves IgG. In some embodiments, the antibody-degrading enzyme, or the fragment thereof is derived from the genus *Streptococcus*. In some embodiments, the antibody-degrading enzyme comprises an amino acid sequence having at least 90% or at least 95% identity to the amino acid sequence of SEQ ID NO: 1. In some embodiments, the antibody-degrading enzyme comprises the amino acid sequence of SEQ ID NO: 1.

In some embodiments, the composition may comprise a fusion protein comprising a first protein and a second protein, wherein the first protein is an antibody-degrading enzyme or a fragment thereof. In some embodiments, the first protein and the second protein are separated by a linker. In some embodiments, the second protein is an IgG protease.

The composition may be administered via a systemic route (e.g., intravenously, intra-articularly or intra-lymphatically). In some embodiments, the composition is delivered locally (e.g., intramuscularly, intradermally, subcutaneously, topically). In some embodiments, the composition is administered directly to a location known to contain neutralizing antibodies, such as the cerebralspinal fluid (CSF). The compositions may comprise a pharmaceutically acceptable carrier and/or diluent.

In some embodiments, about 0.1 mg/kg to about 100 mg/kg of an antibody-degrading enzyme or fragment thereof are administered to the subject. In some embodiments, about 0.1 mg/kg to about 100 mg/kg of a fusion protein are administered to the subject. In some embodiments, about 0.05 mg/kg to about 150 mg/kg, of the antibody-degrading enzyme or fragment thereof, or fusion protein, is administered to the subject, for example, about 0.1 mg/kg, about 0.5 mg/kg, about 1 mg/kg, about 2 mg/kg, about 3 mg/kg, about 4 mg/kg, about 5 mg/kg, about 6 mg/kg, about 7 mg/kg, about 8 mg/kg, about 9 mg/kg, about 10 mg/kg, about 20 mg/kg, about 30 mg/kg, about 40 mg/kg, about 50 mg/kg, about 60 mg/kg, about 70 mg/kg, about 80 mg/kg, about 90 mg/kg, about 100 mg/kg, about 110 mg/kg, about 120 mg/kg, about 130 mg/kg, about 140 mg/kg, or about 150 mg/kg, including all values and subranges that lie therebetween.

In some embodiments, the neutralizing antibodies to be reduced and/or degraded comprise IgG, IgM, IgE, and/or IgA. In some embodiments, the neutralizing antibodies are comprise IgG. In some embodiments, the antibodies are neutralizing antibodies against AAV vectors comprising a transgene. In some embodiments, the antibodies bind to a recombinant protein encoded by the transgene. In some embodiments, the antibodies bind to adeno-associated viral capsid proteins or virions thereof.

In some embodiments, the recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector. In some embodiments, the recombinant AAV vector comprises a capsid protein having the sequence of any one of SEQ ID NO: 2-12, or a sequence at least 90%, at least 95%, at least 96%, at least 97%, at least 98%, or at least 99% identical thereto. In some embodiments, the AAV vector is a wildtype AAV vector. In some embodiments, the AAV vector is a mutant AAV vector. In some embodiments, the AAV vector is a wildtype AAV1 vector. In some embodiments, the AAV vector is a wildtype AAV2 vector. In some embodiments, the AAV vector is a wildtype AAV4 vector. In some embodiments, the AAV vector is a wildtype AAV8 vector. In some embodiments, the AAV vector is a wildtype AAV9 vector. In some embodiments, the AAV vector is a mutant AAV1 vector. In some embodiments, the AAV vector is a mutant AAV2 vector. In some embodiments, the AAV vector is a mutant AAV4 vector. In some embodiments, the AAV vector is a mutant AAV8 vector. In some embodiments, the AAV vector is a mutant AAV9 vector. In some embodiments, the recombinant AAV vector comprises a heterologous nucleic acid encoding a therapeutic protein or therapeutic RNA.

In some embodiments, the methods described herein comprise decreasing the interaction of the antibodies with their cognate receptors on cell surfaces. Such methods might expand the patient cohort eligible for gene therapy and also enable AAV re-dosing/re-administration in patients previously treated with AAV vectors.

In some embodiments of the methods of the disclosure, the subject is administered the AAV vector concurrently with the composition. In some embodiments, the subject is administered the AAV vector after the administration of the composition. In some embodiments, the subject is administered the AAV vector prior to the administration of the composition. In some embodiments, the method further comprises administering one or more additional or secondary doses of a second AAV vector comprising a second heterologous nucleic acid. In some embodiments, the first AAV vector and the second AAV vector comprise the same AAV capsid protein. In some embodiments, the first AAV vector and the second AAV vector comprise different AAV capsid proteins.

In some embodiments, the methods promote the degradation of the antibody against the AAV vector. In some embodiments, the level of the antibody is reduced to a level in the range of about 95% to about 0.01% (for example, about 90%, about 85%, about 80%, about 75%, about 70%, about 65%, about 60%, about 55%, about 50%, about 45%, about 40%, about 35%, about 30%, about 25%, about 20%, about 15%, about 10%, about 5%, about 1%, about 0.1%, or about 0.01%, including all the values and subranges that lie therebetween) of the level of the antibody in a control subject. As used herein, a control subject is a subject who is administered the recombinant biologic, such as an AAV vector, but is not administered any one of the compositions disclosed herein. In some embodiments, the methods result in at least 10%, at least 20%, at least 30%, at least 40%, at least 50%, at least 60%, at least 70%, at least 80%, at least 90%, or at least 99% of the antibody being degraded after the administration of the composition.

In some embodiments, the subject was previously administered a recombinant protein. Therefore, in some embodiments, the administration of any one of the compositions disclosed herein decreases circulating levels of antibodies generated against a prior dose of a recombinant protein in the subject.

Importantly, the compositions and method(s) according to the present disclosure can be used in conjunction with other pharmacological or interventional approaches that can reduce antibodies.

Recombinant Virus Vectors

In some embodiments, the vectors disclosed herein are useful for the delivery of the heterologous nucleic acid to cells in vitro, ex vivo, and in vivo. In some embodiments, the vector is a viral vector, for example, an AAV vector. In particular, the virus vectors can be advantageously employed to deliver or transfer nucleic acids to animal cells, for example, mammalian cells. In some embodiments, the viral vector comprises a recombinant viral capsid that envelopes the heterologous nucleic acid, for example, an AAV capsid. In some embodiments, the recombinant viral capsid comprises recombinant capsid proteins, for example recombinant AAV capsid proteins. Further details on the viral vectors, viral capsids and/or capsid proteins that may be used according to the present disclosure are provided in the International Applications PCT/US2019/025617, PCT/US2019/025584, and PCT/US2019/025610, the contents of each of which is incorporated herein by reference in their entireties for all purposes.

In some embodiments, the AAV vector comprises a capsid protein of an AAV serotype selected from AAV1, AAV2, AAV3, AAV3B, AAV4, AAV5, AAV6, AAV7, AAV8, AAV9, AAV10, AAV11, AAV12, AAVrh.8, AAVrh.10, AAVrh.32.33, AAVrh74, bovine AAV, avian AAV or any other AAV now known or later identified. In some embodiments, the AAV capsid protein is chimeric.

In some embodiments, the capsid proteins are AAV capsid proteins (VP1, VP2 and/or VP3) comprising a modification (e.g., a substitution) in the amino acid sequence and virus capsids and virus vectors comprising the modified AAV capsid protein. In some embodiments, the modifications described herein can confer one or more desirable properties to virus vectors comprising the modified AAV capsid protein including without limitation, the ability to evade neutralizing antibodies.

In some embodiments, the AAV capsid protein comprises one or more amino acid substitutions, wherein the one or more substitutions modify one or more antigenic sites on the AAV capsid protein. The modification of the one or more antigenic sites results in inhibition of binding by an antibody to the one or more antigenic sites and/or inhibition of neutralization of infectivity of a virus particle comprising said AAV capsid protein. In some embodiments, modification of the one or more antigenic sites results in inhibition of binding by an antibody to the one or more antigenic sites. In some embodiments, the modified antigenic site can prevent antibodies from binding or recognizing or neutralizing AAV capsids, wherein the antibody is an IgG (including IgG1, IgG2a, IgG2b, IgG3), IgM, IgE or IgA. In some embodiments, modification of the one or more antigenic sites results in neutralization of infectivity of a virus particle comprising the AAV capsid protein.

The one or more amino acid substitutions can be in one or more antigenic footprints identified by peptide epitope mapping and/or cryo-electron microscopy studies of AAV-antibody complexes containing AAV capsid proteins. In some embodiments, the one or more antigenic sites are common antigenic motifs or CAMs as described in WO 2017/058892, which is incorporated herein by reference in its entirety. In some embodiments, the antigenic sites are in a variable region (VR) of the AAV capsid protein, such as VR-I, VR-II, VR-III, VR-IV, VR-V, VR-VI, VR-VII, VR-VIII, VR-IX. In some embodiments, one or more antigenic sites is in the HI loop of the AAV capsid protein.

In some embodiments, the amino acid substitution replaces any six, seven, or eight amino acids in an AAV capsid protein from any one of the following serotypes: AAV1, AAV2, AAV3, AAV4, AAV5, AAV6, AAV7, AAV8, AAV9, AAVrh8, AAVrh10, AAV10, AAV11, AAV12, AAVrh32.22, bovine AAV, or Avian AAV. In some embodiments, the substitution introduces a deletion into the AAV capsid sequence. For example, a sequence of 6, 7, 8, or 9 amino acids are substituted to replace 7, 8, 9, or 10 amino acids, respectively, of a native amino acid capsid sequence. In some embodiments, the substitution introduces an insertion into the AAV capsid sequence. For example, a sequence of 6, 7, 8, or 9 amino acids are substituted to replace 5, 6, 7, or 8 amino acids, respectively, of a native amino acid capsid sequence.

In some embodiments, the one or more substitutions of the one or more antigenic sites can introduce one or more antigenic sites from a capsid protein of a first AAV serotype into the capsid protein of a second AAV serotype that is different from said first AAV serotype.

As used herein, "substitution" may refer to a single amino acid substitution, or a substitution of more than one amino acid. For example in some embodiments, a capsid protein of this disclosure can comprise at least 1, 2, 3, 4, 5, 6, 7, 8, 9, 10, etc., single amino acid substitutions. In some embodiments, a capsid protein of this disclosure can comprise one or more substitutions of multiple contiguous amino acids, such as one or more substitutions of 2, 3, 4, 5, 6, 7, 8, 9, 10, 11, or 12 contiguous amino acids.

Furthermore, in the embodiments described herein wherein an amino acid residue is substituted by any amino acid residue other than the amino acid residue present in the wild type or native amino acid sequence, the any other amino acid residue can be any natural or non-natural amino acid residue known in the art (see, e.g., Tables 3 and 4). In some embodiments, the substitution can be a conservative substitution and in some embodiments, the substitution can be a non-conservative substitution.

In some embodiments, the AAV capsid protein comprises a first amino acid substitution and a second amino acid substitution, wherein the first amino acid substitution and the second amino acid substitution each modify a different antigenic site on the AAV capsid protein. In some embodiments, the AAV capsid protein comprises a first acid substitution, a second amino acid substitution, and a third amino acid substitution, wherein the first amino acid substitution, the second amino acid substitution, and the third amino acid substitution each modify a different antigenic site on the AAV capsid protein.

Any one of the AAV capsids described herein may further comprise a modification (e.g., a substitution or a deletion) in the HI loop. The HI loop is a prominent domain on the AAV capsid surface, between β strands βH and βI, that extends from each viral protein (VP) subunit overlapping the neighboring fivefold VP. In some embodiments, an AAV capsid comprises one, two, three, four, five, six, seven, or eight amino acid substitutions in the HI loop. In some embodiments, an AAV capsid protein comprises one, two, three, or four amino acid substitutions, wherein each substitution modifies a different antigenic site on the AAV capsid protein, and wherein at least one of the amino acid substitutions modifies the HI loop of the capsid protein. In some embodiments, an AAV capsid protein comprises a first, a second, a third, and a fourth amino acid substitution.

In some embodiments, the AAV capsid proteins disclosed herein are encoded by, and expressed from a nucleotide sequence, or an expression vector comprising the same. The nucleotide sequence may be a DNA sequence or an RNA sequence.

In some embodiments, the modified capsid proteins are produced by modifying the capsid protein of any AAV now known or later discovered. Further, the AAV capsid protein that is to be modified can be a naturally occurring AAV capsid protein (e.g., an AAV2, AAV3a or 3b, AAV4, AAV5, AAV6, AAV7, AAV8, AAV9, AAV10 or AAV11 capsid protein or any of the AAV shown in Table 2) but is not so limited. Those skilled in the art will understand that a variety of manipulations to the AAV capsid proteins are known in the art and the disclosure is not limited to modifications of naturally occurring AAV capsid proteins. For example, the capsid protein to be modified may already have alterations as compared with naturally occurring AAV (e.g., is derived from a naturally occurring AAV capsid protein, e.g., AAV2, AAV3a, AAV3b, AAV4, AAV5, AAV6, AAV7, AAV8, AAV9, AAV10, AAV11, AAV12 or any other AAV now known or later discovered). In some embodiments, the capsid protein may be a chimeric capsid protein. In some embodiments, the capsid protein may be an engineered AAV, such as AAV2i8, AAV2g9, AAV-LK03, AAV7m8, AAV Anc80, AAV PHP.B. Such AAV capsid proteins are also within the scope of the present disclosure.

Thus, in some embodiments, the AAV capsid protein to be modified can be derived from a naturally occurring AAV but further comprises one or more foreign sequences (e.g., that are exogenous to the native virus) that are inserted and/or substituted into the capsid protein and/or has been altered by deletion of one or more amino acids. In some embodiments, the modifications to the AAV capsid protein are "selective" modifications. This approach is in contrast to previous work with whole subunit or large domain swaps between AAV serotypes (see, e.g., international patent publication WO 00/28004 and Hauck et al., (2003) J. Virology 77:2768-2774). In particular embodiments, a "selective" modification results in the insertion and/or substitution and/or deletion of less than or equal to about 20, about 18, about 15, about 12, about 10, about 9, about 8, about 7, about 6, about 5, about 4 or about 3 contiguous amino acids. The modified capsid proteins and capsids of the disclosure can further comprise any other modification, now known or later identified.

Accordingly, when referring herein to a specific AAV capsid protein (e.g., an AAV2, AAV3, AAV4, AAV5, AAV6, AAV7, AAV8, AAV9, AAV10 or AAV11 capsid protein or a capsid protein from any of the AAV shown in Table 2, etc.), it is intended to encompass the native capsid protein as well as capsid proteins that have alterations other than the modifications of the disclosure. Such alterations include substitutions, insertions and/or deletions. In particular embodiments, the capsid protein comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids inserted therein (other than the insertions of the present disclosure) as compared with the native AAV capsid protein sequence. In embodiments, the capsid protein comprises 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acid substitutions (other than the amino acid substitutions according to the present disclosure) as compared with the native AAV capsid protein sequence, in embodiments of the disclosure, the capsid protein comprises a deletion of 1, 2, 3, 4, 5, 6, 7, 8, 9, 10, 11, 12, 13, 14, 15, 16, 17, 18, 19 or 20, less than 20, less than 30, less than 40, less than 50, less than 60, or less than 70 amino acids (other than the amino acid deletions of the disclosure) as compared with the native AAV capsid protein sequence.

Methods of determining sequence similarity or identity between two or more amino acid sequences are known in the art. Sequence similarity or identity may be determined using standard techniques known in the art, including, but not limited to, the local sequence identity algorithm of Smith & Waterman, Adv. Appl. Math. 2, 482 (1981), by the sequence identity alignment algorithm of Needleman & Wunsch, J Mol. Biol. 48,443 (1970), by the search for similarity method of Pearson & Lipman, Proc. Natl. Acad. Sci. USA 85, 2444 (1988), by computerized implementations of these algorithms (GAP, BESTFIT, FASTA, and TFASTA in the Wisconsin Genetics Software Package, Genetics Computer Group, 575 Science Drive, Madison, WI), the Best Fit sequence program described by Devereux et al., Nucl. Acid Res. 12, 387-395 (1984), or by inspection.

Another suitable algorithm is the BLAST algorithm, described in Altschul et al., J Mol. Biol. 215, 403-410, (1990) and Karlin et al., Proc. Natl. Acad. Sci. USA 90, 5873-5787 (1993). A particularly useful BLAST program is the WU-BLAST-2 program which was obtained from Altschul et al., Methods in Enzymology, 266, 460-480 (1996); http://blast.wustl/edu/blast/README.html. WU-BLAST-2 uses several search parameters, which are optionally set to the default values. The parameters are dynamic values and are established by the program itself depending upon the composition of the particular sequence and composition of the particular database against which the sequence of interest is being searched; however, the values may be adjusted to increase sensitivity.

Further, an additional useful algorithm is gapped BLAST as reported by Altschul et al, (1997) Nucleic Acids Res. 25, 3389-3402.

In some embodiments, an AAV vector comprises an AAV capsid and an AAV genome, and has a phenotype of evading neutralizing antibodies. In addition, the AAV virus particle or vector disclosed herein can also have a phenotype of enhanced or maintained transduction efficiency in addition to the phenotype of evading neutralizing antibodies.

Virus vectors according to the disclosure can be produced using any method known in the art, e.g., by expression using a baculovirus system.

In some embodiments of this disclosure, the virus capsid can be a targeted virus capsid, comprising a targeting sequence (e.g., substituted or inserted in the viral capsid) that directs the virus capsid to interact with cell-surface molecules present on desired target tissue(s). For example, a virus capsid of this disclosure may have relatively inefficient tropism toward certain target tissues of interest (e.g., liver, skeletal muscle, heart, diaphragm muscle, kidney, brain, stomach, intestines, skin, endothelial cells, and/or lungs). A targeting sequence can advantageously be incorporated into these low-transduction vectors to thereby confer to the virus capsid a desired tropism and, optionally, selective tropism for particular tissue(s). AAV capsid proteins, capsids and vectors comprising targeting sequences are described, for example in international patent publication WO 00/28004. As another example, one or more non-naturally occurring amino acids as described by Wang et al., Annu Rev Biophys Biomol Struct. 35:225-49 (2006)) can be incorporated into an AAV capsid subunit of this disclosure at an orthogonal site as a means of redirecting a low-transduction vector to desired target tissue(s). These unnatural amino acids can advantageously be used to chemically link molecules of interest to the AAV capsid protein including without limitation: glycans (mannose-dendritic cell targeting); RGD, bombesin or a neuropeptide for targeted delivery to specific cancer cell types; RNA aptamers or peptides selected from phage display targeted to specific cell surface receptors such as growth factor receptors, integrins, and the like. Methods of chemically modifying amino acids are known in the art.

In some embodiments of this disclosure, the capsid protein, virus capsid or vector of this disclosure may have equivalent or enhanced transduction efficiency relative to the transduction efficiency of the AAV serotype from which the capsid protein, virus capsid or vector of this disclosure originated. In some embodiments of this disclosure, the capsid protein, virus capsid or vector of this disclosure may have reduced transduction efficiency relative to the transduction efficiency of the AAV serotype from which the capsid protein, virus capsid or vector of this disclosure originated. In some embodiments of this disclosure, the capsid protein, virus capsid or vector of this disclosure may have equivalent or enhanced tropism relative to the tropism of the AAV serotype from which the capsid protein, virus capsid or vector of this disclosure originated. In some embodiments of this disclosure, the capsid protein, virus capsid or vector of this disclosure may have an altered or different tropism relative to the tropism of the AAV serotype from which the capsid protein, virus capsid or vector of this disclosure originated. In some embodiments of this disclosure, the capsid protein, virus capsid or vector of this disclosure may have or be engineered to have tropism for brain tissue. In some embodiments of this disclosure, the capsid protein, virus capsid or vector of this disclosure may have or be engineered to have tropism for liver tissue.

Those skilled in the art will appreciate that for some AAV capsid proteins the corresponding modification will be an insertion and/or a substitution, depending on whether the corresponding amino acid positions are partially or completely present in the virus or, alternatively, are completely absent. As discussed elsewhere herein, the corresponding amino acid position(s) will be readily apparent to those skilled in the art using well-known techniques.

AAV Virus Vectors

In some embodiments, the virus vector comprises a modified AAV capsid comprising a modified capsid subunit of the disclosure and a vector genome. For example, in some embodiments, the virus vector comprises: (a) a modified virus capsid (e.g., a modified AAV capsid) comprising a modified capsid protein of the disclosure; and (b) a heterologous nucleic acid comprising a terminal repeat sequence (e.g., an AAV TR), wherein the heterologous nucleic acid comprising the terminal repeat sequence is encapsidated by the modified virus capsid. The nucleic acid can optionally comprise two terminal repeats (e.g., two AAV TRs).

In some embodiments, the virus vectors of the disclosure (i) have reduced transduction of liver as compared with the level of transduction by a virus vector without the modified capsid protein; (ii) exhibit enhanced systemic transduction by the virus vector in an animal subject as compared with the level observed by a virus vector without the modified capsid protein; (iii) demonstrate enhanced movement across endothelial cells as compared with the level of movement by a virus vector without the modified capsid protein, and/or (iv) exhibit a selective enhancement in transduction of muscle tissue (e.g., skeletal muscle, cardiac muscle and/or diaphragm muscle), (v) exhibit a selective enhancement in transduction of liver tissue, and/or (vi) reduced transduction of brain tissues (e.g., neurons) as compared with the level of transduction by a virus vector without the modified capsid protein. In particular embodiments, the virus vector has systemic transduction toward liver.

In some embodiments, the virus vector is a recombinant virus vector comprising a heterologous nucleic acid encoding a polypeptide or functional RNA of interest. In some embodiments, the nucleic acid is a nucleic acid encoding a polypeptide, including therapeutic (e.g., for medical or veterinary uses) or immunogenic (e.g., for vaccines) polypeptide or RNA.

Alternatively, the immunogenic polypeptide can be any tumor or cancer cell antigen. Optionally, the tumor or cancer antigen is expressed on the surface of the cancer cell.

It will be understood by those skilled in the art that the heterologous nucleic acid can be operably associated with appropriate control sequences. For example, the heterologous nucleic acid can be operably associated with expression control elements, such as transcription/translation control signals, origins of replication, polyadenylation signals, internal ribosome entry sites (IRES), promoters, and/or enhancers, and the like. Further, regulated expression of the heterologous nucleic acid(s) of interest can be achieved at the post-transcriptional level, e.g., by regulating selective splicing of different introns by the presence or absence of an oligonucleotide, small molecule and/or other compound that selectively blocks splicing activity at specific sites.

Those skilled in the art will appreciate that a variety of promoter/enhancer elements can be used depending on the level and tissue-specific expression desired. The promoter/enhancer can be constitutive or inducible, depending on the pattern of expression desired. The promoter/enhancer can be native or foreign and can be a natural or a synthetic sequence. By foreign, it is intended that the transcriptional initiation region is not found in the wild-type host into which the transcriptional initiation region is introduced.

In particular embodiments, the promoter/enhancer elements can be native to the target cell or subject to be treated. In representative embodiments, the promoters/enhancer element can be native to the heterologous nucleic acid sequence. The promoter/enhancer element is generally chosen so that it functions in the target cell(s) of interest. Further, in particular embodiments the promoter/enhancer element is a mammalian promoter/enhancer element. The promoter/enhancer element may be constitutive or inducible.

Inducible expression control elements are typically advantageous in those applications in which it is desirable to provide regulation over expression of the heterologous nucleic acid sequence(s). Inducible promoters/enhancer elements for gene delivery can be tissue-specific or -preferred promoter/enhancer elements, and include muscle specific or preferred (including cardiac, skeletal and/or smooth muscle specific or preferred), neural tissue specific or preferred (including brain-specific or preferred), eye specific or preferred (including retina-specific and cornea-specific), liver specific or preferred, bone marrow specific or preferred, pancreatic specific or preferred, spleen specific or preferred, and lung specific or preferred promoter/enhancer elements. Other inducible promoter/enhancer elements include hormone-inducible and metal-inducible elements. Exemplary inducible promoters/enhancer elements include, but are not limited to, a Tet on/off element, a RU486-inducible promoter, an ecdysone-inducible promoter, a rapamycin-inducible promoter, and a metallothionein promoter.

The virus vectors according to the present disclosure provide a means for delivering heterologous nucleic acids into a broad range of cells, including dividing and non-dividing cells. The virus vectors can be employed to deliver a nucleic acid of interest to a cell in vitro, e.g., to produce a polypeptide in vitro or for ex vivo gene therapy. The virus vectors are additionally useful in a method of delivering a nucleic acid to a subject in need thereof e.g., to express an immunogenic or therapeutic polypeptide or a functional RNA. In this manner, the polypeptide or functional RNA can be produced in vivo in the subject. The subject can be in need of the polypeptide because the subject has a deficiency of the polypeptide. Further, the method can be practiced because the production of the polypeptide or functional RNA in the subject may impart some beneficial effect.

The virus vectors of the present disclosure can be employed to deliver a heterologous nucleic acid encoding a polypeptide or functional RNA to treat and/or prevent any disease state for which it is beneficial to deliver a therapeutic polypeptide or functional RNA. Gene transfer has substantial use for understanding and providing therapy for disease states. There are a number of inherited diseases in which defective genes are known and have been cloned. In general, the above disease states fall into two classes: deficiency states, usually of enzymes, which are generally inherited in a recessive manner, and unbalanced states, which may involve regulatory or structural proteins, and which are typically inherited in a dominant manner. For deficiency state diseases, gene transfer can be used to bring a normal gene into affected tissues for replacement therapy, as well as to create animal models for the disease using antisense mutations. For unbalanced disease states, gene transfer can be used to create a disease state in a model system, which can then be used in efforts to counteract the disease state. Thus, virus vectors according to the present disclosure permit the treatment and/or prevention of genetic diseases.

The virus vectors according to the present disclosure may also be employed to provide a functional RNA to a cell in vitro or in vivo. The functional RNA may be, for example, a non-coding RNA. In some embodiments, expression of the functional RNA in the cell can diminish expression of a particular target protein by the cell. Accordingly, functional RNA can be administered to decrease expression of a particular protein in a subject in need thereof. In some embodiments, expression of the functional RNA in the cell can increase expression of a particular target protein by the cell. Accordingly, functional RNA can be administered to increase expression of a particular protein in a subject in need thereof. In some embodiments, expression of the functional RNA can regulate splicing of a particular target RNA in a cell. Accordingly, functional RNA can be administered to regulate splicing of a particular RNA in a subject in need thereof. In some embodiments, expression of the functional RNA in the cell can regulate the function of a particular target protein by the cell. Accordingly, functional RNA can be administered to regulate the function of a particular protein in a subject in need thereof. Functional RNA can also be administered to cells in vitro to regulate gene expression and/or cell physiology, e.g., to optimize cell or tissue culture systems or in screening methods.

Alternatively, the virus vector may be administered to a cell ex vivo and the altered cell is administered to the subject. The virus vector comprising the heterologous nucleic acid is introduced into the cell, and the cell is administered to the subject, where the heterologous nucleic acid encoding the immunogen can be expressed and induce an immune response in the subject against the immunogen. In particular embodiments, the cell is an antigen-presenting cell (e.g., a dendritic cell).

Kits

Another aspect of the present disclosure provides a kit for the reduction and/or elimination of neutralizing antibodies and/or immunoglobulins against a recombinant biologic and/or drug entity in a subject, the kit comprising, consisting of, or consisting essentially of any one of the compositions described herein, means of administering the composition, and instructions for use. In some embodiments, the reagent comprises an immunoglobulin G (IgG)-degrading enzyme.

Numbered Embodiments

The following numbered embodiments are included within the scope of the disclosure.

1. A method for reducing, in a subject in need thereof, the amount of a neutralizing antibody against a recombinant adeno-associated virus (AAV) vector, the method comprising administering to the subject a therapeutically effective amount of a composition that promotes the degradation of the neutralizing antibody.

2. The method of embodiment 1, wherein the neutralizing antibody is an IgG, IgM, IgE, or IgA.

3. The method of embodiment 2, wherein the neutralizing antibody is an IgG.

4. The method of any one of embodiments 1-3, wherein the recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector.

5. The method of embodiment 4, wherein the AAV vector is a wildtype AAV vector.

6. The method of embodiment 4, wherein the AAV vector is a mutant AAV vector.

7. The method of any one of embodiments 1-6, wherein the recombinant AAV vector comprises a heterologous nucleic acid encoding a therapeutic protein or therapeutic RNA.

8. The method of any one of embodiments 1-7, wherein at least 10%, at least 20%, at least 30%, at least 40%, at least 50%, at least 60%, at least 70%, at least 80%, at least 90%, or at least 99% of the antibody in the subject is degraded after administration of the composition.

9. The method of any one of embodiments 1-8, wherein the composition comprises an antibody-degrading enzyme or a fragment thereof.

10. The method of any one of embodiments 1-8, wherein the composition comprises a vector comprising a polynucleotide encoding an antibody-degrading enzyme or a fragment thereof.

11. The method of embodiment 9 or 10, wherein the antibody-degrading enzyme, or the fragment thereof has cysteine protease activity.

12. The method of any one of embodiments 9-11, wherein the antibody-degrading enzyme specifically cleaves IgG.

13. The method of any one of embodiments 9-12, wherein the antibody-degrading enzyme, or the fragment thereof is derived from the genus *Streptococcus*.

14. The method of any one of embodiments 9-13, wherein the antibody-degrading enzyme comprises an amino acid sequence having at least 90% or at least 95% identity to the amino acid sequence of SEQ ID NO: 1.

15. The method of embodiment 14, wherein the antibody-degrading enzyme comprises the amino acid sequence of SEQ ID NO: 1.

16. The method of any one of embodiments 1-15, wherein the composition comprises a fusion protein comprising a first protein and a second protein, wherein the first protein is an antibody-degrading enzyme or a fragment thereof.

17. The method of embodiment 16, wherein the first protein and the second protein are separated by a linker.

18. The method of embodiment 16 or 17, wherein the second protein is an IgG protease.

19. The method of any one of embodiments 9-15, wherein about 0.1 mg/kg to about 100 mg/kg of the antibody-degrading enzyme or the fragment thereof is administered to the subject.

20. The method of any one of any one of embodiments 1-19, wherein the administering reduces the binding of the antibody to an Fc receptor.

21. The method of any one of embodiments 1-20, wherein the composition is administered intravenously.

22. The method of any one of embodiments 1-21, wherein the composition comprises a pharmaceutically acceptable carrier and/or diluent.

23. The method of any one of embodiments 1-22, wherein the subject is a human.

24. The method of any one of embodiments 1-23, wherein the subject is treated with the recombinant adeno-associated virus (AAV) vector before administration of the composition.

25. The method of any one of embodiments 1-23, wherein the subject is not treated with the recombinant AAV before administration of the composition.

26. A method for preparing a subject for treatment with a recombinant adeno-associated virus (AAV) vector, the method comprising administering to the subject an effective amount of a composition that (a) promotes the degradation of a neutralizing antibody against the AAV vector, and/or (b) reduces the binding of the neutralizing antibody to an Fc receptor.

27. The method of embodiment 26, wherein the neutralizing antibody is an IgG, IgM, IgE, or IgA.

28. The method of embodiment 27, wherein the neutralizing antibody is an IgG.

29. The method of any one of embodiments 26-28, wherein the recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector.

30. The method of embodiment 29, wherein the AAV vector is a wildtype AAV vector.

31. The method of embodiment 29, wherein the AAV vector is a mutant AAV vector.

32. The method of any one of embodiments 26-31, wherein the recombinant AAV comprises a heterologous nucleic acid encoding a therapeutic protein or therapeutic RNA.

33. The method of any one of embodiments 26-32, wherein at least 10%, at least 20%, at least 30%, at least 40%, at least 50%, at least 60%, at least 70%, at least 80%, at least 90%, or at least 99% of the antibody is degraded in the subject after the administration of the composition.

34. The method of any one of embodiments 26-33, wherein the composition comprises an antibody-degrading enzyme or a fragment thereof.

35. The method of any one of embodiments 26-33, wherein the composition comprises a vector comprising a polynucleotide encoding an antibody-degrading enzyme or a fragment thereof.

36. The method of embodiment 34 or 35, wherein the antibody-degrading enzyme, or the fragment thereof has cysteine protease activity.

37. The method of any one of embodiments 26-36, wherein the antibody-degrading enzyme specifically cleaves IgG.

38. The method of any one of embodiments 26-37, wherein the antibody-degrading enzyme, or the fragment thereof is derived from the genus *Streptococcus.*

39. The method of any one of embodiments 26-38, wherein the antibody-degrading enzyme comprises an amino acid sequence having at least 90% or at least 95% identity to the amino acid sequence of SEQ ID NO: 1.

40. The method of embodiment 39, wherein the antibody-degrading enzyme comprises the amino acid sequence of SEQ ID NO: 1.

41. The method of any one of embodiments 26-40, wherein the composition comprises a fusion protein comprising a first protein and a second protein, wherein the first protein is an antibody-degrading enzyme or a fragment thereof.

42. The method of embodiment 41, wherein the first protein and the second protein are separated by a linker.

43. The method of embodiment 41 or 42, wherein the second protein is an IgG protease.

44. The method of any one of embodiments 34-43, wherein about 0.1 mg/kg to about 100 mg/kg of the antibody-degrading enzyme or the fragment thereof is administered to the subject.

45. The method of any one of embodiments 28-44, wherein the administering reduces the binding of the antibody to an Fc receptor.

46. The method of any one of embodiments 26-45, wherein the composition is administered intravenously.

47. The method of any one of embodiments 26-46, wherein the composition comprises a pharmaceutically acceptable carrier and/or diluent.

48. The method of any one of embodiments 26-47, wherein the subj ect is a human.

49. A method of treating a subject in need thereof with a recombinant adeno-associated virus (AAV) vector the method comprising:

(i) administering to the subject an effective amount of a composition that (a) promotes the degradation of a neutralizing antibody against the AAV vector, and/or (b) reduces the binding of the neutralizing antibody to an Fc receptor; and (ii) administering to the subject an effective amount of the AAV vector.

50. The method of embodiment 49, wherein AAV vector is administered concurrently with the composition.

51. The method of embodiment 49, wherein the AAV vector is administered after the administration of the composition.

52. The method of embodiment 49, wherein the AAV vector is administered prior to the administration of the composition.

53. The method of any one of embodiments 49-52, wherein the method further comprises administering to the subject a second AAV vector.

54. The method of embodiment 53, wherein the AAV vector and the second AAV vector comprise AAV capsid proteins having the same serotype.

55. The method of embodiment 53, wherein the AAV vector and the second AAV vector comprise AAV capsid proteins having different serotypes.

56. The method of any one of embodiments 45-55, wherein the neutralizing antibody is an IgG, IgM, IgE, or IgA.

57. The method of embodiment 56, wherein the neutralizing antibody is an IgG.

58. The method of any one of embodiments 49-57, wherein the recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector.

59. The method of embodiment 58, wherein the AAV vector is a wildtype AAV vector.

60. The method of embodiment 58, wherein the AAV vector is a mutant AAV vector.

61. The method of any one of embodiments 49-60, wherein the recombinant AAV vector comprises a heterologous nucleic acid encoding a therapeutic protein or therapeutic RNA.

62. The method of any one of embodiments 49-61, wherein at least 10%, at least 20%, at least 30%, at least 40%, at least 50%, at least 60%, at least 70%, at least 80%, at least 90%, or at least 99% of the antibody is degraded after the administration of the composition.

63. The method of any one of embodiments 49-62, wherein the composition comprises an antibody-degrading enzyme or a fragment thereof.

64. The method of any one of embodiments 49-62, wherein the composition comprises a vector comprising a polynucleotide encoding an antibody-degrading enzyme or a fragment thereof.

65. The method of embodiment 63 or 64, wherein the antibody-degrading enzyme, or the fragment thereof has cysteine protease activity.

66. The method of any one of embodiments 63-65, wherein the antibody-degrading enzyme specifically cleaves IgG.

67. The method of any one of embodiments 63-66, wherein the antibody-degrading enzyme, or the fragment thereof is derived from the genus *Streptococcus.*

68. The method of any one of embodiments 63-67, wherein the antibody-degrading enzyme comprises an amino acid sequence having at least 90% or at least 95% identity to the amino acid sequence of SEQ ID NO: 1.

69. The method of embodiment 68, wherein the antibody-degrading enzyme comprises the amino acid sequence of SEQ ID NO: 1.

70. The method of any one of embodiments 49-69, wherein the composition comprises a fusion protein comprising a first protein and a second protein, wherein the first protein is an antibody-degrading enzyme or a fragment thereof.

71. The method of embodiment 70, wherein the first protein and the second protein are separated by a linker.

72. The method of embodiment 70 or 71, wherein the second protein is an IgG protease.

73. The method of any one of embodiments 63-72, wherein about 0.1 mg/kg to about 100 mg/kg of the antibody-degrading enzyme or the fragment thereof is administered to the subject.

74. The method of any one of embodiments 49-73, wherein the administering reduces the binding of the antibody to an Fc receptor.

75. The method of any one of embodiments 49-74, wherein the composition is administered intravenously.

76. The method of any one of embodiments 49-75, wherein the composition comprises a pharmaceutically acceptable carrier and/or diluent.

77. The method of any one of embodiments 49-76, wherein the subject is a human.

78. A method of treating a subject in need thereof with a second recombinant adeno-associated virus (AAV) vector, wherein the subject has previously been treated with a first recombinant AAV, the method comprising:
(i) administering to the subject an effective amount of a composition that (a) promotes the degradation of a neutralizing antibody against the first and/or the second recombinant AAV vector, and/or (b) reduces the binding of the neutralizing antibody to an Fc receptor; and
(ii) administering to the subject an effective amount of the second recombinant AAV vector.

79. The method of embodiment 78, wherein the first recombinant AAV and the second recombinant AAV have the same serotype.

80. The method of embodiment 78, wherein the first recombinant AAV and the second recombinant AAV have different serotypes.

81. The method of any one of embodiments 78-80, wherein the neutralizing antibody is an IgG, IgM, IgE, or IgA.

82. The method of embodiment 81, wherein the neutralizing antibody is an IgG.

83. The method of any one of embodiments 76-82, wherein the recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector.

84. The method of embodiment 83, wherein the AAV vector is a wiltdype AAV vector.

85. The method of embodiment 83, wherein the AAV vector is a mutant AAV vector.

86. The method of any one of embodiments 78-85, wherein the recombinant AAV comprises a heterologous nucleic acid encoding a therapeutic protein or therapeutic RNA.

87. The method of any one of embodiments 78-86, wherein at least 10%, at least 20%, at least 30%, at least 40%, at least 50%, at least 60%, at least 70%, at least 80%, at least 90%, or at least 99% of the antibody is degraded after administration of the composition.

88. The method of any one of embodiments 78-87, wherein the composition comprises an antibody-degrading enzyme or a fragment thereof.

89. The method of any one of embodiments 78-87, wherein the composition comprises a vector comprising a polynucleotide encoding an antibody-degrading enzyme or a fragment thereof.

90. The method of embodiment 88 or 89, wherein the antibody-degrading enzyme, or the fragment thereof has cysteine protease activity.

91. The method of any one of embodiments 78-90, wherein the antibody-degrading enzyme specifically cleaves IgG.

92. The method of any one of embodiments 78-91, wherein the antibody-degrading enzyme, or the fragment thereof is derived from the genus *Streptococcus.*

93. The method of any one of embodiments 78-92, wherein the antibody-degrading enzyme comprises an amino acid sequence having at least 90% or at least 95% identity to the amino acid sequence of SEQ ID NO: 1.

94. The method of embodiment 93, wherein the antibody-degrading enzyme comprises the amino acid sequence of SEQ ID NO: 1.

95. The method of any one of embodiments 87-94, wherein the composition comprises a fusion protein comprising a first protein and a second protein, wherein the first protein is an antibody-degrading enzyme or a fragment thereof.

96. The method of embodiment 95, wherein the first protein and the second protein are separated by a linker.

97. The method of embodiment 95 or 96, wherein the second protein is an IgG protease.

98. The method of any one of embodiments 78-97, wherein about 0.1 mg/kg to about 100 mg/kg of the antibody-degrading enzyme or the fragment thereof is administered to the subject.

99. The method of any one of embodiments 78-98, wherein the administering reduces the binding of the antibody to an Fc receptor.

100. The method of any one of embodiments 78-99, wherein the composition is administered intravenously.

101. The method of any one of embodiments 78-100, wherein the composition comprises a pharmaceutically acceptable carrier and/or diluent.

102. The method of any one of embodiments 78-101, wherein the subject is a human.

103. A method of reducing neutralizing antibodies against an adeno-associated virus (AAV) vector comprising a heterologous nucleic acid in a subject in need thereof, comprising administering to the subject an effective amount of the AAV vector, and a composition that (a) promotes the degradation of an antibody against the AAV vector, or a recombinant protein encoded by the heterologous nucleic acid; and/or (b) reduces the binding of the antibody to an Fc receptor.

104. The method of embodiment 103, wherein the antibody is an IgG.

105. The method of embodiment 103 or embodiment 104, wherein the subject is administered the AAV vector concurrently with the composition.

106. The method of embodiment 103 or embodiment 104, wherein the subject is administered the AAV vector after the administration of the composition.

107. The method of embodiment 103 or embodiment 104, wherein the subject is administered the AAV vector prior to the administration of the composition.

108. The method of embodiment 107, further comprising administering one or more doses of a second AAV vector comprising a second heterologous nucleic acid.

109. The method of embodiment 108, wherein the AAV vector and the second AAV vector comprise AAV capsid proteins having the same serotype.

110. The method of embodiment 108, wherein the AAV vector and the second AAV vector comprise AAV capsid proteins having different serotypes.

111. The method of any one of embodiments 102-110, wherein the composition further comprises a pharmaceutically acceptable carrier and/or diluent.

112. The method of any one of embodiments 102-111, wherein the composition promotes the degradation of the antibody.

113. The method of embodiment 112, wherein the level of the antibody in the subject is reduced to a level in the range of about 95% to about 0.01% relative to the level of the antibody in a control subject, wherein the control subject is administered the AAV vector, but not the composition.

114. The method of embodiment 112 or embodiment 113, wherein the composition comprises an antibody-degrading enzyme, or a fragment thereof.

115. The method of embodiment 112 or embodiment 113, wherein the composition comprises a vector comprising a polynucleotide encoding an antibody-degrading enzyme, or a fragment thereof.

116. The method of embodiment 114 or embodiment 115, wherein the antibody-degrading enzyme, or the fragment thereof comprises IgG cysteine protease activity.

117. The method of any one of embodiments 114-116, wherein the antibody-degrading enzyme, or the fragment thereof is derived from the genus *Streptococcus*.

118. The method of any one of embodiments 114-117, wherein the antibody-degrading enzyme comprises an amino acid sequence of at least 50% identity to the amino acid sequence of SEQ ID NO: 1.

119. The method of any one of embodiments 114-118, wherein the antibody-degrading enzyme comprises the amino acid sequence of SEQ ID NO: 1.

120. The method of any one of embodiments 114-119, wherein the composition comprises a fusion protein comprising the antibody-degrading enzyme, or a fragment thereof; and a second protein.

121. The method of embodiment 120, wherein the second protein is an IgG protease.

122. The method of any one of embodiments 114-121, wherein the subject is administered about 0.1 mg/kg to about 100 mg/kg of the antibody-degrading enzyme, or the fragment thereof.

123. The method of any one of embodiments 108-122, wherein the subject is a human.

124. The method of embodiment 102, wherein the composition reduces the binding of the antibody to an Fc receptor.

It is to be understood that the description above as well as the examples that follow are intended to illustrate, and not limit, the scope of the invention. Other aspects, advantages and modifications within the scope of the invention will be apparent to those skilled in the art to which the invention pertains.

EXAMPLES

Example 1: Cloning, Expression and Purification of Recombinant IdeZ (rIdeZ)

Figure 1B:
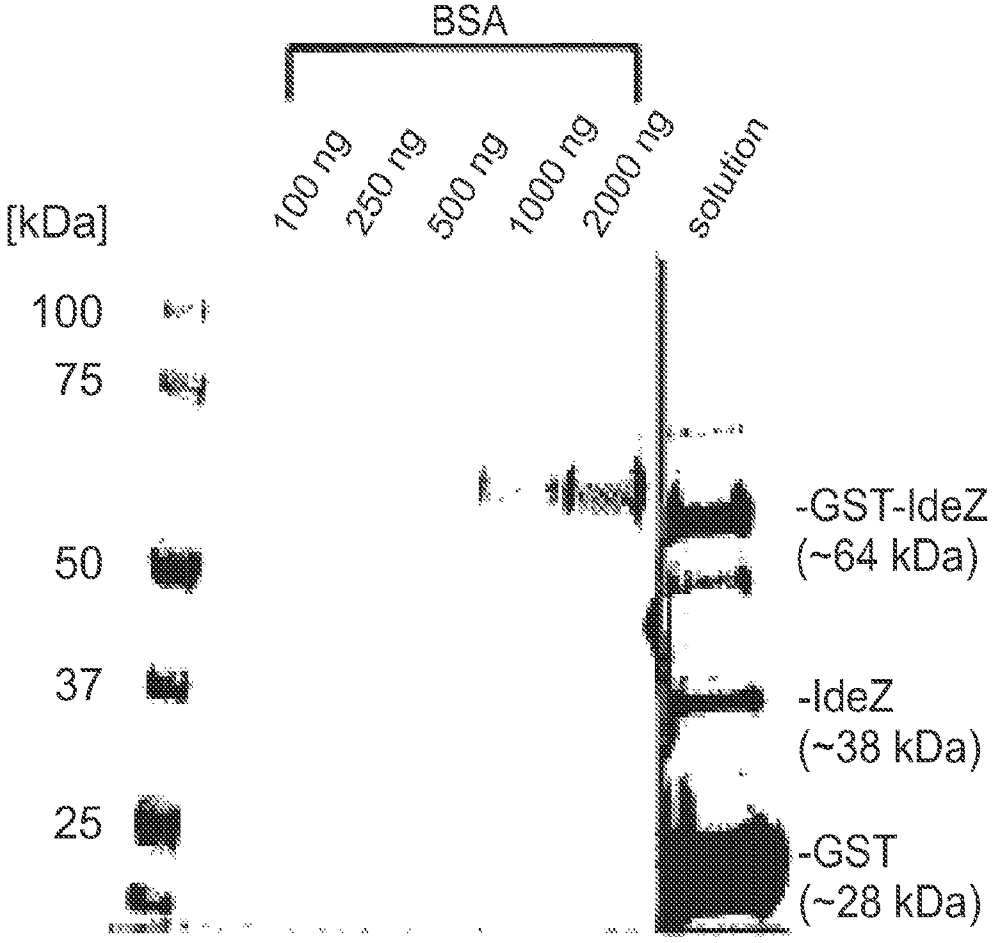

The IdeZ coding sequence was cloned into a pGEX-6P-3 vector using BamHI and SalI restriction sites to create an N-terminally GST tagged IdeZ fusion (GST-IdeZ) (FIG. 1A). The expression of GST-IdeZ was controlled under the lac operon and production was induced by addition of IPTG. IdeZ protein was purified using glutathione sepharose and eluted with excess glutathione. SDS-PAGE was used to monitor expression and purification (FIG. 1B). Recombinant IdeZ was quantified using Biorad Imagelab™ software using BSA as a standard.

Figure 6:
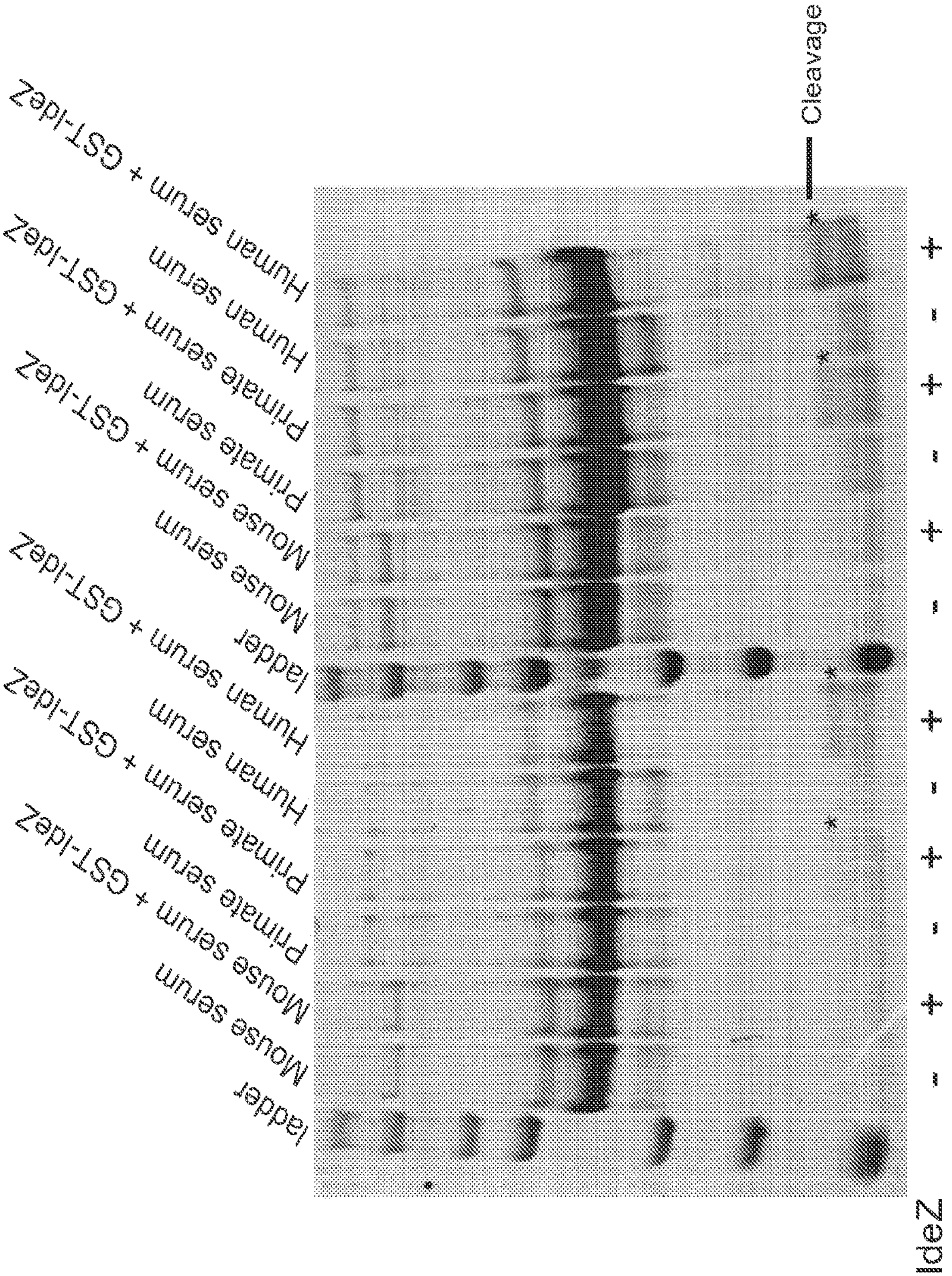
FIG. 6.

Example 2: IdeZ Cleaves Recombinant Mouse IgG and Serum IgG from Multiple Species To determine whether rIdeZ is active in vitro, mouse, primate, and human serum samples were treated with recombinant GST-IdeZ (1 μg) for 3 hours at 37° C. As shown in FIG. 6, GST-IdeZ cleaved IgG present within human and primate serum.

Figure 2B:
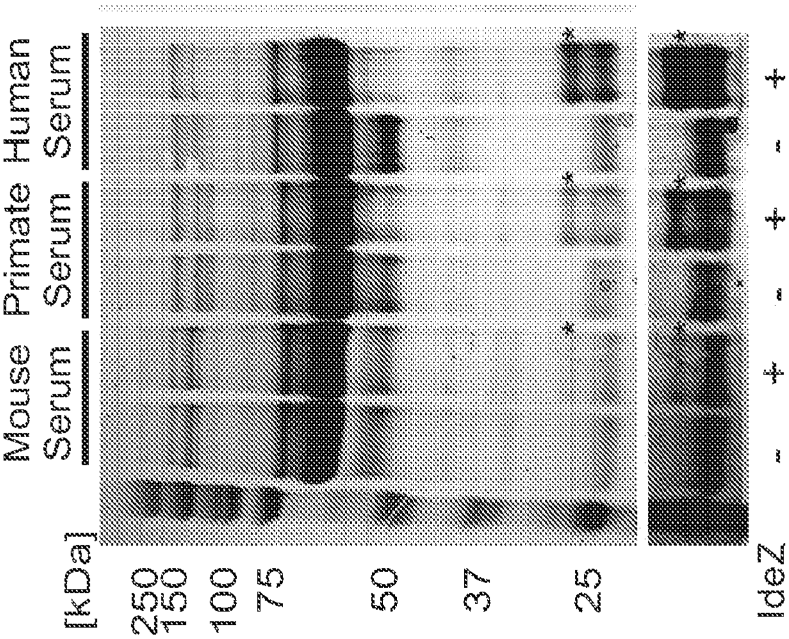
FIG. 2A-2D. Provided in FIG. 2A is an image of a Coomassie stained SDS-PAGE gel showing banding patterns for recombinant IgG samples untreated (−) or treated (+) with recombinant IdeZ.
Figure 2A:
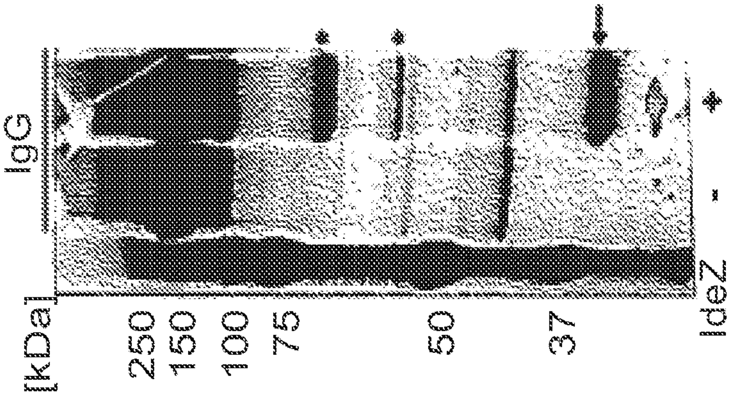

In a separate experiment, recombinant mouse IgG (40 μg) was incubated with rIdeZ (NEB P0770S, 160 units) for 2 hours at 37° C. Reactions were analyzed by SDS-PAGE under non-reducing conditions and stained with Coomassie blue (FIG. 2A). In the presence of IdeZ, recombinant mouse IgG was cleaved into multiple bands as indicated with asterisks. Arrow indicates IdeZ protein.

Figure 2C:
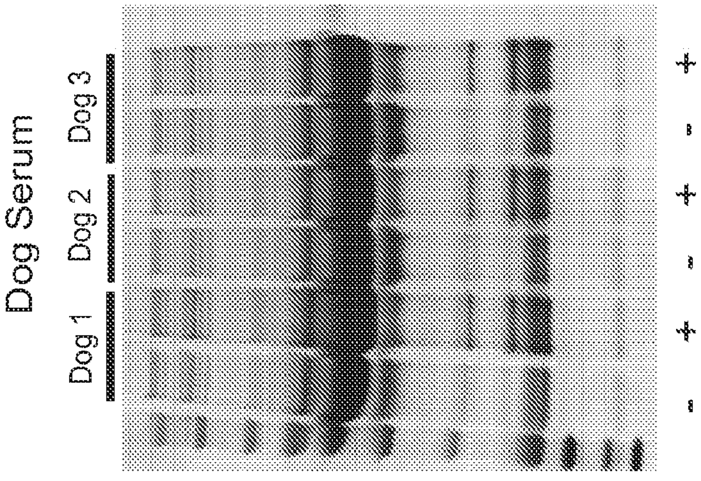
Figure 2D:
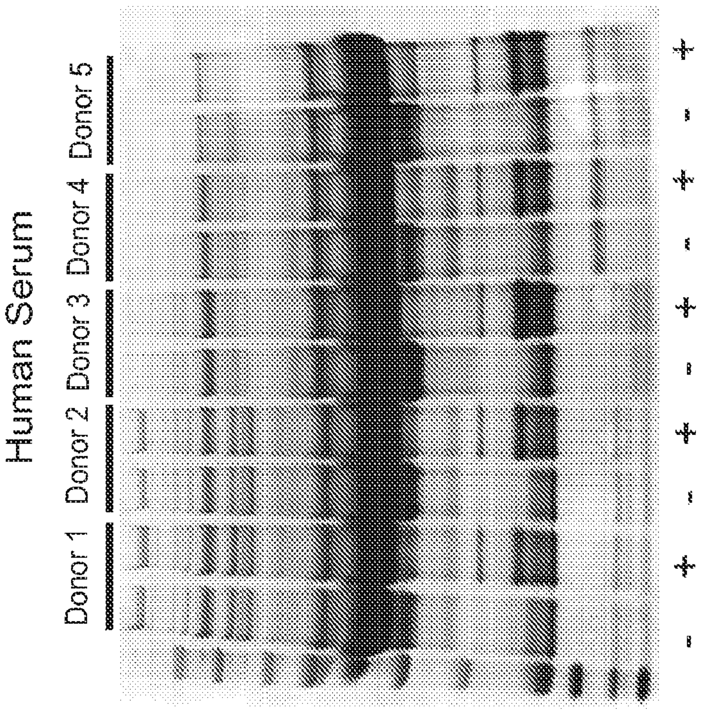

In an additional experiment, serum samples from mouse, primate and human were untreated (−) or treated (+) with recombinant IdeZ (NEB P0770S, 320 units) for 3 hours at 37° C. Reactions were diluted 1:10 and analyzed by SDS-PAGE under reducing conditions. Gels were then stained with Coomassie blue. As shown in FIG. 2B, IgG present within serum was cleaved by IdeZ. In FIG. 2B, the lower gel represents an overexposure of the portion of the gel containing the IgG heavy chain cleavage product (~31 kDa). IdeZ also cleaved IgG in serum samples from additional human patients (Donors 1-5) (FIG. 2D). In a similar experiment, it was also observed that IdeZ can cleave IgG from dog serum (FIG. 2C). Taken together, these data demonstrate that IdeZ can cleave IgG in serum from multiple species.

Example 3: IdeZ Cleaves Human IVIG In Vitro and In Vivo

Figure 3A:
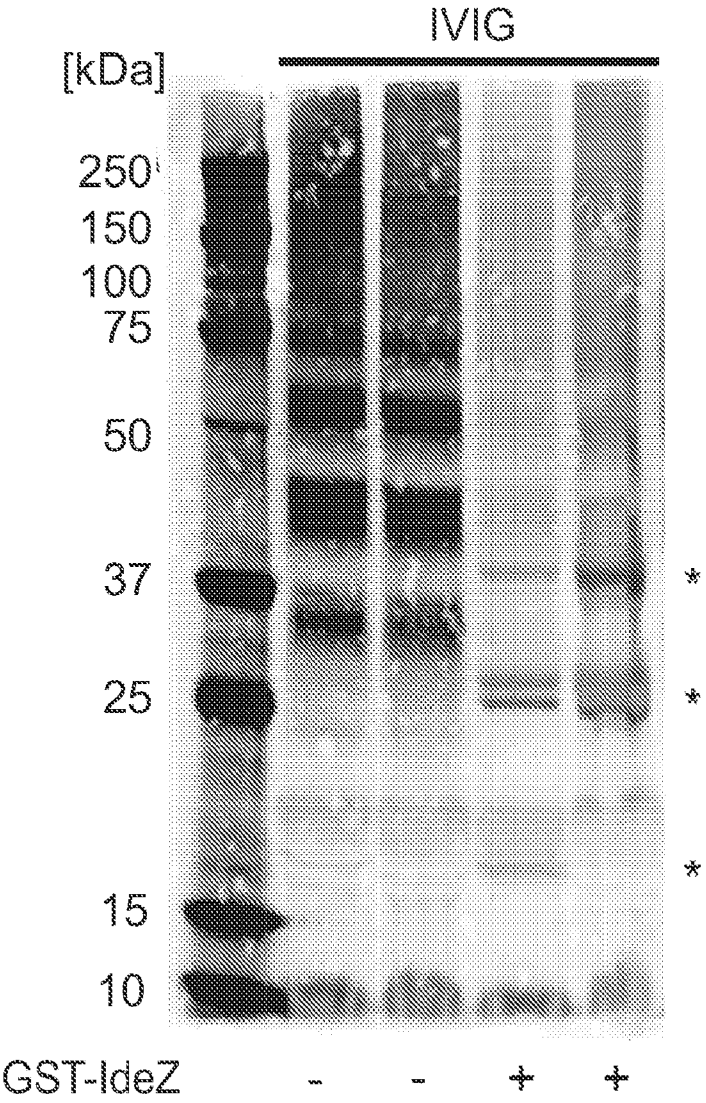
FIG. 3A-3B.
Figure 3B:
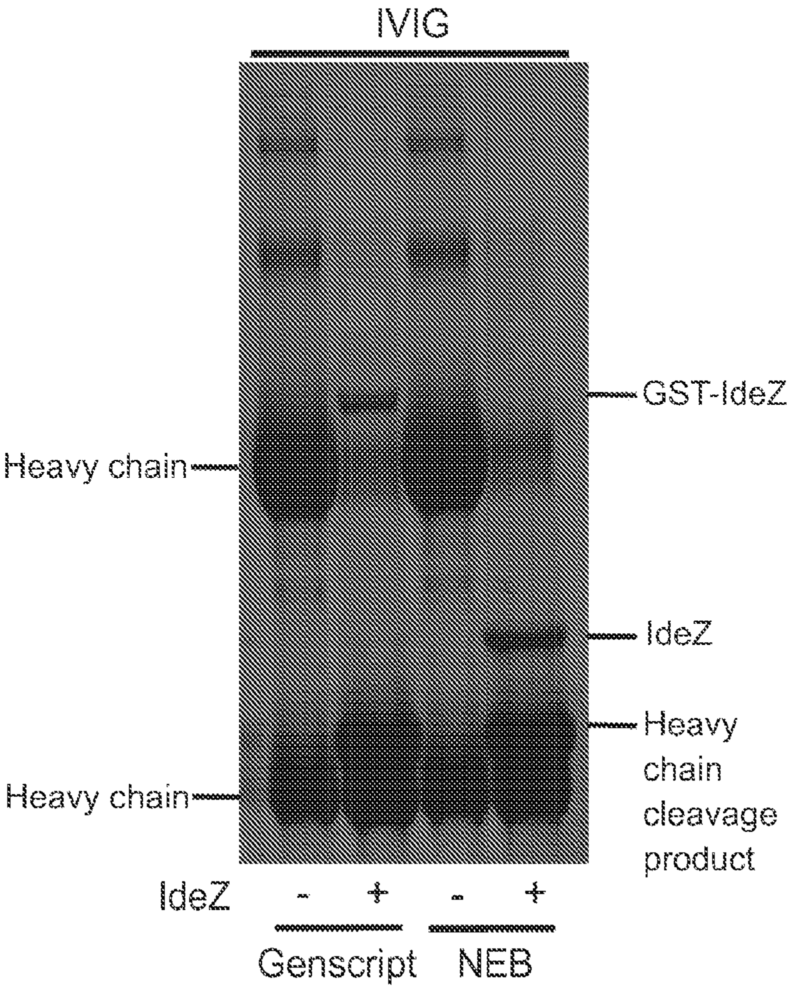

Human intravenous immunoglobulin (IVIG) was incubated with GST-IdeZ (1 μg) or IdeZ (NEB P0770S or Genscript) for 2 hours at 37° C. Reactions were analyzed by SDS-PAGE under reducing conditions and stained with Coomassie blue. As shown in FIG. 3B, IdeZ cleaved human IVIG in vitro.

Mice were injected intraperitoneally with 8 mg of human IVIG. The same mice were injected intravenously 24 hours later with PBS (−) or recombinant IdeZ (2.5 mg/kg) (+). Blood samples were taken 72 hours post IVIG injection and analyzed by SDS-PAGE under reducing conditions with immunoblotting. IVIG was probed with goat anti-human IgG Alexa Fluor 647 (1:10,000). In the presence of IdeZ, human IVIG was digested into multiple smaller cleavage products as indicated with asterisks (FIG. 3A). These data indicate that IdeZ cleaves human IVIG in vivo.

Figure 7:
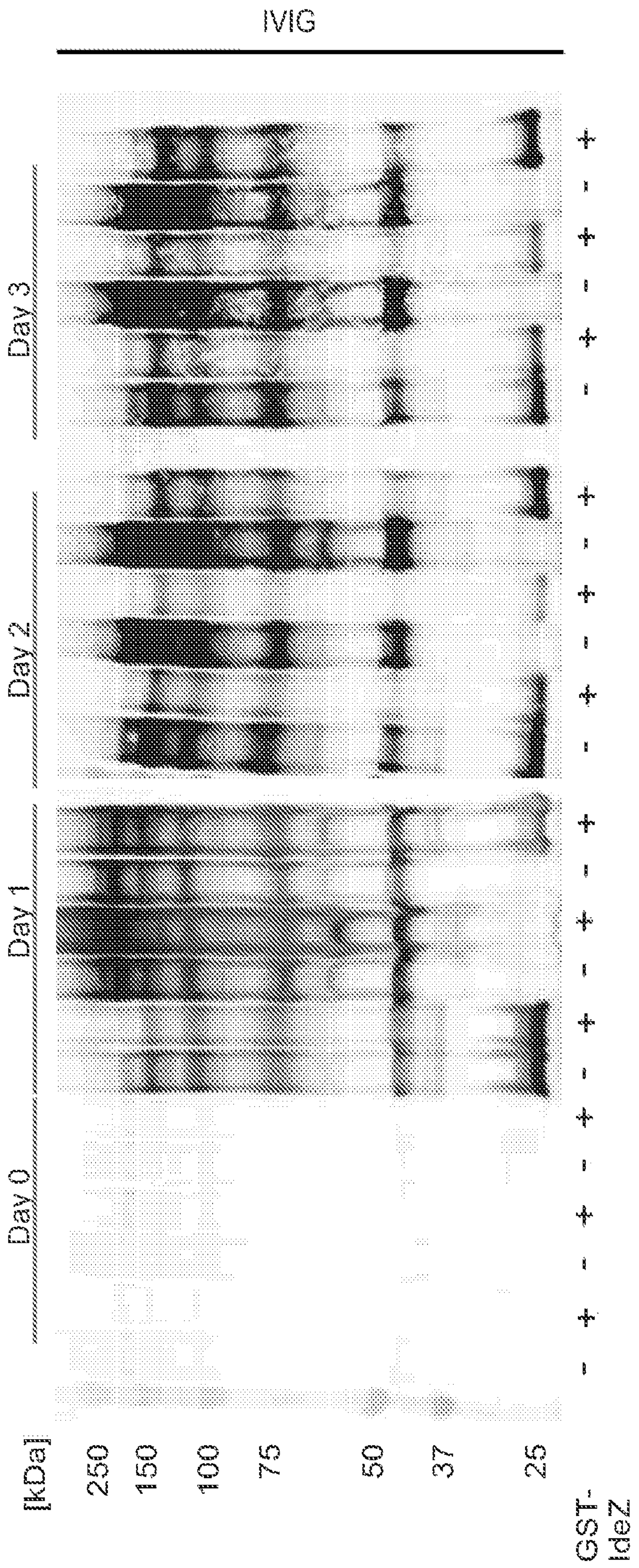
FIG. 7.

In a similar experiment, mice were injected intraperitoneally with 8 mg of human IVIG. The same mice were injected intravenously 24 hours later with PBS (−) or recombinant GST-IdeZ (2.5 mg/kg) (+). Blood samples were taken prior to injection, and 24 hours, 48 hours, and 72 hours post IVIG injection. As shown in FIG. 7, IdeZ cleaved human IVIG within 24 hours, and the level of cleavage continued to increase up to the 72 hour (Day 3) time point.

Example 4: Dose Analysis of GST-IdeZ Mediated IVIG Cleavage

Figure 8A:
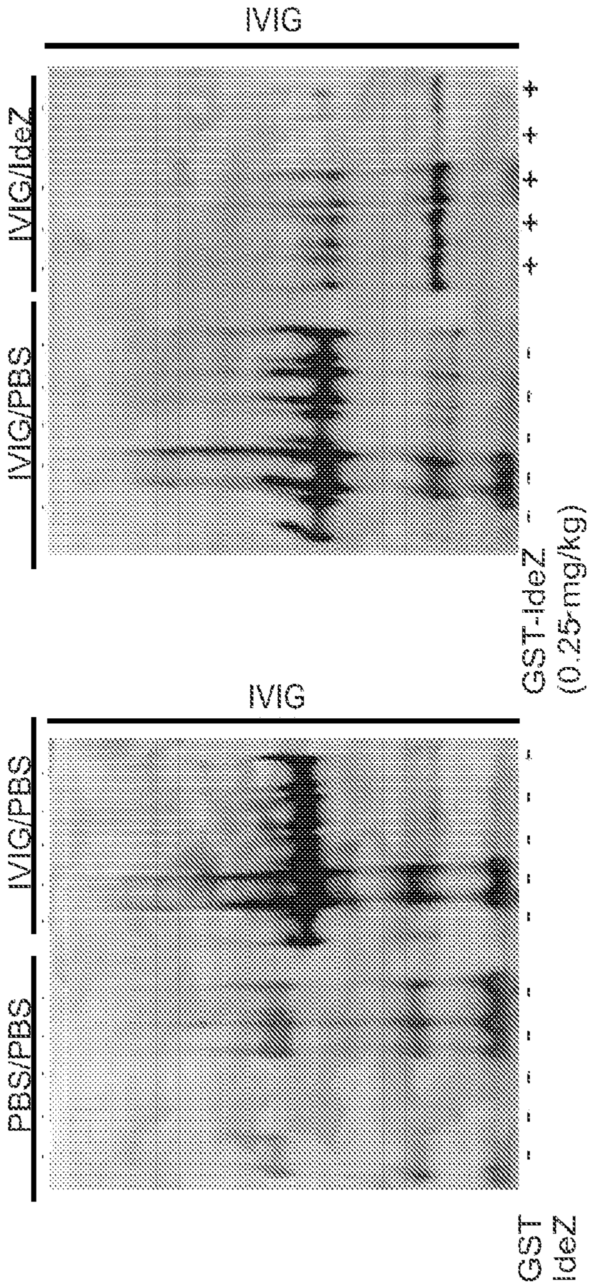
FIG. 8A-8B.
Figure 8B:
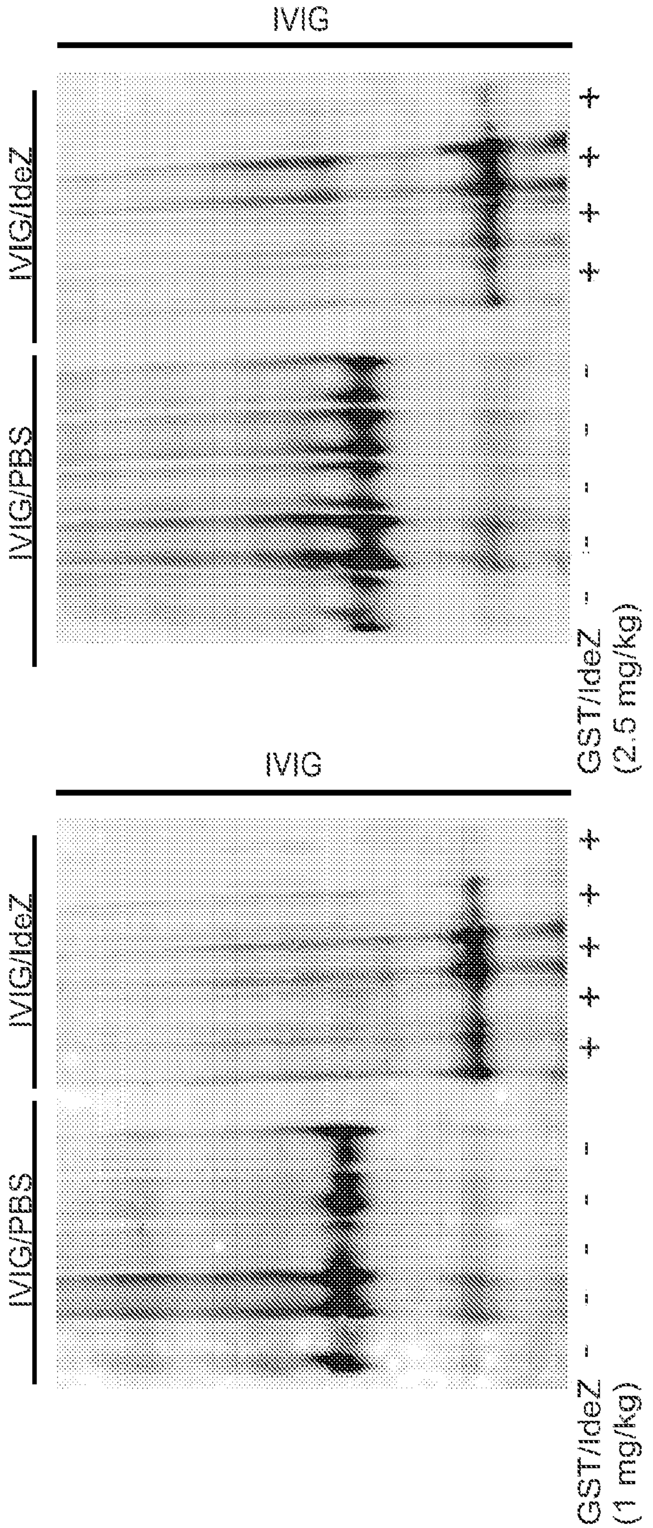

A dose analysis of GST-IdeZ mediated IVIG cleavage was also performed. In this experiment, mice were injected intraperitoneally with 8 mg of human IVIG. The same mice were injected intravenously 24 hours later with PBS (−) or recombinant GST-IdeZ (0.25 mg/kg) (+). As shown in FIG. 8A-8B, cleavage was dose dependent. At the highest dose (2.5 mg/kg), nearly all of the IVIG in each sample was cleaved, as evidenced by the shift in the size of the band.

Figure 9:
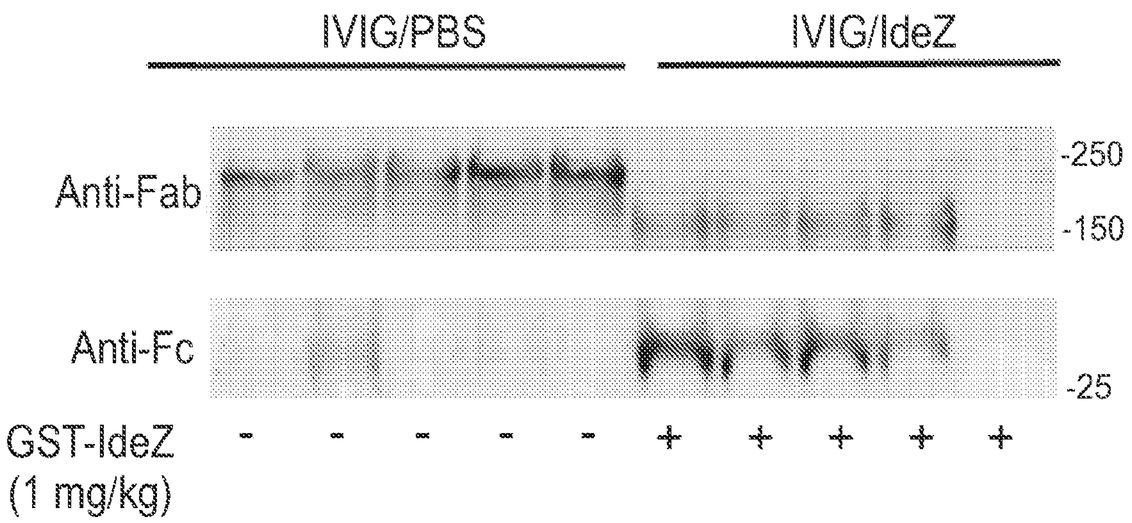
FIG. 9.

The cleavage site of IdeZ lies within the hinge region of human immunoglobulins. To confirm whether IdeZ was cleaving IVIG, serum samples from the mice PBS (−) or with 1 mg/kG IdeZ (+) were run on an SDS-PAGE gel and probed using either anti-Fab or anti-Fc antibodies. As shown in FIG. 9, the Fab band shifted in size (from about 250 to about 150 kDa) as a result of IdeZ treatment, indicating that a cleavage had occurred. A Fc band appeared around 50 kDa in IdeZ treated samples, indicating that this domain had been separated from the Fab.

Figure 10:
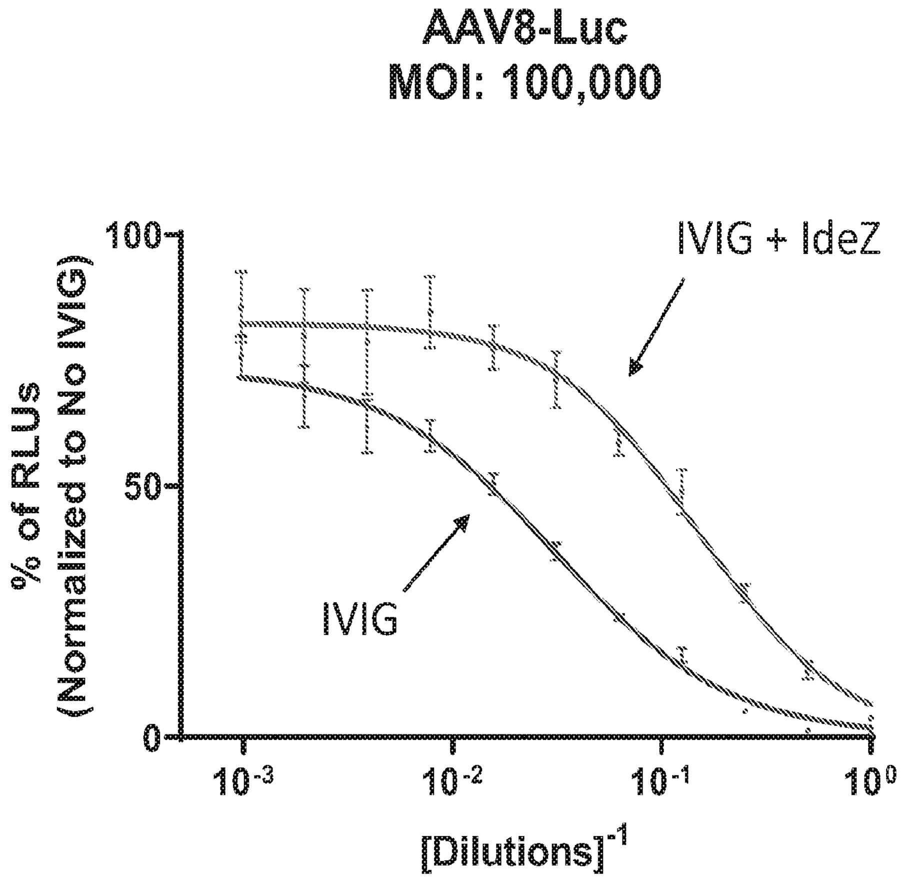
FIG. 10.

A neutralization profile of AAV8-Luc with human IVIG was also prepared. Human IVIG treated with and without GST-IdeZ (1 μg) were serially diluted in two-fold increments from 1:1000 to 1:102,400 and then co-incubated with AAV8-Luc and administered to cells in culture (100,000 vg/cell). As evidenced by the curves in in FIG. 10, neutralization of AAV8-Luc was reduced in the presence of GST-IdeZ.

Example 5: IdeZ Rescues AAV8-Luc Liver Transduction in IVIG Treated Mice

Mice were injected intraperitoneally with 8 mg of human IVIG. The same mice were injected intravenously 24 hours later with PBS or recombinant IdeZ (2.5 mg/kg) and AAV8-Luc ($5\times10^{12}$ vg/kg). Luciferase transgene expression levels were analyzed 4 weeks post injection in the liver. Luciferase expression levels were normalized for total tissue protein concentration and represented as relative light units (RLU) per gram of liver tissue. All experiments were carried out in triplicate. * $p<0.05$; L.O.D=limit of detection.

Figure 4:
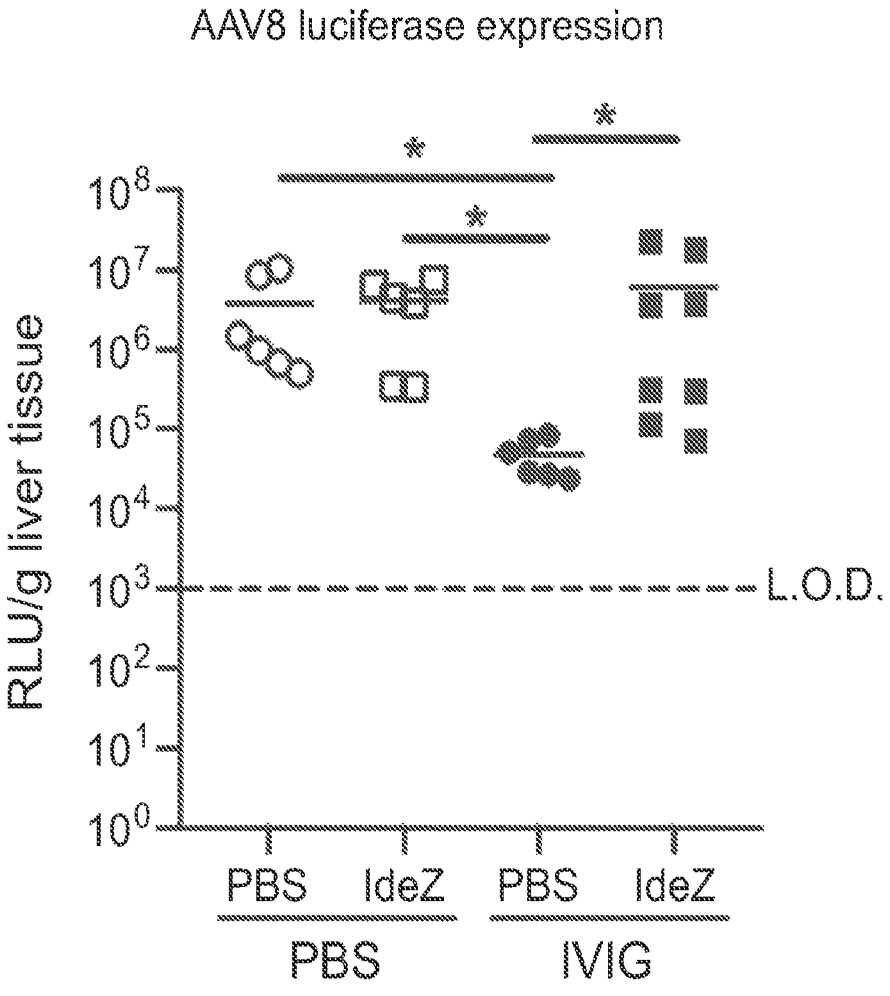
FIG. 4. Provided in FIG. 4 is a graph showing the results of an experiment wherein mice were injected intraperitoneally with human intravenous immunoglobulin (IVIG) and were subsequently injected 24 hours later with PBS or recombinant IdeZ (2.5 mg/kg) and AAV8-Luc ($5\times10^{12}$ vg/kg). Luciferase (Luc) transgene expression levels in the liver were analyzed 4 weeks post-injection in the liver. Luciferase expression levels were normalized for total tissue protein concentration and represented as relative light units (RLU) per gram of liver tissue. All experiments were carried out in triplicate. L.O.D=limit of detection. * $p<0.05$.

As shown in FIG. 4, Mice treated with IVIG showed decreased levels of AAV8-Luc transduction in the liver. However, IVIG treated mice co-injected with IdeZ showed AAV8-Luc liver transduction at levels similar to PBS treated mice.

Figure 11:
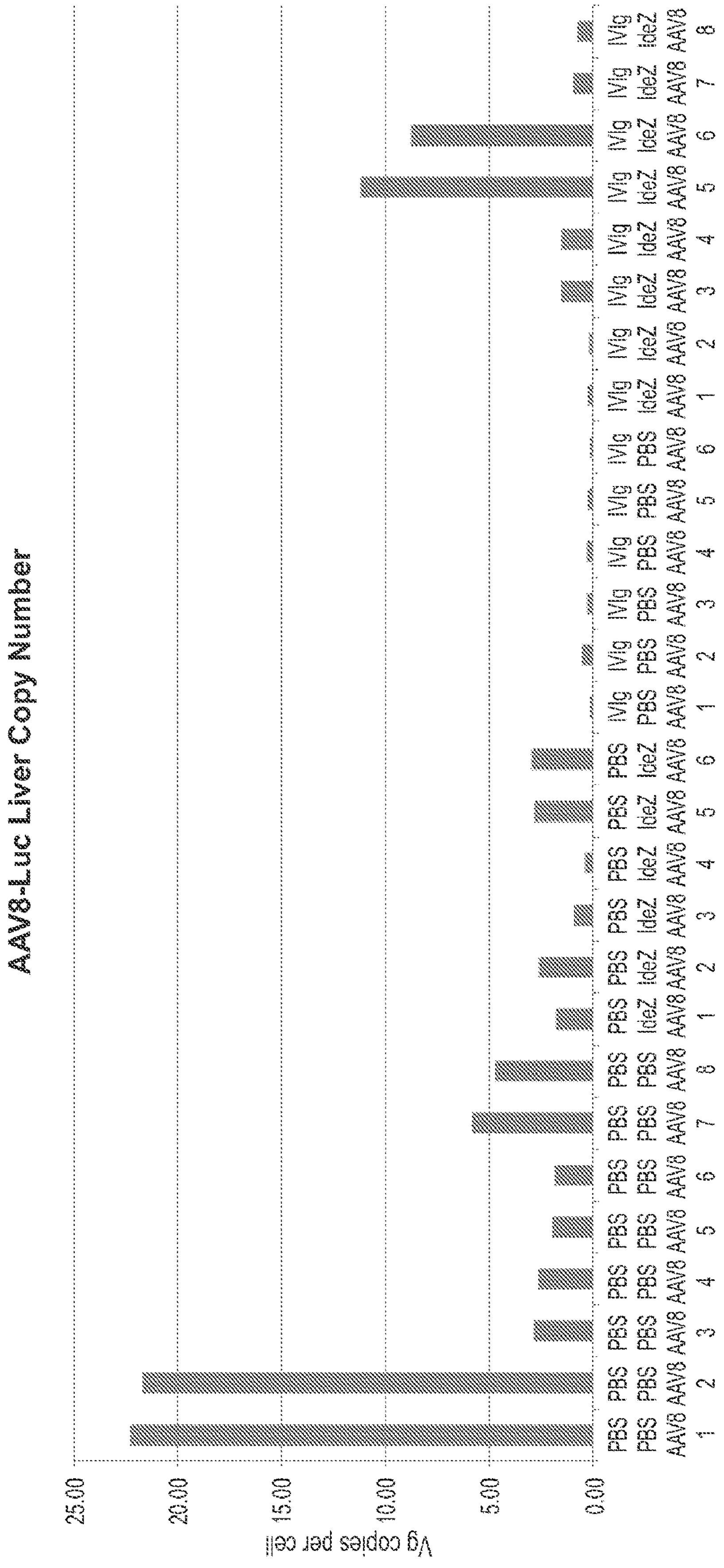
FIG. 11.

AAV8-Luc copy number was calculated in liver samples from the mice. As shown in FIG. 11, AAV-Luc copy number per cell was higher in samples from IVIG treated mice co-injected AAV8-Luc and IdeZ. Liver transduction was very low in mice not treated with IdeZ.

Taken together, these data indicate that IdeZ reduces neutralization of AAV by IVIG and promotes AAV8-Luc liver transduction.

Example 6: IdeZ Rescues AAV9-Luc Liver and Heart Transduction in IVIG Treated Mice Mice were injected intraperitoneally with 8 mg of human IVIG. The same mice were injected intravenously 72 hours later with PBS or recombinant GST-IdeZ (2.5 mg/kg). Mice were subsequently injected intravenously 72 hrs post-IdeZ treatment with AAV9-Luc ($2\times10^{11}$ vg/mouse). Luciferase transgene expression levels were analyzed 4 weeks post-injection in the liver and heart. Luciferase expression levels were normalized for total tissue protein concentration and represented as relative light units (RLU) per gram of liver tissue.

Figure 12A:
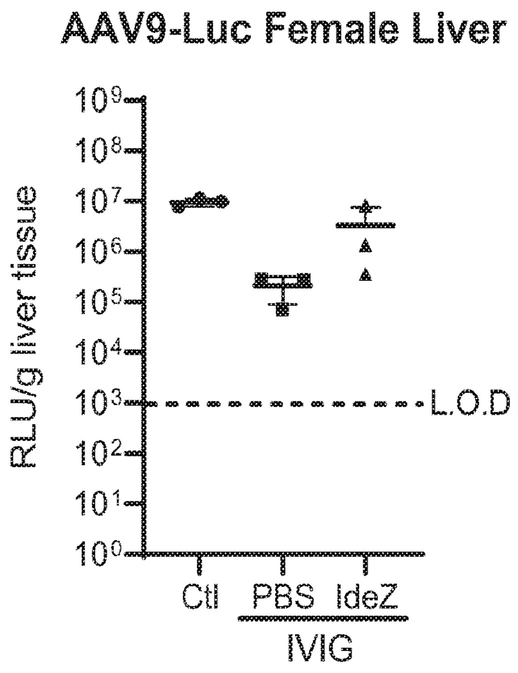
FIG. 12A-12D. Provided in FIG. 12A-12D are graphs showing the results of an experiment wherein mice were injected intraperitoneally with 8 mg human IVIG and were subsequently injected 72 hours later with PBS or recombinant GST-IdeZ (2.5 mg/kg). Mice were then injected intravenously 72 hours post-IdeZ treatment with AAV9-Luc ($2\times10^{11}$ vg/kg). Luciferase (Luc) transgene expression levels in the liver were analyzed 4 weeks post-injection in the liver and heart. Luciferase expression levels were normalized for total tissue protein concentration and represented as relative light units (RLU) per gram of liver tissue. All experiments were carried out in triplicate. L.O.D=limit of detection.
Figure 12B:
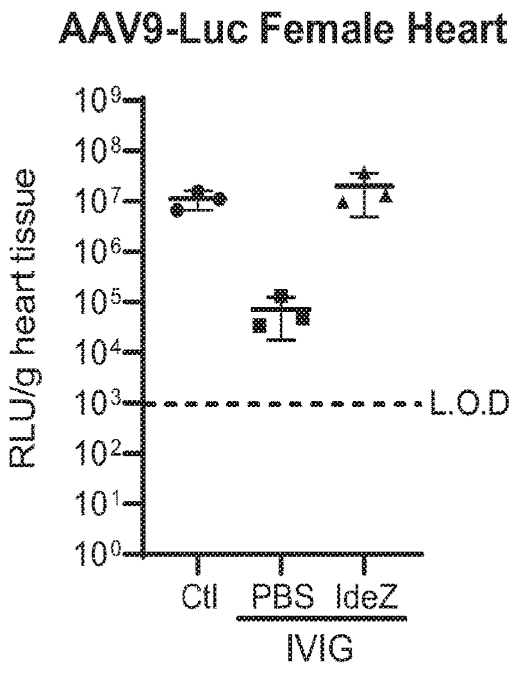
Figure 12C:
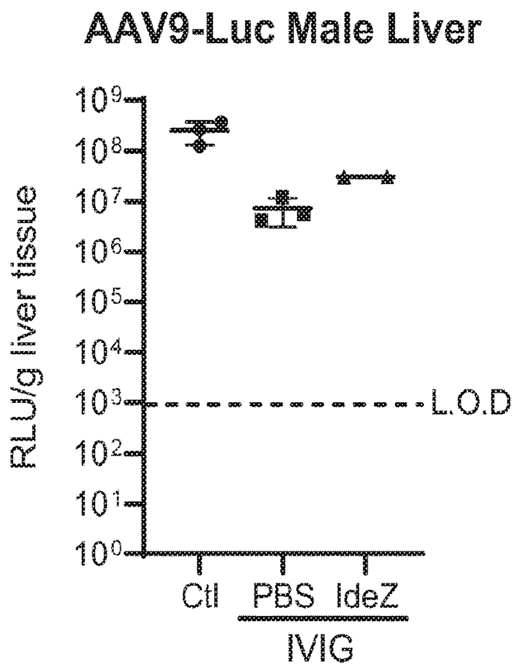
Figure 12D:
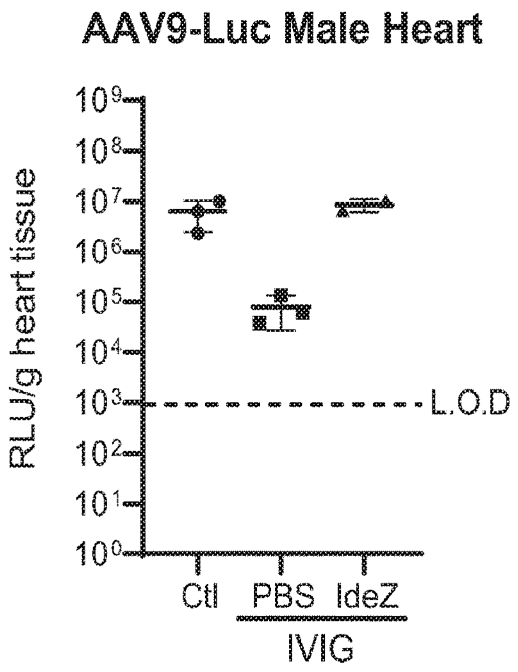

Male and female mice treated with IVIG showed decreased levels of AAV9-Luc transduction in the liver (FIG. 12A, FIG. 12C) and heart (FIG. 12B, FIG. 12D). However, IVIG treated mice co-injected with GST-IdeZ showed AAV9-Luc liver and heart transduction at levels similar to PBS treated mice.

Taken together, these data indicate that IdeZ negates IVIG mediated neutralization of AAV and promotes AAV9-Luc liver and heart transduction. (L.O.D=limit of detection)

Example 7: IdeZ Improves AAV9-Luc Liver and Heart Transduction in Patient Serum Treated Mice Serum samples from 18 human patients were tested for their ability to neutralize AAV9 transduction in the liver and heart.

Two mice per human serum sample were utilized for the study and both mice were injected intraperitoneally with 100 μl of human patient serum. Mice were then injected intravenously 72 hours later with PBS or recombinant GST-IdeZ (2.5 mg/kg). Mice were subsequently injected intravenously 72 hrs post-IdeZ treatment with AAV9-Luc ($2\times10^{11}$ vg/mouse).

Liver and heart transduction levels were analyzed 4 weeks post-injection. Transduction levels were normalized to control mice that were injected with AAV9-Luc ($2\times10^{11}$ vg/mouse) without serum treatment.

Figure 13A:
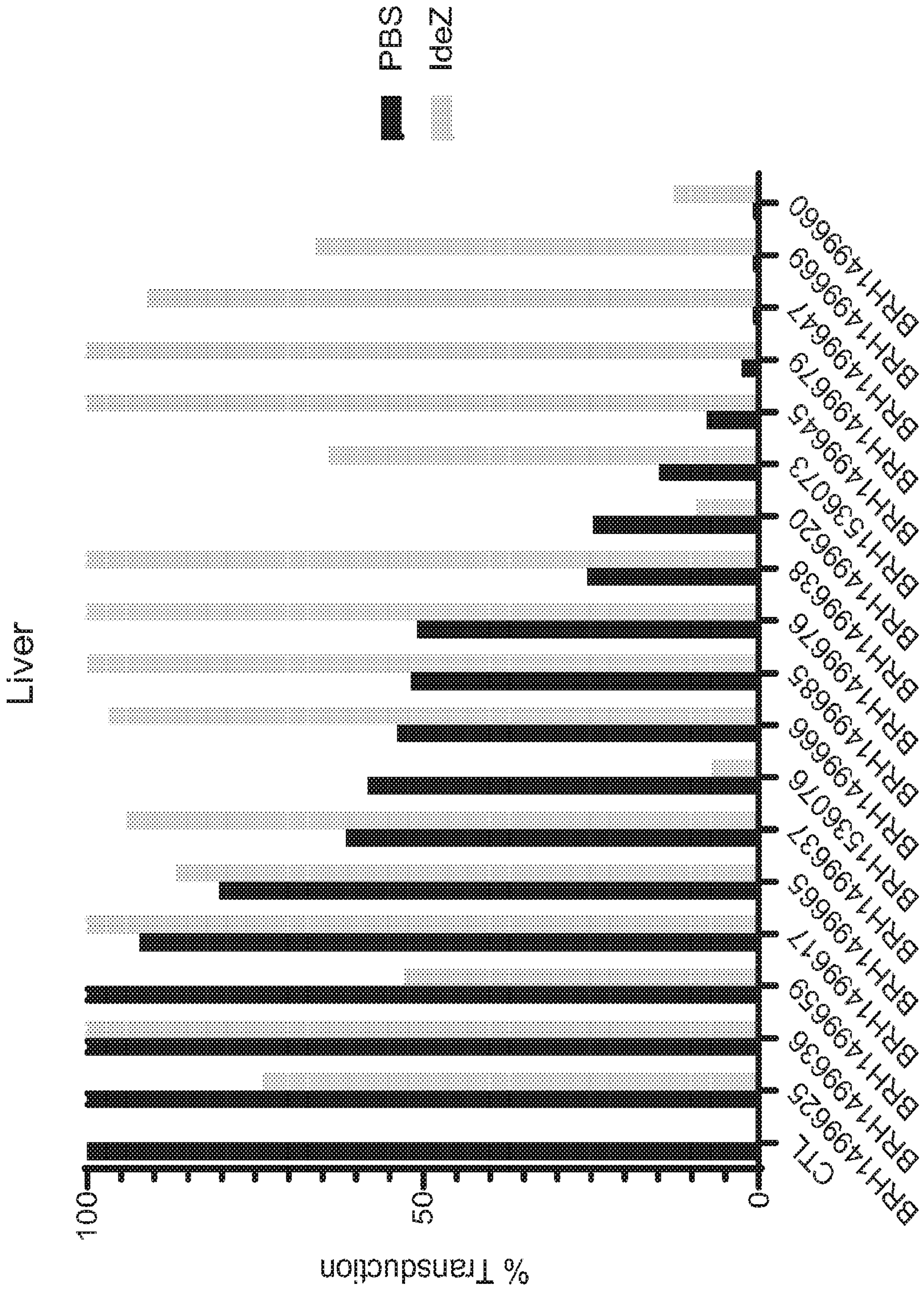
FIG. 13A-13B.
Figure 13B:
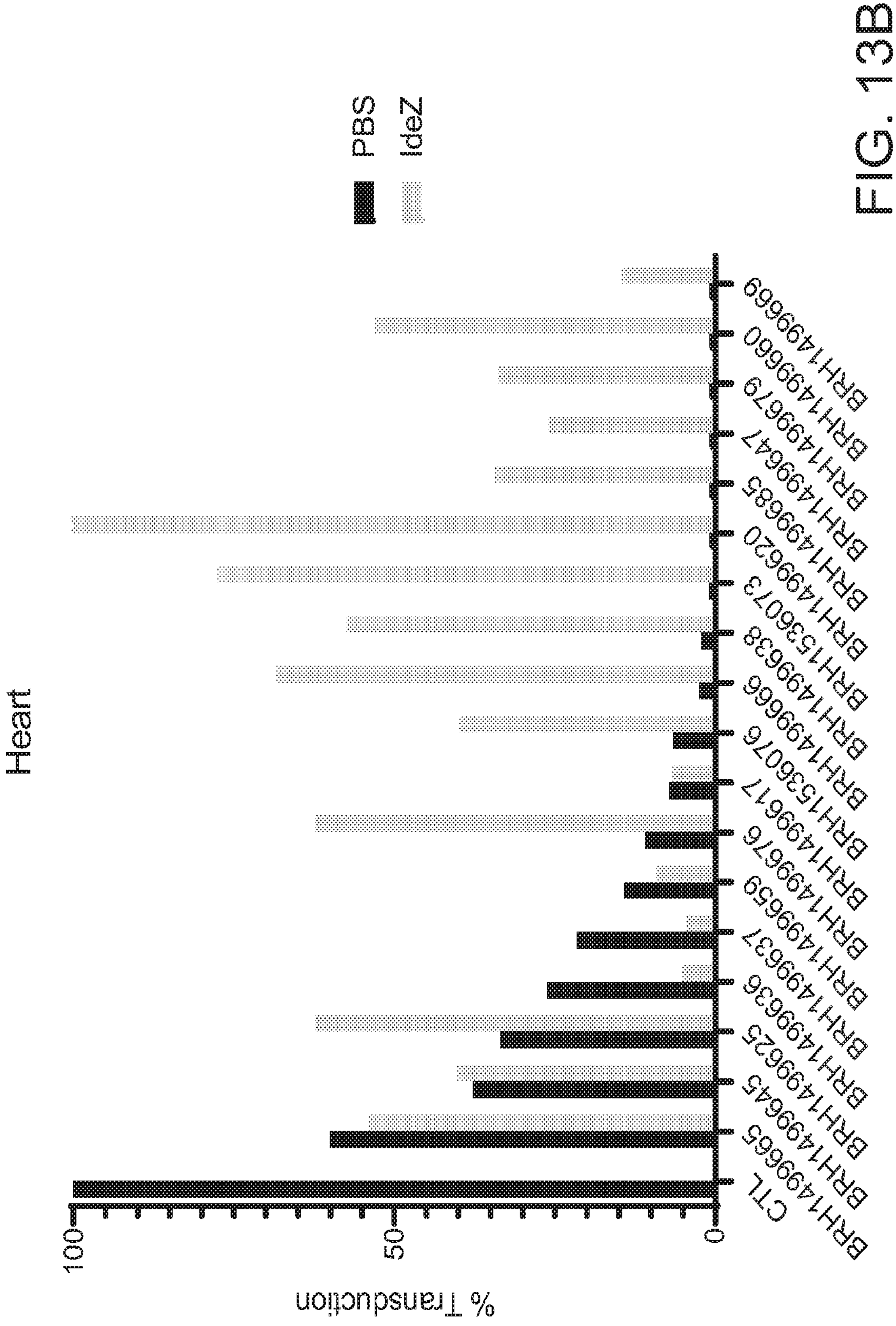

As shown in FIGS. 13A and 13B, mice treated with human patient serum showed differential levels of transduction. However, mice treated with strongly neutralizing patient serum showed increased liver (FIG. 13A) and heart (FIG. 13B) transduction when co-injected with GST-IdeZ.

Taken together, these data indicate that IdeZ antagonizes patient serum mediated neutralization of AAV and promotes AAV9-Luc liver and heart transduction.

One skilled in the art will readily appreciate that the present disclosure is well adapted to carry out the objects and obtain the ends and advantages mentioned, as well as those inherent therein. The present disclosure described herein are presently representative of preferred embodiments, are exemplary, and are not intended as limitations on the scope of the present disclosure. Changes therein and other uses will occur to those skilled in the art which are encompassed within the spirit of the present disclosure as defined by the scope of the claims.

What is claimed is:

1. A method for reducing, in a subject in need thereof, the amount of a neutralizing antibody against a recombinant adeno-associated virus (AAV) vector, the method comprising:

administering to the subject a therapeutically effective amount of a composition comprising a fusion protein comprising (i) an antibody-degrading enzyme having the sequence of SEQ ID NO:01, and (ii) an IgG protease, wherein the antibody-degrading enzyme (a) promotes the degradation of the neutralizing antibody against the recombinant AAV vector and/or against a therapeutic protein or a therapeutic RNA encoded therein, and/or (b) reduces the binding of the neutralizing antibody to an Fc receptor.

2. The method of claim 1, wherein the recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector.

3. The method of claim 1, wherein the antibody-degrading enzyme specifically cleaves IgG.

4. The method of claim 1, wherein the subject is treated with the recombinant AAV vector before administration of the composition.

5. The method of claim 1, wherein following the administering of the composition, complement activation is reduced and/or inhibited.

6. A method of treating a subject in need thereof with a recombinant adeno-associated virus (AAV) vector, the method comprising:

(i) administering to the subject an effective amount of a composition comprising a fusion protein comprising (1) an antibody-degrading enzyme having the sequence of SEQ ID NO:01 that (a) promotes the degradation of a neutralizing antibody against the recombinant AAV vector and/or a therapeutic protein or a therapeutic RNA encoded therein, and/or (b) reduces the binding of the neutralizing antibody to an Fc receptor, and (2) an IgG protease; and (ii) administering to the subject an effective amount of the recombinant AAV vector.

7. The method of claim 6, wherein the recombinant AAV vector is administered: (i) concurrently with the composition, (ii) after the administration of the composition; or (iii) prior to the administration of the composition.

8. The method of claim 6, wherein the method further comprises administering to the subject a second recombinant AAV vector.

9. The method of claim 6, wherein the recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector.

10. The method of claim 6, wherein the antibody-degrading enzyme specifically cleaves IgG.

11. The method of claim 6, wherein following the administering of the composition, complement activation is reduced and/or inhibited.

12. A method of treating a subject in need thereof with a second recombinant adeno-associated virus (AAV) vector, wherein the subject has previously been treated with a first recombinant AAV, the method comprising:

(i) administering to the subject an effective amount of a composition comprising a fusion protein comprising (1) an antibody-degrading enzyme having the sequence of SEQ ID NO:01 that (a) promotes the degradation of a neutralizing antibody against the first and/or the second recombinant AAV vector and/or a therapeutic protein or a therapeutic RNA encoded therein, and/or (b) reduces the binding of the neutralizing antibody to an Fc receptor, and (2) an IgG protease; and (ii) administering to the subject an effective amount of the second recombinant AAV vector.

13. The method of claim 12, wherein the first recombinant AAV vector and/or the second recombinant AAV vector is an AAV1, AAV2, AAV3, AAV4, AAV5, AAV6, AAV7, AAV8, AAV9, AAV10, AAV11, AAV12, AAVrh8, AAVrh10, AAVrh32.33, AAVrh74, Avian AAV or Bovine AAV vector.

14. The method of claim 12, wherein the antibody-degrading enzyme specifically cleaves IgG.

15. The method of claim 12, wherein following the administering of the composition, complement activation is reduced and/or inhibited.

16. A method of improving gene delivery, the method comprising:

increasing the circulation time and/or the infectivity of a recombinant adeno-associated virus (rAAV) vector in a subject by administering to the subject a therapeutically effective amount of a composition comprising a fusion protein comprising (i) an antibody-degrading enzyme having the sequence of SEQ ID NO:01 and (ii) an IgG protease, wherein the antibody-degrading enzyme (a) promotes the degradation of the neutralizing antibody against the rAAV vector and/or against a therapeutic protein or a therapeutic RNA encoded therein, and/or (b) reduces the binding of the neutralizing antibody to an Fc receptor, wherein the gene delivery is improved by the increased circulation time and/or the increased infectivity of the rAAV vector.

* * * * *

SEQUENCE LISTING

```
<160> NUMBER OF SEQ ID NOS: 52

<210> SEQ ID NO 1
<211> LENGTH: 349
<212> TYPE: PRT
<213> ORGANISM: Streptococcus equi

<400> SEQUENCE: 1

Met Lys Thr Ile Ala Tyr Pro Asn Lys Pro His Ser Leu Ser Ala Gly
1               5                   10                  15

Leu Leu Thr Ala Ile Ala Ile Phe Ser Leu Ala Ser Ser Asn Ile Thr
            20                  25                  30

Tyr Ala Asp Asp Tyr Gln Arg Asn Ala Thr Glu Ala Tyr Ala Lys Glu
        35                  40                  45
```

```
Val Pro His Gln Ile Thr Ser Val Trp Ser Lys Gly Val Thr Pro Leu
    50                  55                  60

Thr Pro Glu Gln Phe Arg Tyr Asn Asn Glu Asp Val Ile His Ala Pro
65                  70                  75                  80

Tyr Leu Ala His Gln Gly Trp Tyr Asp Ile Thr Lys Ala Phe Asp Gly
                85                  90                  95

Lys Asp Asn Leu Leu Cys Gly Ala Ala Thr Ala Gly Asn Met Leu His
            100                 105                 110

Trp Trp Phe Asp Gln Asn Lys Thr Glu Ile Glu Ala Tyr Leu Ser Lys
        115                 120                 125

His Pro Glu Lys Gln Lys Ile Ile Phe Asn Asn Gln Glu Leu Phe Asp
    130                 135                 140

Leu Lys Ala Ala Ile Asp Thr Lys Asp Ser Gln Thr Asn Ser Gln Leu
145                 150                 155                 160

Phe Asn Tyr Phe Arg Asp Lys Ala Phe Pro Asn Leu Ser Ala Arg Gln
                165                 170                 175

Leu Gly Val Met Pro Asp Leu Val Leu Asp Met Phe Ile Asn Gly Tyr
            180                 185                 190

Tyr Leu Asn Val Phe Lys Thr Gln Ser Thr Asp Val Asn Arg Pro Tyr
        195                 200                 205

Gln Asp Lys Asp Lys Arg Gly Gly Ile Phe Asp Ala Val Phe Thr Arg
    210                 215                 220

Gly Asp Gln Thr Thr Leu Leu Thr Ala Arg His Asp Leu Lys Asn Lys
225                 230                 235                 240

Gly Leu Asn Asp Ile Ser Thr Ile Ile Lys Gln Glu Leu Thr Glu Gly
                245                 250                 255

Arg Ala Leu Ala Leu Ser His Thr Tyr Ala Asn Val Ser Ile Ser His
            260                 265                 270

Val Ile Asn Leu Trp Gly Ala Asp Phe Asn Ala Glu Gly Asn Leu Glu
        275                 280                 285

Ala Ile Tyr Val Thr Asp Ser Asp Ala Asn Ala Ser Ile Gly Met Lys
    290                 295                 300

Lys Tyr Phe Val Gly Ile Asn Ala His Gly His Val Ala Ile Ser Ala
305                 310                 315                 320

Lys Lys Ile Glu Gly Glu Asn Ile Gly Ala Gln Val Leu Gly Leu Phe
                325                 330                 335

Thr Leu Ser Ser Gly Lys Asp Ile Trp Gln Lys Leu Ser
            340                 345


<210> SEQ ID NO 2
<211> LENGTH: 736
<212> TYPE: PRT
<213> ORGANISM: Parvovirus adeno-associated virus

<400> SEQUENCE: 2

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
```

```
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400

Ser Gln Met Leu Arg Thr Gly Asn Asn Phe Thr Phe Ser Tyr Thr Phe
                405                 410                 415

Glu Glu Val Pro Phe His Ser Ser Tyr Ala His Ser Gln Ser Leu Asp
            420                 425                 430

Arg Leu Met Asn Pro Leu Ile Asp Gln Tyr Leu Tyr Tyr Leu Asn Arg
        435                 440                 445

Thr Gln Asn Gln Ser Gly Ser Ala Gln Asn Lys Asp Leu Leu Phe Ser
    450                 455                 460

Arg Gly Ser Pro Ala Gly Met Ser Val Gln Pro Lys Asn Trp Leu Pro
465                 470                 475                 480

Gly Pro Cys Tyr Arg Gln Gln Arg Val Ser Lys Thr Lys Thr Asp Asn
                485                 490                 495
```

Asn Asn Ser Asn Phe Thr Trp Thr Gly Ala Ser Lys Tyr Asn Leu Asn
500 505 510

Gly Arg Glu Ser Ile Ile Asn Pro Gly Thr Ala Met Ala Ser His Lys
515 520 525

Asp Asp Glu Asp Lys Phe Phe Pro Met Ser Gly Val Met Ile Phe Gly
530 535 540

Lys Glu Ser Ala Gly Ala Ser Asn Thr Ala Leu Asp Asn Val Met Ile
545 550 555 560

Thr Asp Glu Glu Glu Ile Lys Ala Thr Asn Pro Val Ala Thr Glu Arg
565 570 575

Phe Gly Thr Val Ala Val Asn Phe Gln Ser Ser Ser Thr Asp Pro Ala
580 585 590

Thr Gly Asp Val His Ala Met Gly Ala Leu Pro Gly Met Val Trp Gln
595 600 605

Asp Arg Asp Val Tyr Leu Gln Gly Pro Ile Trp Ala Lys Ile Pro His
610 615 620

Thr Asp Gly His Phe His Pro Ser Pro Leu Met Gly Gly Phe Gly Leu
625 630 635 640

Lys Asn Pro Pro Pro Gln Ile Leu Ile Lys Asn Thr Pro Val Pro Ala
645 650 655

Asn Pro Pro Ala Glu Phe Ser Ala Thr Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Val Gln Tyr Thr Ser Asn
690 695 700

Tyr Ala Lys Ser Ala Asn Val Asp Phe Thr Val Asp Asn Asn Gly Leu
705 710 715 720

Tyr Thr Glu Pro Arg Pro Ile Gly Thr Arg Tyr Leu Thr Arg Pro Leu
725 730 735

<210> SEQ ID NO 3
<211> LENGTH: 735
<212> TYPE: PRT
<213> ORGANISM: Parvovirus adeno-associated virus

<400> SEQUENCE: 3

Met Ala Ala Asp Gly Tyr Leu Pro Asp Trp Leu Glu Asp Thr Leu Ser
1 5 10 15

Glu Gly Ile Arg Gln Trp Trp Lys Leu Lys Pro Gly Pro Pro Pro Pro
20 25 30

Lys Pro Ala Glu Arg His Lys Asp Asp Ser Arg Gly Leu Val Leu Pro
35 40 45

Gly Tyr Lys Tyr Leu Gly Pro Phe Asn Gly Leu Asp Lys Gly Glu Pro
50 55 60

Val Asn Glu Ala Asp Ala Ala Ala Leu Glu His Asp Lys Ala Tyr Asp
65 70 75 80

Arg Gln Leu Asp Ser Gly Asp Asn Pro Tyr Leu Lys Tyr Asn His Ala
85 90 95

Asp Ala Glu Phe Gln Glu Arg Leu Lys Glu Asp Thr Ser Phe Gly Gly
100 105 110

Asn Leu Gly Arg Ala Val Phe Gln Ala Lys Lys Arg Val Leu Glu Pro
115 120 125

Leu Gly Leu Val Glu Glu Pro Val Lys Thr Ala Pro Gly Lys Lys Arg

-continued

```
    130                 135                 140

Pro Val Glu His Ser Pro Val Glu Pro Asp Ser Ser Ser Gly Thr Gly
145                 150                 155                 160

Lys Ala Gly Gln Gln Pro Ala Arg Lys Arg Leu Asn Phe Gly Gln Thr
                165                 170                 175

Gly Asp Ala Asp Ser Val Pro Asp Pro Gln Pro Leu Gly Gln Pro Pro
            180                 185                 190

Ala Ala Pro Ser Gly Leu Gly Thr Asn Thr Met Ala Thr Gly Ser Gly
        195                 200                 205

Ala Pro Met Ala Asp Asn Asn Glu Gly Ala Asp Gly Val Gly Asn Ser
    210                 215                 220

Ser Gly Asn Trp His Cys Asp Ser Thr Trp Met Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Arg Leu Asn Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Thr Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Ser Arg Thr
        435                 440                 445

Asn Thr Pro Ser Gly Thr Thr Thr Gln Ser Arg Leu Gln Phe Ser Gln
    450                 455                 460

Ala Gly Ala Ser Asp Ile Arg Asp Gln Ser Arg Asn Trp Leu Pro Gly
465                 470                 475                 480

Pro Cys Tyr Arg Gln Gln Arg Val Ser Lys Thr Ser Ala Asp Asn Asn
                485                 490                 495

Asn Ser Glu Tyr Ser Trp Thr Gly Ala Thr Lys Tyr His Leu Asn Gly
            500                 505                 510

Arg Asp Ser Leu Val Asn Pro Gly Pro Ala Met Ala Ser His Lys Asp
        515                 520                 525

Asp Glu Glu Lys Phe Phe Pro Gln Ser Gly Val Leu Ile Phe Gly Lys
    530                 535                 540

Gln Gly Ser Glu Lys Thr Asn Val Asp Ile Glu Lys Val Met Ile Thr
545                 550                 555                 560
```

Asp Glu Glu Glu Ile Arg Thr Thr Asn Pro Val Ala Thr Glu Gln Tyr
565 570 575

Gly Ser Val Ser Thr Asn Leu Gln Arg Gly Asn Arg Gln Ala Ala Thr
580 585 590

Ala Asp Val Asn Thr Gln Gly Val Leu Pro Gly Met Val Trp Gln Asp
595 600 605

Arg Asp Val Tyr Leu Gln Gly Pro Ile Trp Ala Lys Ile Pro His Thr
610 615 620

Asp Gly His Phe His Pro Ser Pro Leu Met Gly Gly Phe Gly Leu Lys
625 630 635 640

His Pro Pro Pro Gln Ile Leu Ile Lys Asn Thr Pro Val Pro Ala Asn
645 650 655

Pro Ser Thr Thr Phe Ser Ala Ala Lys Phe Ala Ser Phe Ile Thr Gln
660 665 670

Tyr Ser Thr Gly Gln Val Ser Val Glu Ile Glu Trp Glu Leu Gln Lys
675 680 685

Glu Asn Ser Lys Arg Trp Asn Pro Glu Ile Gln Tyr Thr Ser Asn Tyr
690 695 700

Asn Lys Ser Val Asn Val Asp Phe Thr Val Asp Thr Asn Gly Val Tyr
705 710 715 720

Ser Glu Pro Arg Pro Ile Gly Thr Arg Tyr Leu Thr Arg Asn Leu
725 730 735

<210> SEQ ID NO 4
<211> LENGTH: 736
<212> TYPE: PRT
<213> ORGANISM: Parvovirus adeno-associated virus

<400> SEQUENCE: 4

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Val Pro Gln Pro
20 25 30

Lys Ala Asn Gln Gln His Gln Asp Asn Arg Arg Gly Leu Val Leu Pro
35 40 45

Gly Tyr Lys Tyr Leu Gly Pro Gly Asn Gly Leu Asp Lys Gly Glu Pro
50 55 60

Val Asn Glu Ala Asp Ala Ala Ala Leu Glu His Asp Lys Ala Tyr Asp
65 70 75 80

Gln Gln Leu Lys Ala Gly Asp Asn Pro Tyr Leu Lys Tyr Asn His Ala
85 90 95

Asp Ala Glu Phe Gln Glu Arg Leu Gln Glu Asp Thr Ser Phe Gly Gly
100 105 110

Asn Leu Gly Arg Ala Val Phe Gln Ala Lys Lys Arg Ile Leu Glu Pro
115 120 125

Leu Gly Leu Val Glu Glu Ala Ala Lys Thr Ala Pro Gly Lys Lys Arg
130 135 140

Pro Val Asp Gln Ser Pro Gln Glu Pro Asp Ser Ser Ser Gly Val Gly
145 150 155 160

Lys Ser Gly Lys Gln Pro Ala Arg Lys Arg Leu Asn Phe Gly Gln Thr
165 170 175

Gly Asp Ser Glu Ser Val Pro Asp Pro Gln Pro Leu Gly Glu Pro Pro
180 185 190

Ala Ala Pro Thr Ser Leu Gly Ser Asn Thr Met Ala Ser Gly Gly Gly

```
        195                 200                 205

Ala Pro Met Ala Asp Asn Asn Glu Gly Ala Asp Gly Val Gly Asn Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Gln Ser Gly Ala Ser Asn Asp Asn His Tyr
            260                 265                 270

Phe Gly Tyr Ser Thr Pro Trp Gly Tyr Phe Asp Phe Asn Arg Phe His
        275                 280                 285

Cys His Phe Ser Pro Arg Asp Trp Gln Arg Leu Ile Asn Asn Asn Trp
    290                 295                 300

Gly Phe Arg Pro Lys Lys Leu Ser Phe Lys Leu Phe Asn Ile Gln Val
305                 310                 315                 320

Lys Glu Val Thr Gln Asn Asp Gly Thr Thr Thr Ile Ala Asn Asn Leu
                325                 330                 335

Thr Ser Thr Val Gln Val Phe Thr Asp Ser Glu Tyr Gln Leu Pro Tyr
            340                 345                 350

Val Leu Gly Ser Ala His Gln Gly Cys Leu Pro Pro Phe Pro Ala Asp
        355                 360                 365

Val Phe Met Val Pro Gln Tyr Gly Tyr Leu Thr Leu Asn Asn Gly Ser
    370                 375                 380

Gln Ala Val Gly Arg Ser Ser Phe Tyr Cys Leu Glu Tyr Phe Pro Ser
385                 390                 395                 400

Gln Met Leu Arg Thr Gly Asn Asn Phe Gln Phe Ser Tyr Thr Phe Glu
                405                 410                 415

Asp Val Pro Phe His Ser Ser Tyr Ala His Ser Gln Ser Leu Asp Arg
            420                 425                 430

Leu Met Asn Pro Leu Ile Asp Gln Tyr Leu Tyr Tyr Leu Asn Arg Thr
        435                 440                 445

Gln Gly Thr Thr Ser Gly Thr Thr Asn Gln Ser Arg Leu Leu Phe Ser
    450                 455                 460

Gln Ala Gly Pro Gln Ser Met Ser Leu Gln Ala Arg Asn Trp Leu Pro
465                 470                 475                 480

Gly Pro Cys Tyr Arg Gln Gln Arg Leu Ser Lys Thr Ala Asn Asp Asn
                485                 490                 495

Asn Asn Ser Asn Phe Pro Trp Thr Ala Ala Ser Lys Tyr His Leu Asn
            500                 505                 510

Gly Arg Asp Ser Leu Val Asn Pro Gly Pro Ala Met Ala Ser His Lys
        515                 520                 525

Asp Asp Glu Glu Lys Phe Phe Pro Met His Gly Asn Leu Ile Phe Gly
    530                 535                 540

Lys Glu Gly Thr Thr Ala Ser Asn Ala Glu Leu Asp Asn Val Met Ile
545                 550                 555                 560

Thr Asp Glu Glu Glu Ile Arg Thr Thr Asn Pro Val Ala Thr Glu Gln
                565                 570                 575

Tyr Gly Thr Val Ala Asn Asn Leu Gln Ser Ser Asn Thr Ala Pro Thr
            580                 585                 590

Thr Arg Thr Val Asn Asp Gln Gly Ala Leu Pro Gly Met Val Trp Gln
        595                 600                 605

Asp Arg Asp Val Tyr Leu Gln Gly Pro Ile Trp Ala Lys Ile Pro His
    610                 615                 620
```

Thr Asp Gly His Phe His Pro Ser Pro Leu Met Gly Gly Phe Gly Leu
625 630 635 640

Lys His Pro Pro Pro Gln Ile Met Ile Lys Asn Thr Pro Val Pro Ala
645 650 655

Asn Pro Pro Thr Thr Phe Ser Pro Ala Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Ile Gln Tyr Thr Ser Asn
690 695 700

Tyr Asn Lys Ser Val Asn Val Asp Phe Thr Val Asp Thr Asn Gly Val
705 710 715 720

Tyr Ser Glu Pro Arg Pro Ile Gly Thr Arg Tyr Leu Thr Arg Asn Leu
725 730 735

<210> SEQ ID NO 5
<211> LENGTH: 734
<212> TYPE: PRT
<213> ORGANISM: Parvovirus adeno-associated virus

<400> SEQUENCE: 5

Met Thr Asp Gly Tyr Leu Pro Asp Trp Leu Glu Asp Asn Leu Ser Glu
1 5 10 15

Gly Val Arg Glu Trp Trp Ala Leu Gln Pro Gly Ala Pro Lys Pro Lys
20 25 30

Ala Asn Gln Gln His Gln Asp Asn Ala Arg Gly Leu Val Leu Pro Gly
35 40 45

Tyr Lys Tyr Leu Gly Pro Gly Asn Gly Leu Asp Lys Gly Glu Pro Val
50 55 60

Asn Ala Ala Asp Ala Ala Ala Leu Glu His Asp Lys Ala Tyr Asp Gln
65 70 75 80

Gln Leu Lys Ala Gly Asp Asn Pro Tyr Leu Lys Tyr Asn His Ala Asp
85 90 95

Ala Glu Phe Gln Gln Arg Leu Gln Gly Asp Thr Ser Phe Gly Gly Asn
100 105 110

Leu Gly Arg Ala Val Phe Gln Ala Lys Lys Arg Val Leu Glu Pro Leu
115 120 125

Gly Leu Val Glu Gln Ala Gly Glu Thr Ala Pro Gly Lys Lys Arg Pro
130 135 140

Leu Ile Glu Ser Pro Gln Gln Pro Asp Ser Ser Thr Gly Ile Gly Lys
145 150 155 160

Lys Gly Lys Gln Pro Ala Lys Lys Lys Leu Val Phe Glu Asp Glu Thr
165 170 175

Gly Ala Gly Asp Gly Pro Pro Glu Gly Ser Thr Ser Gly Ala Met Ser
180 185 190

Asp Asp Ser Glu Met Arg Ala Ala Ala Gly Gly Ala Ala Val Glu Gly
195 200 205

Gly Gln Gly Ala Asp Gly Val Gly Asn Ala Ser Gly Asp Trp His Cys
210 215 220

Asp Ser Thr Trp Ser Glu Gly His Val Thr Thr Thr Ser Thr Arg Thr
225 230 235 240

Trp Val Leu Pro Thr Tyr Asn Asn His Leu Tyr Lys Arg Leu Gly Glu
245 250 255

Ser Leu Gln Ser Asn Thr Tyr Asn Gly Phe Ser Thr Pro Trp Gly Tyr

```
            260                 265                 270

Phe Asp Phe Asn Arg Phe His Cys His Phe Ser Pro Arg Asp Trp Gln
        275                 280                 285

Arg Leu Ile Asn Asn Asn Trp Gly Met Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Leu Val Thr Gly Asn Thr Ser Gln Gln Gln Thr Asp Arg Asn
    370                 375                 380

Ala Phe Tyr Cys Leu Glu Tyr Phe Pro Ser Gln Met Leu Arg Thr Gly
385                 390                 395                 400

Asn Asn Phe Glu Ile Thr Tyr Ser Phe Glu Lys Val Pro Phe His Ser
                405                 410                 415

Met Tyr Ala His Ser Gln Ser Leu Asp Arg Leu Met Asn Pro Leu Ile
            420                 425                 430

Asp Gln Tyr Leu Trp Gly Leu Gln Ser Thr Thr Thr Gly Thr Thr Leu
        435                 440                 445

Asn Ala Gly Thr Ala Thr Thr Asn Phe Thr Lys Leu Arg Pro Thr Asn
    450                 455                 460

Phe Ser Asn Phe Lys Lys Asn Trp Leu Pro Gly Pro Ser Ile Lys Gln
465                 470                 475                 480

Gln Gly Phe Ser Lys Thr Ala Asn Gln Asn Tyr Lys Ile Pro Ala Thr
                485                 490                 495

Gly Ser Asp Ser Leu Ile Lys Tyr Glu Thr His Ser Thr Leu Asp Gly
            500                 505                 510

Arg Trp Ser Ala Leu Thr Pro Gly Pro Pro Met Ala Thr Ala Gly Pro
        515                 520                 525

Ala Asp Ser Lys Phe Ser Asn Ser Gln Leu Ile Phe Ala Gly Pro Lys
    530                 535                 540

Gln Asn Gly Asn Thr Ala Thr Val Pro Gly Thr Leu Ile Phe Thr Ser
545                 550                 555                 560

Glu Glu Glu Leu Ala Ala Thr Asn Ala Thr Asp Thr Asp Met Trp Gly
                565                 570                 575

Asn Leu Pro Gly Gly Asp Gln Ser Asn Ser Asn Leu Pro Thr Val Asp
            580                 585                 590

Arg Leu Thr Ala Leu Gly Ala Val Pro Gly Met Val Trp Gln Asn Arg
        595                 600                 605

Asp Ile Tyr Tyr Gln Gly Pro Ile Trp Ala Lys Ile Pro His Thr Asp
    610                 615                 620

Gly His Phe His Pro Ser Pro Leu Ile Gly Gly Phe Gly Leu Lys His
625                 630                 635                 640

Pro Pro Pro Gln Ile Phe Ile Lys Asn Thr Pro Val Pro Ala Asn Pro
                645                 650                 655

Ala Thr Thr Phe Ser Ser Thr Pro Val Asn Ser Phe Ile Thr Gln Tyr
            660                 665                 670

Ser Thr Gly Gln Val Ser Val Gln Ile Asp Trp Glu Ile Gln Lys Glu
        675                 680                 685
```

```
Arg Ser Lys Arg Trp Asn Pro Glu Val Gln Phe Thr Ser Asn Tyr Gly
    690                 695                 700

Gln Gln Asn Ser Leu Leu Trp Ala Pro Asp Ala Ala Gly Lys Tyr Thr
705                 710                 715                 720

Glu Pro Arg Ala Ile Gly Thr Arg Tyr Leu Thr His His Leu
                725                 730


<210> SEQ ID NO 6
<211> LENGTH: 724
<212> TYPE: PRT
<213> ORGANISM: Parvovirus adeno-associated virus

<400> SEQUENCE: 6

Met Ser Phe Val Asp His Pro Pro Asp Trp Leu Glu Glu Val Gly Glu
1               5                   10                  15

Gly Leu Arg Glu Phe Leu Gly Leu Glu Ala Gly Pro Pro Lys Pro Lys
            20                  25                  30

Pro Asn Gln Gln His Gln Asp Gln Ala Arg Gly Leu Val Leu Pro Gly
        35                  40                  45

Tyr Asn Tyr Leu Gly Pro Gly Asn Gly Leu Asp Arg Gly Glu Pro Val
    50                  55                  60

Asn Arg Ala Asp Glu Val Ala Arg Glu His Asp Ile Ser Tyr Asn Glu
65                  70                  75                  80

Gln Leu Glu Ala Gly Asp Asn Pro Tyr Leu Lys Tyr Asn His Ala Asp
                85                  90                  95

Ala Glu Phe Gln Glu Lys Leu Ala Asp Asp Thr Ser Phe Gly Gly Asn
            100                 105                 110

Leu Gly Lys Ala Val Phe Gln Ala Lys Lys Arg Val Leu Glu Pro Phe
        115                 120                 125

Gly Leu Val Glu Glu Gly Ala Lys Thr Ala Pro Thr Gly Lys Arg Ile
    130                 135                 140

Asp Asp His Phe Pro Lys Arg Lys Lys Ala Arg Thr Glu Glu Asp Ser
145                 150                 155                 160

Lys Pro Ser Thr Ser Ser Asp Ala Glu Ala Gly Pro Ser Gly Ser Gln
                165                 170                 175

Gln Leu Gln Ile Pro Ala Gln Pro Ala Ser Ser Leu Gly Ala Asp Thr
            180                 185                 190

Met Ser Ala Gly Gly Gly Gly Pro Leu Gly Asp Asn Asn Gln Gly Ala
        195                 200                 205

Asp Gly Val Gly Asn Ala Ser Gly Asp Trp His Cys Asp Ser Thr Trp
    210                 215                 220

Met Gly Asp Arg Val Val Thr Lys Ser Thr Arg Thr Trp Val Leu Pro
225                 230                 235                 240

Ser Tyr Asn Asn His Gln Tyr Arg Glu Ile Lys Ser Gly Ser Val Asp
                245                 250                 255

Gly Ser Asn Ala Asn Ala Tyr Phe Gly Tyr Ser Thr Pro Trp Gly Tyr
            260                 265                 270

Phe Asp Phe Asn Arg Phe His Ser His Trp Ser Pro Arg Asp Trp Gln
        275                 280                 285

Arg Leu Ile Asn Asn Tyr Trp Gly Phe Arg Pro Arg Ser Leu Arg Val
    290                 295                 300

Lys Ile Phe Asn Ile Gln Val Lys Glu Val Thr Val Gln Asp Ser Thr
305                 310                 315                 320

Thr Thr Ile Ala Asn Asn Leu Thr Ser Thr Val Gln Val Phe Thr Asp
```

```
                325                 330                 335

Asp Asp Tyr Gln Leu Pro Tyr Val Val Gly Asn Gly Thr Glu Gly Cys
            340                 345                 350

Leu Pro Ala Phe Pro Pro Gln Val Phe Thr Leu Pro Gln Tyr Gly Tyr
        355                 360                 365

Ala Thr Leu Asn Arg Asp Asn Thr Glu Asn Pro Thr Glu Arg Ser Ser
    370                 375                 380

Phe Phe Cys Leu Glu Tyr Phe Pro Ser Lys Met Leu Arg Thr Gly Asn
385                 390                 395                 400

Asn Phe Glu Phe Thr Tyr Asn Phe Glu Glu Val Pro Phe His Ser Ser
                405                 410                 415

Phe Ala Pro Ser Gln Asn Leu Phe Lys Leu Ala Asn Pro Leu Val Asp
            420                 425                 430

Gln Tyr Leu Tyr Arg Phe Val Ser Thr Asn Asn Thr Gly Gly Val Gln
        435                 440                 445

Phe Asn Lys Asn Leu Ala Gly Arg Tyr Ala Asn Thr Tyr Lys Asn Trp
    450                 455                 460

Phe Pro Gly Pro Met Gly Arg Thr Gln Gly Trp Asn Leu Gly Ser Gly
465                 470                 475                 480

Val Asn Arg Ala Ser Val Ser Ala Phe Ala Thr Thr Asn Arg Met Glu
                485                 490                 495

Leu Glu Gly Ala Ser Tyr Gln Val Pro Pro Gln Pro Asn Gly Met Thr
            500                 505                 510

Asn Asn Leu Gln Gly Ser Asn Thr Tyr Ala Leu Glu Asn Thr Met Ile
        515                 520                 525

Phe Asn Ser Gln Pro Ala Asn Pro Gly Thr Thr Ala Thr Tyr Leu Glu
    530                 535                 540

Gly Asn Met Leu Ile Thr Ser Glu Ser Glu Thr Gln Pro Val Asn Arg
545                 550                 555                 560

Val Ala Tyr Asn Val Gly Gly Gln Met Ala Thr Asn Asn Gln Ser Ser
                565                 570                 575

Thr Thr Ala Pro Ala Thr Gly Thr Tyr Asn Leu Gln Glu Ile Val Pro
            580                 585                 590

Gly Ser Val Trp Met Glu Arg Asp Val Tyr Leu Gln Gly Pro Ile Trp
        595                 600                 605

Ala Lys Ile Pro Glu Thr Gly Ala His Phe His Pro Ser Pro Ala Met
    610                 615                 620

Gly Gly Phe Gly Leu Lys His Pro Pro Pro Met Met Leu Ile Lys Asn
625                 630                 635                 640

Thr Pro Val Pro Gly Asn Ile Thr Ser Phe Ser Asp Val Pro Val Ser
                645                 650                 655

Ser Phe Ile Thr Gln Tyr Ser Thr Gly Gln Val Thr Val Glu Met Glu
            660                 665                 670

Trp Glu Leu Lys Lys Glu Asn Ser Lys Arg Trp Asn Pro Glu Ile Gln
        675                 680                 685

Tyr Thr Asn Asn Tyr Asn Asp Pro Gln Phe Val Asp Phe Ala Pro Asp
    690                 695                 700

Ser Thr Gly Glu Tyr Arg Thr Thr Arg Pro Ile Gly Thr Arg Tyr Leu
705                 710                 715                 720

Thr Arg Pro Leu

<210> SEQ ID NO 7
<211> LENGTH: 736
```

<212> TYPE: PRT
<213> ORGANISM: Parvovirus adeno-associated virus

<400> SEQUENCE: 7

```
Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Gln Ser Pro Gln Glu Pro Asp Ser Ser Ser Gly Ile Gly
145                 150                 155                 160

Lys Thr Gly Gln Gln Pro Ala Lys Lys Arg Leu Asn Phe Gly Gln Thr
                165                 170                 175

Gly Asp Ser Glu Ser Val Pro Asp Pro Gln Pro Leu Gly Glu Pro Pro
            180                 185                 190

Ala Thr Pro Ala Ala Val Gly Pro Thr Thr Met Ala Ser Gly Gly Gly
        195                 200                 205

Ala Pro Met Ala Asp Asn Asn Glu Gly Ala Asp Gly Val Gly Asn Ala
    210                 215                 220

Ser Gly Asn Trp His Cys Asp Ser Thr Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Ser Ala Ser Thr Gly Ala Ser Asn Asp Asn His
            260                 265                 270

Tyr Phe Gly Tyr Ser Thr Pro Trp Gly Tyr Phe Asp Phe Asn Arg Phe
        275                 280                 285

His Cys His Phe Ser Pro Arg Asp Trp Gln Arg Leu Ile Asn Asn Asn
    290                 295                 300

Trp Gly Phe Arg Pro Lys Arg Leu Asn Phe Lys Leu Phe Asn Ile Gln
305                 310                 315                 320

Val Lys Glu Val Thr Thr Asn Asp Gly Val Thr Thr Ile Ala Asn Asn
                325                 330                 335

Leu Thr Ser Thr Val Gln Val Phe Ser Asp Ser Glu Tyr Gln Leu Pro
            340                 345                 350

Tyr Val Leu Gly Ser Ala His Gln Gly Cys Leu Pro Pro Phe Pro Ala
        355                 360                 365

Asp Val Phe Met Ile Pro Gln Tyr Gly Tyr Leu Thr Leu Asn Asn Gly
    370                 375                 380

Ser Gln Ala Val Gly Arg Ser Ser Phe Tyr Cys Leu Glu Tyr Phe Pro
385                 390                 395                 400
```

Ser Gln Met Leu Arg Thr Gly Asn Asn Phe Thr Phe Ser Tyr Thr Phe
405 410 415

Glu Asp Val Pro Phe His Ser Ser Tyr Ala His Ser Gln Ser Leu Asp
420 425 430

Arg Leu Met Asn Pro Leu Ile Asp Gln Tyr Leu Tyr Tyr Leu Asn Arg
435 440 445

Thr Gln Asn Gln Ser Gly Ser Ala Gln Asn Lys Asp Leu Leu Phe Ser
450 455 460

Arg Gly Ser Pro Ala Gly Met Ser Val Gln Pro Lys Asn Trp Leu Pro
465 470 475 480

Gly Pro Cys Tyr Arg Gln Gln Arg Val Ser Lys Thr Lys Thr Asp Asn
485 490 495

Asn Asn Ser Asn Phe Thr Trp Thr Gly Ala Ser Lys Tyr Asn Leu Asn
500 505 510

Gly Arg Glu Ser Ile Ile Asn Pro Gly Thr Ala Met Ala Ser His Lys
515 520 525

Asp Asp Lys Asp Lys Phe Phe Pro Met Ser Gly Val Met Ile Phe Gly
530 535 540

Lys Glu Ser Ala Gly Ala Ser Asn Thr Ala Leu Asp Asn Val Met Ile
545 550 555 560

Thr Asp Glu Glu Glu Ile Lys Ala Thr Asn Pro Val Ala Thr Glu Arg
565 570 575

Phe Gly Thr Val Ala Val Asn Leu Gln Ser Ser Ser Thr Asp Pro Ala
580 585 590

Thr Gly Asp Val His Val Met Gly Ala Leu Pro Gly Met Val Trp Gln
595 600 605

Asp Arg Asp Val Tyr Leu Gln Gly Pro Ile Trp Ala Lys Ile Pro His
610 615 620

Thr Asp Gly His Phe His Pro Ser Pro Leu Met Gly Gly Phe Gly Leu
625 630 635 640

Lys His Pro Pro Pro Gln Ile Leu Ile Lys Asn Thr Pro Val Pro Ala
645 650 655

Asn Pro Pro Ala Glu Phe Ser Ala Thr Lys Phe Ala Ser Phe Ile Thr
660 665 670

Gln Tyr Ser Thr Gly Gln Val Ser Val Glu Ile Glu Trp Glu Leu Gln
675 680 685

Lys Glu Asn Ser Lys Arg Trp Asn Pro Glu Val Gln Tyr Thr Ser Asn
690 695 700

Tyr Ala Lys Ser Ala Asn Val Asp Phe Thr Val Asp Asn Asn Gly Leu
705 710 715 720

Tyr Thr Glu Pro Arg Pro Ile Gly Thr Arg Tyr Leu Thr Arg Pro Leu
725 730 735

<210> SEQ ID NO 8
<211> LENGTH: 737
<212> TYPE: PRT
<213> ORGANISM: Parvovirus adeno-associated virus

<400> SEQUENCE: 8

Met Ala Ala Asp Gly Tyr Leu Pro Asp Trp Leu Glu Asp Asn Leu Ser
1 5 10 15

Glu Gly Ile Arg Glu Trp Trp Asp Leu Lys Pro Gly Ala Pro Lys Pro
20 25 30

Lys Ala Asn Gln Gln Lys Gln Asp Asn Gly Arg Gly Leu Val Leu Pro

```
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Ala Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Ser Val Gly Ser Gly Thr Val Ala Ala Gly Gly
        195                 200                 205

Gly Ala Pro Met Ala Asp Asn Asn Glu Gly Ala Asp Gly Val Gly Asn
    210                 215                 220

Ala Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Ser Glu Thr Ala Gly Ser Thr Asn Asp Asn
            260                 265                 270

Thr Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Lys Leu Arg Phe Lys Leu Phe Asn Ile
305                 310                 315                 320

Gln Val Lys Glu Val Thr Thr Asn Asp Gly Val Thr Thr Ile Ala Asn
                325                 330                 335

Asn Leu Thr Ser Thr Ile Gln Val Phe Ser Asp Ser Glu Tyr Gln Leu
            340                 345                 350

Pro Tyr Val Leu Gly Ser Ala His Gln Gly Cys Leu Pro Pro Phe Pro
        355                 360                 365

Ala Asp Val Phe Met Ile Pro Gln Tyr Gly Tyr Leu Thr Leu Asn Asn
    370                 375                 380

Gly Ser Gln Ser Val Gly Arg Ser Ser Phe Tyr Cys Leu Glu Tyr Phe
385                 390                 395                 400

Pro Ser Gln Met Leu Arg Thr Gly Asn Asn Phe Glu Phe Ser Tyr Ser
                405                 410                 415

Phe Glu Asp Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ala
        435                 440                 445

Arg Thr Gln Ser Asn Pro Gly Gly Thr Ala Gly Asn Arg Glu Leu Gln
    450                 455                 460
```

Phe Tyr Gln Gly Gly Pro Ser Thr Met Ala Glu Gln Ala Lys Asn Trp
465 470 475 480

Leu Pro Gly Pro Cys Phe Arg Gln Gln Arg Val Ser Lys Thr Leu Asp
485 490 495

Gln Asn Asn Asn Ser Asn Phe Ala Trp Thr Gly Ala Thr Lys Tyr His
500 505 510

Leu Asn Gly Arg Asn Ser Leu Val Asn Pro Gly Val Ala Met Ala Thr
515 520 525

His Lys Asp Asp Glu Asp Arg Phe Phe Pro Ser Ser Gly Val Leu Ile
530 535 540

Phe Gly Lys Thr Gly Ala Thr Asn Lys Thr Thr Leu Glu Asn Val Leu
545 550 555 560

Met Thr Asn Glu Glu Glu Ile Arg Pro Thr Asn Pro Val Ala Thr Glu
565 570 575

Glu Tyr Gly Ile Val Ser Ser Asn Leu Gln Ala Ala Asn Thr Ala Ala
580 585 590

Gln Thr Gln Val Val Asn Asn Gln Gly Ala Leu Pro Gly Met Val Trp
595 600 605

Gln Asn Arg Asp Val Tyr Leu Gln Gly Pro Ile Trp Ala Lys Ile Pro
610 615 620

His Thr Asp Gly Asn Phe His Pro Ser Pro Leu Met Gly Gly Phe Gly
625 630 635 640

Leu Lys His Pro Pro Pro Gln Ile Leu Ile Lys Asn Thr Pro Val Pro
645 650 655

Ala Asn Pro Pro Glu Val Phe Thr Pro Ala Lys Phe Ala Ser Phe Ile
660 665 670

Thr Gln Tyr Ser Thr Gly Gln Val Ser Val Glu Ile Glu Trp Glu Leu
675 680 685

Gln Lys Glu Asn Ser Lys Arg Trp Asn Pro Glu Ile Gln Tyr Thr Ser
690 695 700

Asn Phe Glu Lys Gln Thr Gly Val Asp Phe Ala Val Asp Ser Gln Gly
705 710 715 720

Val Tyr Ser Glu Pro Arg Pro Ile Gly Thr Arg Tyr Leu Thr Arg Asn
725 730 735

Leu

<210> SEQ ID NO 9
<211> LENGTH: 738
<212> TYPE: PRT
<213> ORGANISM: Parvovirus adeno-associated virus

<400> SEQUENCE: 9

Met Ala Ala Asp Gly Tyr Leu Pro Asp Trp Leu Glu Asp Asn Leu Ser
1 5 10 15

Glu Gly Ile Arg Glu Trp Trp Ala Leu Lys Pro Gly Ala Pro Lys Pro
20 25 30

Lys Ala Asn Gln Gln Lys Gln Asp Asp Gly Arg Gly Leu Val Leu Pro
35 40 45

Gly Tyr Lys Tyr Leu Gly Pro Phe Asn Gly Leu Asp Lys Gly Glu Pro
50 55 60

Val Asn Ala Ala Asp Ala Ala Ala Leu Glu His Asp Lys Ala Tyr Asp
65 70 75 80

Gln Gln Leu Gln Ala Gly Asp Asn Pro Tyr Leu Arg Tyr Asn His Ala
85 90 95

```
Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Arg Lys Arg Leu Asn Phe Gly Gln
                165                 170                 175

Thr Gly Asp Ser Glu Ser Val Pro Asp Pro Gln Pro Leu Gly Glu Pro
            180                 185                 190

Pro Ala Ala Pro Ser Gly Val Gly Pro Asn Thr Met Ala Ala Gly Gly
        195                 200                 205

Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ala Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Ser Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Gln Phe Thr Tyr
                405                 410                 415

Thr Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Thr Thr Gly Gly Thr Ala Asn Thr Gln Thr Leu Gly
    450                 455                 460

Phe Ser Gln Gly Gly Pro Asn Thr Met Ala Asn Gln Ala Lys Asn Trp
465                 470                 475                 480

Leu Pro Gly Pro Cys Tyr Arg Gln Gln Arg Val Ser Thr Thr Thr Gly
                485                 490                 495

Gln Asn Asn Asn Ser Asn Phe Ala Trp Thr Ala Gly Thr Lys Tyr His
            500                 505                 510
```

```
Leu Asn Gly Arg Asn Ser Leu Ala Asn Pro Gly Ile Ala Met Ala Thr
        515                 520                 525

His Lys Asp Asp Glu Glu Arg Phe Phe Pro Ser Asn Gly Ile Leu Ile
    530                 535                 540

Phe Gly Lys Gln Asn Ala Ala Arg Asp Asn Ala Asp Tyr Ser Asp Val
545                 550                 555                 560

Met Leu Thr Ser Glu Glu Glu Ile Lys Thr Thr Asn Pro Val Ala Thr
                565                 570                 575

Glu Glu Tyr Gly Ile Val Ala Asp Asn Leu Gln Gln Gln Asn Thr Ala
            580                 585                 590

Pro Gln Ile Gly Thr Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Asn Gln Ser Lys Leu Asn Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Ser Val Asp Phe Ala Val Asn Thr Glu
705                 710                 715                 720

Gly Val Tyr Ser Glu Pro Arg Pro Ile Gly Thr Arg Tyr Leu Thr Arg
                725                 730                 735

Asn Leu


<210> SEQ ID NO 10
<211> LENGTH: 736
<212> TYPE: PRT
<213> ORGANISM: Parvovirus adeno-associated virus

<400> SEQUENCE: 10

Met Ala Ala Asp Gly Tyr Leu Pro Asp Trp Leu Glu Asp Asn Leu Ser
1               5                   10                  15

Glu Gly Ile Arg Glu Trp Trp Ala Leu Lys Pro Gly Ala Pro Gln Pro
            20                  25                  30

Lys Ala Asn Gln Gln His Gln Asp Asn Ala Arg Gly Leu Val Leu Pro
        35                  40                  45

Gly Tyr Lys Tyr Leu Gly Pro Gly Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Lys Tyr Asn His Ala
                85                  90                  95

Asp Ala Glu Phe Gln Glu Arg Leu Lys Glu Asp Thr Ser Phe Gly Gly
            100                 105                 110

Asn Leu Gly Arg Ala Val Phe Gln Ala Lys Lys Arg Leu Leu Glu Pro
        115                 120                 125

Leu Gly Leu Val Glu Glu Ala Ala Lys Thr Ala Pro Gly Lys Lys Arg
    130                 135                 140
```

-continued

```
Pro Val Glu Gln Ser Pro Gln Glu Pro Asp Ser Ser Ala Gly Ile Gly
145                 150                 155                 160

Lys Ser Gly Ala Gln Pro Ala Lys Lys Arg Leu Asn Phe Gly Gln Thr
                165                 170                 175

Gly Asp Thr Glu Ser Val Pro Asp Pro Gln Pro Ile Gly Glu Pro Pro
            180                 185                 190

Ala Ala Pro Ser Gly Val Gly Ser Leu Thr Met Ala Ser Gly Gly Gly
        195                 200                 205

Ala Pro Val Ala Asp Asn Asn Glu Gly Ala Asp Gly Val Gly Ser Ser
    210                 215                 220

Ser Gly Asn Trp His Cys Asp Ser Gln Trp Leu Gly Asp Arg Val Ile
225                 230                 235                 240

Thr Thr Ser Thr Arg Thr Trp Ala Leu Pro Thr Tyr Asn Asn His Leu
                245                 250                 255

Tyr Lys Gln Ile Ser Asn Ser Thr Ser Gly Gly Ser Ser Asn Asp Asn
            260                 265                 270

Ala Tyr Phe Gly Tyr Ser Thr Pro Trp Gly Tyr Phe Asp Phe Asn Arg
        275                 280                 285

Phe His Cys His Phe Ser Pro Arg Asp Trp Gln Arg Leu Ile Asn Asn
    290                 295                 300

Asn Trp Gly Phe Arg Pro Lys Arg Leu Asn Phe Lys Leu Phe Asn Ile
305                 310                 315                 320

Gln Val Lys Glu Val Thr Asp Asn Asn Gly Val Lys Thr Ile Ala Asn
                325                 330                 335

Asn Leu Thr Ser Thr Val Gln Val Phe Thr Asp Ser Asp Tyr Gln Leu
            340                 345                 350

Pro Tyr Val Leu Gly Ser Ala His Glu Gly Cys Leu Pro Pro Phe Pro
        355                 360                 365

Ala Asp Val Phe Met Ile Pro Gln Tyr Gly Tyr Leu Thr Leu Asn Asp
    370                 375                 380

Gly Ser Gln Ala Val Gly Arg Ser Ser Phe Tyr Cys Leu Glu Tyr Phe
385                 390                 395                 400

Pro Ser Gln Met Leu Arg Thr Gly Asn Asn Phe Gln Phe Ser Tyr Glu
                405                 410                 415

Phe Glu Asn Val Pro Phe His Ser Ser Tyr Ala His Ser Gln Ser Leu
            420                 425                 430

Asp Arg Leu Met Asn Pro Leu Ile Asp Gln Tyr Leu Tyr Tyr Leu Ser
        435                 440                 445

Lys Thr Ile Asn Gly Ser Gly Gln Asn Gln Gln Thr Leu Lys Phe Ser
    450                 455                 460

Val Ala Gly Pro Ser Asn Met Ala Val Gln Gly Arg Asn Tyr Ile Pro
465                 470                 475                 480

Gly Pro Ser Tyr Arg Gln Gln Arg Val Ser Thr Thr Val Thr Gln Asn
                485                 490                 495

Asn Asn Ser Glu Phe Ala Trp Pro Gly Ala Ser Ser Trp Ala Leu Asn
            500                 505                 510

Gly Arg Asn Ser Leu Met Asn Pro Gly Pro Ala Met Ala Ser His Lys
        515                 520                 525

Glu Gly Glu Asp Arg Phe Phe Pro Leu Ser Gly Ser Leu Ile Phe Gly
    530                 535                 540

Lys Gln Gly Thr Gly Arg Asp Asn Val Asp Ala Asp Lys Val Met Ile
545                 550                 555                 560

Thr Asn Glu Glu Glu Ile Lys Thr Thr Asn Pro Val Ala Thr Glu Ser
```

```
                565                 570                 575

Tyr Gly Gln Val Ala Thr Asn His Gln Ser Ala Gln Ala Gln Ala Gln
            580                 585                 590

Thr Gly Trp Val Gln Asn Gln Gly Ile Leu Pro Gly Met Val Trp Gln
        595                 600                 605

Asp Arg Asp Val Tyr Leu Gln Gly Pro Ile Trp Ala Lys Ile Pro His
    610                 615                 620

Thr Asp Gly Asn Phe His Pro Ser Pro Leu Met Gly Gly Phe Gly Met
625                 630                 635                 640

Lys His Pro Pro Pro Gln Ile Leu Ile Lys Asn Thr Pro Val Pro Ala
                645                 650                 655

Asp Pro Pro Thr Ala Phe Asn Lys Asp Lys Leu Asn Ser Phe Ile Thr
            660                 665                 670

Gln Tyr Ser Thr Gly Gln Val Ser Val Glu Ile Glu Trp Glu Leu Gln
        675                 680                 685

Lys Glu Asn Ser Lys Arg Trp Asn Pro Glu Ile Gln Tyr Thr Ser Asn
    690                 695                 700

Tyr Tyr Lys Ser Asn Asn Val Glu Phe Ala Val Asn Thr Glu Gly Val
705                 710                 715                 720

Tyr Ser Glu Pro Arg Pro Ile Gly Thr Arg Tyr Leu Thr Arg Asn Leu
                725                 730                 735


<210> SEQ ID NO 11
<211> LENGTH: 738
<212> TYPE: PRT
<213> ORGANISM: Parvovirus adeno-associated virus

<400> SEQUENCE: 11

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Val Glu Pro Ser Pro Gln Arg Ser Pro Asp Ser Ser Thr Gly Ile
145                 150                 155                 160

Gly Lys Lys Gly Gln Gln Pro Ala Lys Lys Arg Leu Asn Phe Gly Gln
                165                 170                 175

Thr Gly Asp Ser Glu Ser Val Pro Asp Pro Gln Pro Ile Gly Glu Pro
            180                 185                 190

Pro Ala Gly Pro Ser Gly Leu Gly Ser Gly Thr Met Ala Ala Gly Gly
        195                 200                 205
```

-continued

```
Gly Ala Pro Met Ala Asp Asn Asn Glu Gly Ala Asp Gly Val Gly Ser
    210                 215                 220

Ser Ser Gly Asn Trp His Cys Asp Ser Thr Trp Leu Gly Asp Arg Val
225                 230                 235                 240

Ile Thr Thr Ser Thr Arg Thr Trp Ala Leu Pro Thr Tyr Asn Asn His
                245                 250                 255

Leu Tyr Lys Gln Ile Ser Asn Gly Thr Ser Gly Gly Ser Thr Asn Asp
            260                 265                 270

Asn Thr Tyr Phe Gly Tyr Ser Thr Pro Trp Gly Tyr Phe Asp Phe Asn
        275                 280                 285

Arg Phe His Cys His Phe Ser Pro Arg Asp Trp Gln Arg Leu Ile Asn
    290                 295                 300

Asn Asn Trp Gly Phe Arg Pro Lys Arg Leu Asn Phe Lys Leu Phe Asn
305                 310                 315                 320

Ile Gln Val Lys Glu Val Thr Gln Asn Glu Gly Thr Lys Thr Ile Ala
                325                 330                 335

Asn Asn Leu Thr Ser Thr Ile Gln Val Phe Thr Asp Ser Glu Tyr Gln
            340                 345                 350

Leu Pro Tyr Val Leu Gly Ser Ala His Gln Gly Cys Leu Pro Pro Phe
        355                 360                 365

Pro Ala Asp Val Phe Met Ile Pro Gln Tyr Gly Tyr Leu Thr Leu Asn
    370                 375                 380

Asn Gly Ser Gln Ala Val Gly Arg Ser Ser Phe Tyr Cys Leu Glu Tyr
385                 390                 395                 400

Phe Pro Ser Gln Met Leu Arg Thr Gly Asn Asn Phe Glu Phe Ser Tyr
                405                 410                 415

Gln Phe Glu Asp Val Pro Phe His Ser Ser Tyr Ala His Ser Gln Ser
            420                 425                 430

Leu Asp Arg Leu Met Asn Pro Leu Ile Asp Gln Tyr Leu Tyr Tyr Leu
        435                 440                 445

Ser Arg Thr Gln Ser Thr Gly Gly Thr Ala Gly Thr Gln Gln Leu Leu
    450                 455                 460

Phe Ser Gln Ala Gly Pro Asn Asn Met Ser Ala Gln Ala Lys Asn Trp
465                 470                 475                 480

Leu Pro Gly Pro Cys Tyr Arg Gln Gln Arg Val Ser Thr Thr Leu Ser
                485                 490                 495

Gln Asn Asn Asn Ser Asn Phe Ala Trp Thr Gly Ala Thr Lys Tyr His
            500                 505                 510

Leu Asn Gly Arg Asp Ser Leu Val Asn Pro Gly Val Ala Met Ala Thr
        515                 520                 525

His Lys Asp Asp Glu Glu Arg Phe Phe Pro Ser Ser Gly Val Leu Met
    530                 535                 540

Phe Gly Lys Gln Gly Ala Gly Lys Asp Asn Val Asp Tyr Ser Ser Val
545                 550                 555                 560

Met Leu Thr Ser Glu Glu Glu Ile Lys Thr Thr Asn Pro Val Ala Thr
                565                 570                 575

Glu Gln Tyr Gly Val Val Ala Asp Asn Leu Gln Gln Gln Asn Ala Ala
            580                 585                 590

Pro Ile Val Gly Ala Val Asn Ser Gln Gly Ala Leu Pro Gly Met Val
        595                 600                 605

Trp Gln Asn Arg Asp Val Tyr Leu Gln Gly Pro Ile Trp Ala Lys Ile
    610                 615                 620

Pro His Thr Asp Gly Asn Phe His Pro Ser Pro Leu Met Gly Gly Phe
```

```
625                 630                 635                 640

Gly Leu Lys His Pro Pro Pro Gln Ile Leu Ile Lys Asn Thr Pro Val
                645                 650                 655

Pro Ala Asp Pro Pro Thr Thr Phe Ser Gln Ala Lys Leu Ala Ser Phe
            660                 665                 670

Ile Thr Gln Tyr Ser Thr Gly Gln Val Ser Val Glu Ile Glu Trp Glu
        675                 680                 685

Leu Gln Lys Glu Asn Ser Lys Arg Trp Asn Pro Glu Ile Gln Tyr Thr
    690                 695                 700

Ser Asn Tyr Tyr Lys Ser Thr Asn Val Asp Phe Ala Val Asn Thr Asp
705                 710                 715                 720

Gly Thr Tyr Ser Glu Pro Arg Pro Ile Gly Thr Arg Tyr Leu Thr Arg
                725                 730                 735

Asn Leu


<210> SEQ ID NO 12
<211> LENGTH: 733
<212> TYPE: PRT
<213> ORGANISM: Parvovirus adeno-associated virus

<400> SEQUENCE: 12

Met Ala Ala Asp Gly Tyr Leu Pro Asp Trp Leu Glu Asp Asn Leu Ser
1               5                   10                  15

Glu Gly Ile Arg Glu Trp Trp Asp Leu Lys Pro Gly Ala Pro Lys Pro
            20                  25                  30

Lys Ala Asn Gln Gln Lys Gln Asp Asp Gly Arg Gly Leu Val Leu Pro
        35                  40                  45

Gly Tyr Lys Tyr Leu Gly Pro Phe Asn Gly Leu Asp Lys Gly Glu Pro
    50                  55                  60

Val Asn Ala Ala Asp Ala Ala Ala Leu Glu His Asp Lys Ala Tyr Asp
65                  70                  75                  80

Gln Gln Leu Lys Ala Gly Asp Asn Pro Tyr Leu Arg Tyr Asn His Ala
                85                  90                  95

Asp Ala Glu Phe Gln Glu Arg Leu Gln Glu Asp Thr Ser Phe Gly Gly
            100                 105                 110

Asn Leu Gly Arg Ala Val Phe Gln Ala Lys Lys Arg Val Leu Glu Pro
        115                 120                 125

Leu Gly Leu Val Glu Glu Gly Ala Lys Thr Ala Pro Gly Lys Lys Arg
    130                 135                 140

Pro Leu Glu Ser Pro Gln Glu Pro Asp Ser Ser Ser Gly Ile Gly Lys
145                 150                 155                 160

Lys Gly Lys Gln Pro Ala Arg Lys Arg Leu Asn Phe Glu Glu Asp Thr
                165                 170                 175

Gly Ala Gly Asp Gly Pro Pro Glu Gly Ser Asp Thr Ser Ala Met Ser
            180                 185                 190

Ser Asp Ile Glu Met Arg Ala Ala Pro Gly Gly Asn Ala Val Asp Ala
        195                 200                 205

Gly Gln Gly Ser Asp Gly Val Gly Asn Ala Ser Gly Asp Trp His Cys
    210                 215                 220

Asp Ser Thr Trp Ser Glu Gly Lys Val Thr Thr Thr Ser Thr Arg Thr
225                 230                 235                 240

Trp Val Leu Pro Thr Tyr Asn Asn His Leu Tyr Leu Arg Leu Gly Thr
                245                 250                 255

Thr Ser Ser Ser Asn Thr Tyr Asn Gly Phe Ser Thr Pro Trp Gly Tyr
```

-continued

```
            260                 265                 270

Phe Asp Phe Asn Arg Phe His Cys His Phe Ser Pro Arg Asp Trp Gln
        275                 280                 285

Arg Leu Ile Asn Asn Asn Trp Gly Leu Arg Pro Lys Ala Met Arg Val
    290                 295                 300

Lys Ile Phe Asn Ile Gln Val Lys Glu Val Thr Thr Ser Asn Gly Glu
305                 310                 315                 320

Thr Thr Val Ala Asn Asn Leu Thr Ser Thr Val Gln Ile Phe Ala Asp
                325                 330                 335

Ser Ser Tyr Glu Leu Pro Tyr Val Met Asp Ala Gly Gln Glu Gly Ser
            340                 345                 350

Leu Pro Pro Phe Pro Asn Asp Val Phe Met Val Pro Gln Tyr Gly Tyr
        355                 360                 365

Cys Gly Ile Val Thr Gly Glu Asn Gln Asn Gln Thr Asp Arg Asn Ala
    370                 375                 380

Phe Tyr Cys Leu Glu Tyr Phe Pro Ser Gln Met Leu Arg Thr Gly Asn
385                 390                 395                 400

Asn Phe Glu Met Ala Tyr Asn Phe Glu Lys Val Pro Phe His Ser Met
                405                 410                 415

Tyr Ala His Ser Gln Ser Leu Asp Arg Leu Met Asn Pro Leu Leu Asp
            420                 425                 430

Gln Tyr Leu Trp His Leu Gln Ser Thr Thr Ser Gly Glu Thr Leu Asn
        435                 440                 445

Gln Gly Asn Ala Ala Thr Thr Phe Gly Lys Ile Arg Ser Gly Asp Phe
    450                 455                 460

Ala Phe Tyr Arg Lys Asn Trp Leu Pro Gly Pro Cys Val Lys Gln Gln
465                 470                 475                 480

Arg Phe Ser Lys Thr Ala Ser Gln Asn Tyr Lys Ile Pro Ala Ser Gly
                485                 490                 495

Gly Asn Ala Leu Leu Lys Tyr Asp Thr His Tyr Thr Leu Asn Asn Arg
            500                 505                 510

Trp Ser Asn Ile Ala Pro Gly Pro Pro Met Ala Thr Ala Gly Pro Ser
        515                 520                 525

Asp Gly Asp Phe Ser Asn Ala Gln Leu Ile Phe Pro Gly Pro Ser Val
    530                 535                 540

Thr Gly Asn Thr Thr Thr Ser Ala Asn Asn Leu Leu Phe Thr Ser Glu
545                 550                 555                 560

Glu Glu Ile Ala Ala Thr Asn Pro Arg Asp Thr Asp Met Phe Gly Gln
                565                 570                 575

Ile Ala Asp Asn Asn Gln Asn Ala Thr Thr Ala Pro Ile Thr Gly Asn
            580                 585                 590

Val Thr Ala Met Gly Val Leu Pro Gly Met Val Trp Gln Asn Arg Asp
        595                 600                 605

Ile Tyr Tyr Gln Gly Pro Ile Trp Ala Lys Ile Pro His Ala Asp Gly
    610                 615                 620

His Phe His Pro Ser Pro Leu Ile Gly Gly Phe Gly Leu Lys His Pro
625                 630                 635                 640

Pro Pro Gln Ile Phe Ile Lys Asn Thr Pro Val Pro Ala Asn Pro Ala
                645                 650                 655

Thr Thr Phe Thr Ala Ala Arg Val Asp Ser Phe Ile Thr Gln Tyr Ser
            660                 665                 670

Thr Gly Gln Val Ala Val Gln Ile Glu Trp Glu Ile Glu Lys Glu Arg
        675                 680                 685
```

Ser Lys Arg Trp Asn Pro Glu Val Gln Phe Thr Ser Asn Tyr Gly Asn
690 695 700

Gln Ser Ser Met Leu Trp Ala Pro Asp Thr Thr Gly Lys Tyr Thr Glu
705 710 715 720

Pro Arg Val Ile Gly Ser Arg Tyr Leu Thr Asn His Leu
725 730

<210> SEQ ID NO 13
<211> LENGTH: 341
<212> TYPE: PRT
<213> ORGANISM: Streptococcus pyogenes

<400> SEQUENCE: 13

Met Arg Lys Arg Cys Tyr Ser Thr Ser Ala Ala Val Leu Ala Ala Val
1 5 10 15

Thr Leu Phe Ala Leu Ser Val Asp Arg Gly Val Ile Ala Asp Ser Phe
20 25 30

Ser Ala Asn Gln Glu Ile Arg Tyr Ser Glu Val Thr Pro Tyr His Val
35 40 45

Thr Ser Val Trp Thr Lys Gly Val Thr Pro Pro Ala Lys Phe Thr Gln
50 55 60

Gly Glu Asp Val Phe His Ala Pro Tyr Val Ala Asn Gln Gly Trp Tyr
65 70 75 80

Asp Ile Thr Lys Thr Phe Asn Gly Lys Asp Asp Leu Leu Cys Gly Ala
85 90 95

Ala Thr Ala Gly Asn Met Leu His Trp Trp Phe Asp Gln Asn Lys Glu
100 105 110

Lys Ile Glu Ala Tyr Leu Lys Lys His Pro Asp Lys Gln Lys Ile Met
115 120 125

Phe Gly Asp Gln Glu Leu Leu Asp Val Arg Lys Val Ile Asn Thr Lys
130 135 140

Gly Asp Gln Thr Asn Ser Glu Leu Phe Asn Tyr Phe Arg Asp Lys Ala
145 150 155 160

Phe Pro Gly Leu Ser Ala Arg Arg Ile Gly Val Met Pro Asp Leu Val
165 170 175

Leu Asp Met Phe Ile Asn Gly Tyr Tyr Leu Asn Val Tyr Lys Thr Gln
180 185 190

Thr Thr Asp Val Asn Arg Thr Tyr Gln Glu Lys Asp Arg Arg Gly Gly
195 200 205

Ile Phe Asp Ala Val Phe Thr Arg Gly Asp Gln Ser Lys Leu Leu Thr
210 215 220

Ser Arg His Asp Phe Lys Glu Lys Asn Leu Lys Glu Ile Ser Asp Leu
225 230 235 240

Ile Lys Lys Glu Leu Thr Glu Gly Lys Ala Leu Gly Leu Ser His Thr
245 250 255

Tyr Ala Asn Val Arg Ile Asn His Val Ile Asn Leu Trp Gly Ala Asp
260 265 270

Phe Asp Ser Asn Gly Asn Leu Lys Ala Ile Tyr Val Thr Asp Ser Asp
275 280 285

Ser Asn Ala Ser Ile Gly Met Lys Lys Tyr Phe Val Gly Val Asn Ser
290 295 300

Ser Gly Lys Val Ala Ile Ser Ala Lys Glu Ile Lys Glu Asp Asn Ile
305 310 315 320

Gly Ala Gln Val Leu Gly Leu Phe Thr Leu Ser Thr Gly Gln Asp Ser 325 330 335

Trp Asn Gln Thr Asn
340

<210> SEQ ID NO 14
<211> LENGTH: 341
<212> TYPE: PRT
<213> ORGANISM: Streptococcus pyogenes

<400> SEQUENCE: 14

Met Arg Lys Arg Cys Tyr Ser Thr Ser Ala Ala Val Leu Ala Ala Val
1 5 10 15

Thr Leu Phe Ala Leu Ser Val Asp Arg Gly Val Ile Ala Asp Ser Phe
20 25 30

Ser Ala Asn Gln Glu Ile Arg Tyr Ser Glu Val Thr Pro Tyr His Val
35 40 45

Thr Ser Val Trp Thr Lys Gly Val Thr Pro Pro Ala Lys Phe Thr Gln
50 55 60

Gly Glu Asp Val Phe His Ala Pro Tyr Val Ala Asn Gln Gly Trp Tyr
65 70 75 80

Asp Ile Thr Lys Thr Phe Asn Gly Lys Asp Asp Leu Leu Cys Gly Ala
85 90 95

Ala Thr Ala Gly Asn Met Leu His Trp Trp Phe Asp Gln Asn Lys Glu
100 105 110

Lys Ile Glu Ala Tyr Leu Lys Lys His Pro Asp Lys Gln Lys Ile Met
115 120 125

Phe Gly Asp Gln Glu Leu Leu Asp Val Arg Lys Val Ile Asn Thr Lys
130 135 140

Gly Asp Gln Thr Asn Ser Glu Leu Phe Asn Tyr Phe Arg Asp Lys Ala
145 150 155 160

Phe Pro Gly Leu Ser Ala Arg Arg Ile Gly Val Met Pro Asp Leu Val
165 170 175

Leu Asp Met Phe Ile Asn Gly Tyr Tyr Leu Asn Val Tyr Lys Thr Gln
180 185 190

Thr Thr Asp Val Asn Arg Thr Tyr Gln Glu Lys Asp Arg Arg Gly Gly
195 200 205

Ile Phe Asp Ala Val Phe Thr Arg Gly Asp Gln Ser Lys Leu Leu Thr
210 215 220

Ser Arg His Asp Phe Lys Glu Lys Asn Leu Lys Glu Ile Ser Asp Leu
225 230 235 240

Ile Lys Lys Glu Leu Thr Glu Gly Lys Ala Leu Gly Leu Ser His Thr
245 250 255

Tyr Ala Asn Val Arg Ile Asn His Val Ile Asn Leu Trp Gly Ala Asp
260 265 270

Phe Asp Ser Asn Gly Asn Leu Lys Ala Ile Tyr Val Thr Asp Ser Asp
275 280 285

Ser Asn Ala Ser Ile Gly Met Lys Lys Tyr Phe Val Gly Val Asn Ser
290 295 300

Ser Gly Lys Val Ala Ile Ser Ala Lys Glu Ile Lys Glu Asp Asn Ile
305 310 315 320

Gly Ala Gln Val Leu Gly Leu Phe Thr Leu Ser Thr Gly Gln Asp Ser
325 330 335

Trp Asn Gln Thr Asn
340

<210> SEQ ID NO 15
<211> LENGTH: 339
<212> TYPE: PRT
<213> ORGANISM: Artificial Sequence
<220> FEATURE:
<223> OTHER INFORMATION: IgG degrading enzyme amino acid sequence

<400> SEQUENCE: 15

```
Met Arg Lys Arg Cys Tyr Ser Thr Ser Ala Ala Val Leu Ala Ala Val
1               5                   10                  15

Thr Leu Phe Val Leu Ser Val Asp Arg Gly Val Ile Ala Asp Ser Phe
            20                  25                  30

Ser Ala Asn Gln Glu Ile Arg Tyr Ser Glu Val Thr Pro Tyr His Val
        35                  40                  45

Thr Ser Val Trp Thr Lys Gly Val Thr Pro Pro Ala Asn Phe Thr Gln
    50                  55                  60

Gly Glu Asp Val Phe His Ala Pro Tyr Val Ala Asn Gln Gly Trp Tyr
65                  70                  75                  80

Asp Ile Thr Lys Thr Phe Asn Gly Lys Asp Asp Leu Leu Cys Gly Ala
                85                  90                  95

Ala Thr Ala Gly Asn Met Leu His Trp Trp Phe Asp Gln Asn Lys Asp
            100                 105                 110

Gln Ile Lys Arg Tyr Leu Glu Glu His Pro Glu Lys Gln Lys Ile Asn
        115                 120                 125

Phe Asn Gly Glu Gln Met Phe Asp Val Lys Glu Ala Ile Asp Thr Lys
    130                 135                 140

Asn His Gln Leu Asp Ser Lys Leu Phe Glu Tyr Phe Lys Glu Lys Ala
145                 150                 155                 160

Phe Pro Tyr Leu Ser Thr Lys His Leu Gly Val Phe Pro Asp His Val
                165                 170                 175

Ile Asp Met Phe Ile Asn Gly Tyr Arg Leu Ser Leu Thr Asn His Gly
            180                 185                 190

Pro Thr Pro Val Lys Glu Gly Ser Lys Asp Pro Arg Gly Gly Ile Phe
        195                 200                 205

Asp Ala Val Phe Thr Arg Gly Asp Gln Ser Lys Leu Leu Thr Ser Arg
    210                 215                 220

His Asp Phe Lys Glu Lys Asn Leu Lys Glu Ile Ser Asp Leu Ile Lys
225                 230                 235                 240

Lys Glu Leu Thr Glu Gly Lys Ala Leu Gly Leu Ser His Thr Tyr Ala
                245                 250                 255

Asn Val Arg Ile Asn His Val Ile Asn Leu Trp Gly Ala Asp Phe Asp
            260                 265                 270

Ser Asn Gly Asn Leu Lys Ala Ile Tyr Val Thr Asp Ser Asp Ser Asn
        275                 280                 285

Ala Ser Ile Gly Met Lys Lys Tyr Phe Val Gly Val Asn Ser Ala Gly
    290                 295                 300

Lys Val Ala Ile Ser Ala Lys Glu Ile Lys Glu Asp Asn Ile Gly Ala
305                 310                 315                 320

Gln Val Leu Gly Leu Phe Thr Leu Ser Thr Gly Gln Asp Ser Trp Asn
                325                 330                 335

Gln Thr Asn
```

<210> SEQ ID NO 16
<211> LENGTH: 310
<212> TYPE: PRT

<213> ORGANISM: Artificial Sequence
<220> FEATURE:
<223> OTHER INFORMATION: IgG degrading enzyme amino acid sequence

<400> SEQUENCE: 16

Asp Ser Phe Ser Ala Asn Gln Glu Ile Arg Tyr Ser Glu Val Thr Pro
1 5 10 15

Tyr His Val Thr Ser Val Trp Thr Lys Gly Val Thr Pro Pro Ala Asn
20 25 30

Phe Thr Gln Gly Glu Asp Val Phe His Ala Pro Tyr Val Ala Asn Gln
35 40 45

Gly Trp Tyr Asp Ile Thr Lys Thr Phe Asn Gly Lys Asp Asp Leu Leu
50 55 60

Cys Gly Ala Ala Thr Ala Gly Asn Met Leu His Trp Trp Phe Asp Gln
65 70 75 80

Asn Lys Asp Gln Ile Lys Arg Tyr Leu Glu Glu His Pro Glu Lys Gln
85 90 95

Lys Ile Asn Phe Asn Gly Glu Gln Met Phe Asp Val Lys Glu Ala Ile
100 105 110

Asp Thr Lys Asn His Gln Leu Asp Ser Lys Leu Phe Glu Tyr Phe Lys
115 120 125

Glu Lys Ala Phe Pro Tyr Leu Ser Thr Lys His Leu Gly Val Phe Pro
130 135 140

Asp His Val Ile Asp Met Phe Ile Asn Gly Tyr Arg Leu Ser Leu Thr
145 150 155 160

Asn His Gly Pro Thr Pro Val Lys Glu Gly Ser Lys Asp Pro Arg Gly
165 170 175

Gly Ile Phe Asp Ala Val Phe Thr Arg Gly Asp Gln Ser Lys Leu Leu
180 185 190

Thr Ser Arg His Asp Phe Lys Glu Lys Asn Leu Lys Glu Ile Ser Asp
195 200 205

Leu Ile Lys Lys Glu Leu Thr Glu Gly Lys Ala Leu Gly Leu Ser His
210 215 220

Thr Tyr Ala Asn Val Arg Ile Asn His Val Ile Asn Leu Trp Gly Ala
225 230 235 240

Asp Phe Asp Ser Asn Gly Asn Leu Lys Ala Ile Tyr Val Thr Asp Ser
245 250 255

Asp Ser Asn Ala Ser Ile Gly Met Lys Lys Tyr Phe Val Gly Val Asn
260 265 270

Ser Ala Gly Lys Val Ala Ile Ser Ala Lys Glu Ile Lys Glu Asp Asn
275 280 285

Ile Gly Ala Gln Val Leu Gly Leu Phe Thr Leu Ser Thr Gly Gln Asp
290 295 300

Ser Trp Asn Gln Thr Asn
305 310

<210> SEQ ID NO 17
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 17

Asp Ser Phe Ser Ala Asn Gln Glu Ile Arg Tyr Ser Glu Val Thr Pro
1 5 10 15

```
Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Arg Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300

Ser Trp Asn Gln Thr Asn
305                 310


<210> SEQ ID NO 18
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 18

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60
```

```
Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Lys Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Arg Gly Ser Lys Asp Pro Arg Gly
                165                 170                 175

Gly Ile Phe Asp Ala Val Phe Thr Arg Gly Asn Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300

Ser Trp Asn Gln Thr Asn
305                 310


<210> SEQ ID NO 19
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 19

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Arg Gly Glu Gln Met Phe Asp Val Lys Glu Ala Ile
            100                 105                 110
```

```
Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Lys Gly Ser Lys Asp Pro Arg Gly
                165                 170                 175

Gly Ile Phe Asp Ala Val Phe Thr Arg Gly Asn Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Lys Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300

Ser Trp Asn Gln Thr Asn
305                 310


<210> SEQ ID NO 20
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 20

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Arg Glu His Pro Glu Lys Gln
                85                  90                  95

Lys Ile Asn Phe Asn Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160
```

Asn His Gly Pro Thr Pro Val Lys Glu Gly Ser Lys Asp Pro Arg Gly
165 170 175

Gly Ile Phe Asp Ala Val Phe Thr Arg Gly Asn Gln Ser Lys Leu Leu
180 185 190

Thr Ser Arg His Asp Phe Lys Glu Lys Asn Leu Lys Glu Ile Ser Asp
195 200 205

Leu Ile Lys Lys Glu Leu Asp Glu Gly Lys Ala Leu Gly Leu Ser His
210 215 220

Thr Tyr Ala Asn Val Arg Ile Asn His Val Ile Asn Leu Trp Gly Ala
225 230 235 240

Asp Phe Asp Ser Asn Gly Asn Leu Lys Ala Ile Tyr Val Thr Asp Ser
245 250 255

Asp Ser Asn Ala Ser Ile Gly Met Lys Lys Tyr Phe Val Gly Val Asn
260 265 270

Ser Ala Gly Lys Val Ala Ile Ser Ala Lys Glu Ile Lys Glu Asp Asn
275 280 285

Ile Gly Ala Gln Val Leu Gly Leu Phe Thr Leu Ser Thr Gly Gln Asp
290 295 300

Ser Trp Asn Gln Thr Asn
305 310

<210> SEQ ID NO 21
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 21

Asp Ser Phe Ser Ala Asn Gln Glu Ile Arg Tyr Ser Glu Val Thr Pro
1 5 10 15

Tyr His Val Thr Ser Val Trp Thr Lys Gly Val Thr Pro Pro Ala Asn
20 25 30

Phe Thr Gln Gly Glu Asp Val Phe His Ala Pro Tyr Val Ala Asn Gln
35 40 45

Gly Trp Tyr Asp Ile Thr Lys Thr Phe Asn Gly Lys Asp Asp Leu Leu
50 55 60

Cys Gly Ala Ala Thr Ala Gly Asn Met Leu His Trp Trp Phe Asp Gln
65 70 75 80

Asn Lys Asp Gln Ile Lys Arg Tyr Leu Lys Glu His Pro Glu Lys Gln
85 90 95

Lys Ile Asn Phe Asn Gly Glu Gln Met Phe Asp Val Lys Glu Ala Ile
100 105 110

Arg Thr Lys Asn His Gln Leu Asp Ser Lys Leu Phe Glu Tyr Phe Lys
115 120 125

Glu Lys Ala Phe Pro Tyr Leu Ser Thr Lys His Leu Gly Val Phe Pro
130 135 140

Asp His Val Ile Asp Met Phe Ile Asn Gly Tyr Arg Leu Ser Leu Thr
145 150 155 160

Asn His Gly Pro Thr Pro Val Lys Glu Gly Ser Lys Asp Pro Arg Gly
165 170 175

Gly Ile Phe Asp Ala Val Phe Thr Arg Gly Asn Gln Ser Lys Leu Leu
180 185 190

Thr Ser Arg His Asp Phe Lys Glu Lys Asn Leu Lys Glu Ile Ser Asp
195 200 205

Leu Ile Lys Lys Glu Leu Glu Glu Gly Lys Ala Leu Gly Leu Ser His
210 215 220

Thr Tyr Ala Asn Val Arg Ile Asn His Val Ile Asn Leu Trp Gly Ala
225 230 235 240

Asp Phe Asp Ser Asn Gly Asn Leu Lys Ala Ile Tyr Val Thr Asp Ser
245 250 255

Asp Ser Asn Ala Ser Ile Gly Met Lys Lys Tyr Phe Val Gly Val Asn
260 265 270

Lys Ala Gly Lys Val Ala Ile Ser Ala Lys Glu Ile Lys Glu Asp Asn
275 280 285

Ile Gly Ala Gln Val Leu Gly Leu Phe Thr Leu Ser Thr Gly Gln Asp
290 295 300

Ser Trp Asn Gln Thr Asn
305 310

<210> SEQ ID NO 22
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 22

Asp Ser Phe Ser Ala Asn Gln Glu Ile Arg Tyr Ser Glu Val Thr Pro
1 5 10 15

Tyr His Val Thr Ser Val Trp Thr Lys Gly Val Thr Pro Pro Ala Asn
20 25 30

Phe Thr Gln Gly Glu Asp Val Phe His Ala Pro Tyr Val Ala Asn Gln
35 40 45

Gly Trp Tyr Asp Ile Thr Lys Thr Phe Asn Gly Lys Asp Asp Leu Leu
50 55 60

Cys Gly Ala Ala Thr Ala Gly Asn Met Leu His Trp Trp Phe Asp Gln
65 70 75 80

Asn Lys Asp Gln Ile Glu Arg Tyr Leu Glu Glu His Pro Glu Lys Gln
85 90 95

Lys Ile Asn Phe Asn Gly Glu Gln Met Phe Asp Val Lys Glu Ala Ile
100 105 110

Asp Thr Lys Asn His Gln Leu Asp Ser Lys Leu Phe Glu Tyr Phe Lys
115 120 125

Glu Lys Ala Phe Pro Tyr Leu Ser Thr Lys His Leu Gly Val Phe Pro
130 135 140

Asp His Val Ile Asp Met Phe Ile Asn Gly Tyr Arg Leu Ser Leu Thr
145 150 155 160

Asn His Gly Pro Thr Pro Val Lys Glu Gly Ser Lys Asp Pro Arg Gly
165 170 175

Gly Ile Phe Asp Ala Val Phe Thr Arg Gly Asn Gln Ser Lys Leu Leu
180 185 190

Thr Ser Arg His Asp Phe Lys Glu Lys Asn Leu Lys Glu Ile Ser Asp
195 200 205

Leu Ile Lys Glu Glu Leu Thr Lys Gly Lys Ala Leu Gly Leu Ser His
210 215 220

Thr Tyr Ala Asn Val Arg Ile Asn His Val Ile Asn Leu Trp Gly Ala
225 230 235 240

Asp Phe Asp Ser Asn Gly Asn Leu Lys Ala Ile Tyr Val Thr Asp Ser
245 250 255

```
Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Lys Asn
        275                 280                 285

Ile Gly Ala Gln Val Leu Gly Leu Phe Thr Leu Ser Thr Gly Gln Lys
    290                 295                 300

Ser Trp Asn Gln Thr Asn
305                 310
```

<210> SEQ ID NO 23
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 23

```
Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Lys Glu His Pro Glu Lys Gln
                85                  90                  95

Lys Ile Asn Phe Arg Gly Glu Gln Met Phe Asp Val Lys Glu Ala Ile
            100                 105                 110

Arg Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asn Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Ser Glu Leu Glu Asn Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Lys Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300
```

Ser Trp Asn Gln Thr Asn
305 310

<210> SEQ ID NO 24
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 24

Asp Ser Phe Ser Ala Asn Gln Glu Ile Arg Tyr Ser Glu Val Thr Pro
1 5 10 15

Tyr His Val Thr Ser Val Trp Thr Lys Gly Val Thr Pro Pro Ala Asn
20 25 30

Phe Thr Gln Gly Glu Asp Val Phe His Ala Pro Tyr Val Ala Asn Gln
35 40 45

Gly Trp Tyr Asp Ile Thr Lys Thr Phe Asn Gly Lys Asp Asp Leu Leu
50 55 60

Cys Gly Ala Ala Thr Ala Gly Asn Met Leu His Trp Trp Phe Asp Gln
65 70 75 80

Asn Lys Asp Gln Ile Lys Arg Tyr Leu Lys Glu His Pro Glu Lys Gln
85 90 95

Lys Ile Asn Phe Arg Gly Glu Gln Met Phe Asp Val Lys Glu Ala Ile
100 105 110

Arg Thr Lys Asn His Gln Leu Asp Ser Lys Leu Phe Glu Tyr Phe Lys
115 120 125

Glu Lys Ala Phe Pro Tyr Leu Ser Thr Lys His Leu Gly Val Phe Pro
130 135 140

Asp His Val Ile Asp Met Phe Ile Asn Gly Tyr Arg Leu Ser Leu Thr
145 150 155 160

Asn His Gly Pro Thr Pro Val Lys Lys Gly Ser Lys Asp Pro Arg Gly
165 170 175

Gly Ile Phe Asp Ala Val Phe Thr Arg Gly Asn Gln Ser Lys Leu Leu
180 185 190

Thr Ser Arg His Asp Phe Lys Glu Lys Asn Leu Lys Glu Ile Ser Asp
195 200 205

Leu Ile Lys Lys Glu Leu Glu Glu Gly Lys Ala Leu Gly Leu Ser His
210 215 220

Thr Tyr Ala Asn Val Arg Ile Asn His Val Ile Asn Leu Trp Gly Ala
225 230 235 240

Asp Phe Asp Ser Asn Gly Asn Leu Lys Ala Ile Tyr Val Thr Asp Ser
245 250 255

Asp Ser Asn Ala Ser Ile Gly Met Lys Lys Tyr Phe Val Gly Val Asn
260 265 270

Ser Ala Gly Lys Val Ala Ile Ser Ala Lys Glu Ile Lys Glu Asp Asn
275 280 285

Ile Gly Ala Gln Val Leu Gly Leu Phe Thr Leu Ser Thr Gly Gln Asp
290 295 300

Ser Trp Asn Gln Thr Asn
305 310

<210> SEQ ID NO 25
<211> LENGTH: 310
<212> TYPE: PRT
<213> ORGANISM: Artificial Sequence
<220> FEATURE:

<223> OTHER INFORMATION: IgG degrading enzyme amino acid sequence

<400> SEQUENCE: 25

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Glu Arg Tyr Leu Glu Glu His Pro Glu Lys Gln
                85                  90                  95

Lys Ile Asn Phe Arg Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Lys Gly Ser Lys Asp Pro Arg Gly
                165                 170                 175

Gly Ile Phe Asp Ala Val Phe Thr Arg Gly Asn Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Glu Glu Leu Thr Lys Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Lys
    290                 295                 300

Ser Trp Asn Gln Thr Asn
305                 310

<210> SEQ ID NO 26
<211> LENGTH: 306
<212> TYPE: PRT
<213> ORGANISM: Artificial Sequence
<220> FEATURE:
<223> OTHER INFORMATION: IgG degrading enzyme amino acid sequence

<400> SEQUENCE: 26

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Pro Ala Asn
            20                  25                  30

```
Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Asn Gly Glu Gln Met Phe Asp Val Lys Glu Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asp Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Lys Glu Leu Thr Glu Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Asp
    290                 295                 300

Ser Trp
305


<210> SEQ ID NO 27
<211> LENGTH: 290
<212> TYPE: PRT
<213> ORGANISM: Artificial Sequence
<220> FEATURE:
<223> OTHER INFORMATION: IgG degrading enzyme amino acid sequence

<400> SEQUENCE: 27

Ser Val Trp Thr Lys Gly Val Thr Pro Pro Ala Asn Phe Thr Gln Gly
1               5                   10                  15

Glu Asp Val Phe His Ala Pro Tyr Val Ala Asn Gln Gly Trp Tyr Asp
            20                  25                  30

Ile Thr Lys Thr Phe Asn Gly Lys Asp Asp Leu Leu Cys Gly Ala Ala
        35                  40                  45

Thr Ala Gly Asn Met Leu His Trp Trp Phe Asp Gln Asn Lys Asp Gln
    50                  55                  60

Ile Lys Arg Tyr Leu Glu Glu His Pro Glu Lys Gln Lys Ile Asn Phe
65                  70                  75                  80
```

```
Asn Gly Glu Gln Met Phe Asp Val Lys Glu Ala Ile Asp Thr Lys Asn
                85                  90                  95

His Gln Leu Asp Ser Lys Leu Phe Glu Tyr Phe Lys Glu Lys Ala Phe
            100                 105                 110

Pro Tyr Leu Ser Thr Lys His Leu Gly Val Phe Pro Asp His Val Ile
        115                 120                 125

Asp Met Phe Ile Asn Gly Tyr Arg Leu Ser Leu Thr Asn His Gly Pro
    130                 135                 140

Thr Pro Val Lys Glu Gly Ser Lys Asp Pro Arg Gly Gly Ile Phe Asp
145                 150                 155                 160

Ala Val Phe Thr Arg Gly Asp Gln Ser Lys Leu Leu Thr Ser Arg His
                165                 170                 175

Asp Phe Lys Glu Lys Asn Leu Lys Glu Ile Ser Asp Leu Ile Lys Lys
            180                 185                 190

Glu Leu Thr Glu Gly Lys Ala Leu Gly Leu Ser His Thr Tyr Ala Asn
        195                 200                 205

Val Arg Ile Asn His Val Ile Asn Leu Trp Gly Ala Asp Phe Asp Ser
    210                 215                 220

Asn Gly Asn Leu Lys Ala Ile Tyr Val Thr Asp Ser Asp Ser Asn Ala
225                 230                 235                 240

Ser Ile Gly Met Lys Lys Tyr Phe Val Gly Val Asn Ser Ala Gly Lys
                245                 250                 255

Val Ala Ile Ser Ala Lys Glu Ile Lys Glu Asp Asn Ile Gly Ala Gln
            260                 265                 270

Val Leu Gly Leu Phe Thr Leu Ser Thr Gly Gln Asp Ser Trp Asn Gln
        275                 280                 285

Thr Asn
    290


<210> SEQ ID NO 28
<211> LENGTH: 290
<212> TYPE: PRT
<213> ORGANISM: Artificial Sequence
<220> FEATURE:
<223> OTHER INFORMATION: IgG degrading enzyme amino acid sequence

<400> SEQUENCE: 28

Ser Val Trp Thr Lys Gly Val Thr Pro Pro Ala Asn Phe Thr Gln Gly
1               5                   10                  15

Glu Asp Val Phe His Ala Pro Tyr Val Ala Asn Gln Gly Trp Tyr Asp
            20                  25                  30

Ile Thr Lys Thr Phe Asn Gly Lys Asp Asp Leu Leu Cys Gly Ala Ala
        35                  40                  45

Thr Ala Gly Asn Met Leu His Trp Trp Phe Asp Gln Asn Lys Asp Gln
    50                  55                  60

Ile Lys Arg Tyr Leu Glu Glu His Pro Glu Lys Gln Lys Ile Asn Phe
65                  70                  75                  80

Lys Gly Glu Gln Met Phe Asp Val Lys Glu Ala Ile Asp Thr Lys Asn
                85                  90                  95

His Gln Leu Asp Ser Lys Leu Phe Glu Tyr Phe Lys Glu Lys Ala Phe
            100                 105                 110

Pro Tyr Leu Ser Thr Lys His Leu Gly Val Phe Pro Asp His Val Ile
        115                 120                 125

Asp Met Phe Ile Asn Gly Tyr Arg Leu Ser Leu Thr Asn His Gly Pro
    130                 135                 140
```

```
Thr Pro Val Lys Glu Gly Ser Lys Asp Pro Arg Gly Gly Ile Phe Asp
145                 150                 155                 160

Ala Val Phe Thr Arg Gly Asn Gln Ser Lys Leu Leu Thr Ser Arg His
                165                 170                 175

Asp Phe Lys Glu Lys Asn Leu Lys Glu Ile Ser Asp Leu Ile Lys Lys
            180                 185                 190

Glu Leu Thr Glu Gly Lys Ala Leu Gly Leu Ser His Thr Tyr Ala Asn
        195                 200                 205

Val Arg Ile Asn His Val Ile Asn Leu Trp Gly Ala Asp Phe Asp Ser
    210                 215                 220

Asn Gly Asn Leu Lys Ala Ile Tyr Val Thr Asp Ser Asp Ser Asn Ala
225                 230                 235                 240

Ser Ile Gly Met Lys Lys Tyr Phe Val Gly Val Asn Ser Ala Gly Lys
                245                 250                 255

Val Ala Ile Ser Ala Lys Glu Ile Lys Glu Asp Asn Ile Gly Ala Gln
            260                 265                 270

Val Leu Gly Leu Phe Thr Leu Ser Thr Gly Gln Asp Ser Trp Asn Gln
        275                 280                 285

Thr Asn
    290


<210> SEQ ID NO 29
<211> LENGTH: 290
<212> TYPE: PRT
<213> ORGANISM: Artificial Sequence
<220> FEATURE:
<223> OTHER INFORMATION: IgG degrading enzyme amino acid sequence

<400> SEQUENCE: 29

Ser Val Trp Thr Lys Gly Val Thr Pro Pro Ala Asn Phe Thr Gln Gly
1               5                   10                  15

Glu Asp Val Phe His Ala Pro Tyr Val Ala Asn Gln Gly Trp Tyr Asp
            20                  25                  30

Ile Thr Lys Thr Phe Asn Gly Lys Asp Asp Leu Leu Cys Gly Ala Ala
        35                  40                  45

Thr Ala Gly Asn Met Leu His Trp Trp Phe Asp Gln Asn Lys Asp Gln
    50                  55                  60

Ile Glu Arg Tyr Leu Glu Glu His Pro Glu Lys Gln Lys Ile Asn Phe
65                  70                  75                  80

Lys Gly Glu Gln Met Phe Asp Val Lys Lys Ala Ile Asp Thr Lys Asn
                85                  90                  95

His Gln Leu Asp Ser Lys Leu Phe Glu Tyr Phe Lys Glu Lys Ala Phe
            100                 105                 110

Pro Tyr Leu Ser Thr Lys His Leu Gly Val Phe Pro Asp His Val Ile
        115                 120                 125

Asp Met Phe Ile Asn Gly Tyr Arg Leu Ser Leu Thr Asn His Gly Pro
    130                 135                 140

Thr Pro Val Lys Glu Gly Ser Lys Asp Pro Arg Gly Gly Ile Phe Asp
145                 150                 155                 160

Ala Val Phe Thr Arg Gly Asn Gln Ser Lys Leu Leu Thr Ser Arg His
                165                 170                 175

Asp Phe Lys Glu Lys Asn Leu Lys Glu Ile Ser Asp Leu Ile Lys Glu
            180                 185                 190

Glu Leu Thr Lys Gly Lys Ala Leu Gly Leu Ser His Thr Tyr Ala Asn
        195                 200                 205
```

```
Val Arg Ile Asn His Val Ile Asn Leu Trp Gly Ala Asp Phe Asp Ser
    210                 215                 220

Asn Gly Asn Leu Lys Ala Ile Tyr Val Thr Asp Ser Asp Ser Asn Ala
225                 230                 235                 240

Ser Ile Gly Met Lys Lys Tyr Phe Val Gly Val Asn Ser Ala Gly Lys
                245                 250                 255

Val Ala Ile Ser Ala Lys Glu Ile Lys Glu Asp Asn Ile Gly Ala Gln
            260                 265                 270

Val Leu Gly Leu Phe Thr Leu Ser Thr Gly Gln Lys Ser Trp Asn Gln
        275                 280                 285

Thr Asn
    290


<210> SEQ ID NO 30
<211> LENGTH: 319
<212> TYPE: PRT
<213> ORGANISM: Artificial Sequence
<220> FEATURE:
<223> OTHER INFORMATION: IgG degrading enzyme amino acid sequence

<400> SEQUENCE: 30

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Ala Asn
            20                  25                  30

Phe Thr Gln Gly Glu Asp Val Phe His Ala Pro Tyr Val Ala Asn Gln
        35                  40                  45

Gly Trp Tyr Asp Ile Thr Lys Thr Phe Asn Gly Lys Asp Asp Leu Leu
    50                  55                  60

Cys Gly Ala Ala Thr Ala Gly Asn Met Leu His Trp Trp Phe Asp Gln
65                  70                  75                  80

Asn Lys Asp Gln Ile Glu Arg Tyr Leu Glu Glu His Pro Glu Lys Gln
                85                  90                  95

Lys Ile Asn Phe Lys Gly Glu Gln Met Phe Asp Val Lys Lys Ala Ile
            100                 105                 110

Asp Thr Lys Asn His Gln Leu Asp Ser Lys Leu Phe Glu Tyr Phe Lys
        115                 120                 125

Glu Lys Ala Phe Pro Tyr Leu Ser Thr Lys His Leu Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asn Gln Ser Lys Leu Leu
            180                 185                 190

Thr Ser Arg His Asp Phe Lys Glu Lys Asn Leu Lys Glu Ile Ser Asp
        195                 200                 205

Leu Ile Lys Glu Glu Leu Thr Lys Gly Lys Ala Leu Gly Leu Ser His
    210                 215                 220

Thr Tyr Ala Asn Val Arg Ile Asn His Val Ile Asn Leu Trp Gly Ala
225                 230                 235                 240

Asp Phe Asp Ser Asn Gly Asn Leu Lys Ala Ile Tyr Val Thr Asp Ser
                245                 250                 255

Asp Ser Asn Ala Ser Ile Gly Met Lys Lys Tyr Phe Val Gly Val Asn
            260                 265                 270
```

Ser Ala Gly Lys Val Ala Ile Ser Ala Lys Glu Ile Lys Glu Asp Asn
        275                 280                 285

Ile Gly Ala Gln Val Leu Gly Leu Phe Thr Leu Ser Thr Gly Gln Lys
    290                 295                 300

Ser Trp Asn Gln Thr Asn Gly Gly Gly His His His His His His
305                 310                 315

<210> SEQ ID NO 31
<211> LENGTH: 315
<212> TYPE: PRT
<213> ORGANISM: Artificial Sequence
<220> FEATURE:
<223> OTHER INFORMATION: IgG degrading enzyme amino acid sequence

<400> SEQUENCE: 31

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Arg Tyr Asn Asn Glu Asp Val Ile His Ala Pro Tyr Leu
        35                  40                  45

Ala His Gln Gly Trp Tyr Asp Ile Thr Lys Ala Phe Asp Gly Lys Asp
    50                  55                  60

Asn Leu Leu Cys Gly Ala Ala Thr Ala Gly Asn Met Leu His Trp Trp
65                  70                  75                  80

Phe Asp Gln Asn Lys Thr Glu Ile Glu Ala Tyr Leu Ser Lys His Pro
                85                  90                  95

Glu Lys Gln Lys Ile Ile Phe Asn Asn Gln Glu Leu Phe Asp Leu Lys
            100                 105                 110

Ala Ala Ile Asp Thr Lys Asp Ser Gln Thr Asn Ser Gln Leu Phe Asn
        115                 120                 125

Tyr Phe Arg Asp Lys Ala Phe Pro Asn Leu Ser Ala Arg Gln Leu Gly
    130                 135                 140

Val Met Pro Asp Leu Val Leu Asp Met Phe Ile Asn Gly Tyr Tyr Leu
145                 150                 155                 160

Asn Val Phe Lys Thr Gln Ser Thr Asp Val Asn Arg Pro Tyr Gln Asp
                165                 170                 175

Lys Asp Lys Arg Gly Gly Ile Phe Asp Ala Val Phe Thr Arg Gly Asp
            180                 185                 190

Gln Thr Thr Leu Leu Thr Ala Arg His Asp Leu Lys Asn Lys Gly Leu
        195                 200                 205

Asn Asp Ile Ser Thr Ile Ile Lys Gln Glu Leu Thr Glu Gly Arg Ala
    210                 215                 220

Leu Ala Leu Ser His Thr Tyr Ala Asn Val Ser Ile Ser His Val Ile
225                 230                 235                 240

Asn Leu Trp Gly Ala Asp Phe Asn Ala Glu Gly Asn Leu Glu Ala Ile
                245                 250                 255

Tyr Val Thr Asp Ser Asp Ala Asn Ala Ser Ile Gly Met Lys Lys Tyr
            260                 265                 270

Phe Val Gly Ile Asn Ala His Gly His Val Ala Ile Ser Ala Lys Lys
        275                 280                 285

Ile Glu Gly Glu Asn Ile Gly Ala Gln Val Leu Gly Leu Phe Thr Leu
    290                 295                 300

Ser Ser Gly Lys Asp Ile Trp Gln Lys Leu Ser
305                 310                 315

<210> SEQ ID NO 32
<211> LENGTH: 313
<212> TYPE: PRT
<213> ORGANISM: Artificial Sequence
<220> FEATURE:
<223> OTHER INFORMATION: IgG degrading enzyme amino acid sequence

<400> SEQUENCE: 32

```
Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Arg Tyr Asn Asn Glu Asp Val Phe His Ala Pro Tyr Val
        35                  40                  45

Ala Asn Gln Gly Trp Tyr Asp Ile Thr Lys Ala Phe Asp Gly Lys Asp
    50                  55                  60

Asn Leu Leu Cys Gly Ala Ala Thr Ala Gly Asn Met Leu His Trp Trp
65                  70                  75                  80

Phe Asp Gln Asn Lys Asp Gln Ile Lys Arg Tyr Leu Glu Glu His Pro
                85                  90                  95

Glu Lys Gln Lys Ile Asn Phe Asn Gly Asp Asn Met Phe Asp Val Lys
            100                 105                 110

Lys Ala Ile Asp Thr Lys Asn His Gln Leu Asp Ser Lys Leu Phe Asn
        115                 120                 125

Tyr Phe Lys Glu Lys Ala Phe Pro Gly Leu Ser Ala Arg Arg Ile Gly
    130                 135                 140

Val Phe Pro Asp His Val Ile Asp Met Phe Ile Asn Gly Tyr Arg Leu
145                 150                 155                 160

Ser Leu Thr Asn His Gly Pro Thr Pro Val Lys Glu Gly Ser Lys Asp
                165                 170                 175

Pro Arg Gly Gly Ile Phe Asp Ala Val Phe Thr Arg Gly Asn Gln Ser
            180                 185                 190

Lys Leu Leu Thr Ser Arg His Asp Phe Lys Asn Lys Asn Leu Asn Asp
        195                 200                 205

Ile Ser Thr Ile Ile Lys Gln Glu Leu Thr Lys Gly Lys Ala Leu Gly
    210                 215                 220

Leu Ser His Thr Tyr Ala Asn Val Ser Ile Asn His Val Ile Asn Leu
225                 230                 235                 240

Trp Gly Ala Asp Phe Asn Ala Glu Gly Asn Leu Glu Ala Ile Tyr Val
                245                 250                 255

Thr Asp Ser Asp Ser Asn Ala Ser Ile Gly Met Lys Lys Tyr Phe Val
            260                 265                 270

Gly Val Asn Ala His Gly His Val Ala Ile Ser Ala Lys Lys Ile Glu
        275                 280                 285

Gly Glu Asn Ile Gly Ala Gln Val Leu Gly Leu Phe Thr Leu Ser Thr
    290                 295                 300

Gly Gln Asp Ser Trp Gln Lys Leu Ser
305                 310
```

<210> SEQ ID NO 33
<211> LENGTH: 313
<212> TYPE: PRT
<213> ORGANISM: Artificial Sequence
<220> FEATURE:
<223> OTHER INFORMATION: IgG degrading enzyme amino acid sequence

<400> SEQUENCE: 33

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Arg Tyr Asn Asn Glu Asp Val Ile His Ala Pro Tyr Leu
        35                  40                  45

Ala Asn Gln Gly Trp Tyr Asp Ile Thr Lys Ala Phe Asp Gly Lys Asp
    50                  55                  60

Asn Leu Leu Cys Gly Ala Ala Thr Ala Gly Asn Met Leu His Trp Trp
65                  70                  75                  80

Phe Asp Gln Asn Lys Thr Glu Ile Glu Ala Tyr Leu Ser Lys His Pro
                85                  90                  95

Glu Lys Gln Lys Ile Ile Phe Arg Asn Gln Glu Leu Phe Asp Leu Lys
            100                 105                 110

Glu Ala Ile Arg Thr Lys Asp Ser Gln Thr Gln Leu Phe Glu Tyr Phe
        115                 120                 125

Arg Asp Lys Ala Phe Pro Tyr Leu Ser Ala Arg Gln Leu Gly Val Met
    130                 135                 140

Pro Asp Leu Val Leu Asp Met Phe Ile Asn Gly Tyr Tyr Leu Asn Val
145                 150                 155                 160

Phe Lys Thr Gln Ser Thr Asp Val Lys Arg Pro Tyr Gln Asp Lys Asp
                165                 170                 175

Lys Arg Gly Gly Ile Phe Asp Ala Val Phe Thr Arg Gly Asn Gln Thr
            180                 185                 190

Thr Leu Leu Thr Ala Arg His Asp Leu Lys Asn Lys Gly Leu Asn Asp
        195                 200                 205

Ile Ser Thr Ile Ile Lys Glu Glu Leu Thr Lys Gly Arg Ala Leu Ala
    210                 215                 220

Leu Ser His Thr Tyr Ala Asn Val Ser Ile Ser His Val Ile Asn Leu
225                 230                 235                 240

Trp Gly Ala Asp Phe Asn Ala Glu Gly Asn Leu Glu Ala Thr Tyr Val
                245                 250                 255

Thr Asp Ser Asp Ala Asn Ala Ser Ile Gly Met Lys Lys Tyr Phe Val
            260                 265                 270

Gly Ile Asn Lys His Gly His Val Ala Ile Ser Ala Lys Lys Ile Glu
        275                 280                 285

Gly Glu Asn Ile Gly Ala Gln Val Leu Gly Leu Phe Thr Leu Ser Ser
    290                 295                 300

Gly Lys Asp Ile Trp Gln Lys Leu Asn
305                 310

<210> SEQ ID NO 34
<211> LENGTH: 315
<212> TYPE: PRT
<213> ORGANISM: Artificial Sequence
<220> FEATURE:
<223> OTHER INFORMATION: IgG degrading enzyme amino acid sequence

<400> SEQUENCE: 34

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Arg Tyr Asn Asn Glu Asp Val Ile His Ala Pro Tyr Leu

```
        35                  40                  45

Ala His Gln Gly Trp Tyr Asp Ile Thr Lys Thr Phe Asn Gly Lys Asp
    50                  55                  60

Asn Leu Leu Cys Gly Ala Ala Thr Ala Gly Asn Met Leu His Trp Trp
65                  70                  75                  80

Phe Asp Gln Asn Lys Thr Glu Ile Glu Ala Tyr Leu Ser Lys His Pro
                85                  90                  95

Glu Lys Gln Lys Ile Ile Phe Asn Asn Glu Glu Leu Phe Asp Leu Lys
            100                 105                 110

Ala Ala Ile Asp Thr Lys Asp Ser Gln Thr Asn Ser Gln Leu Phe Asn
        115                 120                 125

Tyr Phe Lys Glu Lys Ala Phe Pro Asn Leu Ser Thr Arg Gln Leu Gly
    130                 135                 140

Val Met Pro Asp Leu Val Leu Asp Met Phe Ile Asn Gly Tyr Tyr Leu
145                 150                 155                 160

Asn Val Phe Lys Thr Gln Ser Thr Asp Val Asn Arg Pro Tyr Gln Asp
                165                 170                 175

Lys Asp Lys Arg Gly Gly Ile Phe Asp Ala Val Phe Thr Arg Gly Asn
            180                 185                 190

Gln Thr Thr Leu Leu Thr Ala Arg His Asp Phe Lys Glu Lys Gly Leu
        195                 200                 205

Lys Asp Ile Ser Thr Ile Ile Lys Gln Glu Leu Thr Glu Gly Arg Ala
    210                 215                 220

Leu Ala Leu Ser His Thr Tyr Ala Asn Val Ser Ile Ser His Val Ile
225                 230                 235                 240

Asn Leu Trp Gly Ala Asp Phe Asp Ala Glu Gly Asn Leu Lys Ala Ile
                245                 250                 255

Tyr Val Thr Asp Ser Asp Ala Asn Ala Ser Ile Gly Met Lys Lys Tyr
            260                 265                 270

Phe Val Gly Ile Asn Ala His Gly Lys Val Ala Ile Ser Ala Lys Lys
        275                 280                 285

Ile Glu Gly Glu Asn Ile Gly Ala Gln Val Leu Gly Leu Phe Thr Leu
    290                 295                 300

Ser Ser Gly Lys Asp Ile Trp Gln Gln Leu Ser
305                 310                 315


<210> SEQ ID NO 35
<211> LENGTH: 315
<212> TYPE: PRT
<213> ORGANISM: Artificial Sequence
<220> FEATURE:
<223> OTHER INFORMATION: IgG degrading enzyme amino acid sequence

<400> SEQUENCE: 35

Asp Ser Phe Ser Ala Asn Gln Glu Ile Arg Tyr Ser Glu Val Thr Pro
1               5                   10                  15

Tyr His Val Thr Ser Val Trp Thr Lys Gly Val Thr Pro Leu Thr Pro
            20                  25                  30

Glu Gln Phe Arg Tyr Asn Asn Glu Asp Val Ile His Ala Pro Tyr Leu
        35                  40                  45

Ala His Gln Gly Trp Tyr Asp Ile Thr Lys Ala Phe Asp Gly Lys Asp
    50                  55                  60

Asn Leu Leu Cys Gly Ala Ala Thr Ala Gly Asn Met Leu His Trp Trp
65                  70                  75                  80

Phe Asp Gln Asn Lys Thr Glu Ile Glu Ala Tyr Leu Ser Lys His Pro
```

```
                85                  90                  95

Glu Lys Gln Lys Ile Ile Phe Asn Asn Gln Glu Leu Phe Asp Leu Lys
            100                 105                 110

Ala Ala Ile Asp Thr Lys Asp Ser Gln Thr Asn Ser Gln Leu Phe Asn
        115                 120                 125

Tyr Phe Arg Asp Lys Ala Phe Pro Asn Leu Ser Ala Arg Gln Leu Gly
    130                 135                 140

Val Met Pro Asp Leu Val Leu Asp Met Phe Ile Asn Gly Tyr Tyr Leu
145                 150                 155                 160

Asn Val Phe Lys Thr Gln Ser Thr Asp Val Asn Arg Pro Tyr Gln Asp
                165                 170                 175

Lys Asp Lys Arg Gly Gly Ile Phe Asp Ala Val Phe Thr Arg Gly Asp
            180                 185                 190

Gln Thr Thr Leu Leu Thr Ala Arg His Asp Leu Lys Asn Lys Gly Leu
        195                 200                 205

Asn Asp Ile Ser Thr Ile Ile Lys Gln Glu Leu Thr Glu Gly Arg Ala
    210                 215                 220

Leu Ala Leu Ser His Thr Tyr Ala Asn Val Ser Ile Ser His Val Ile
225                 230                 235                 240

Asn Leu Trp Gly Ala Asp Phe Asn Ala Glu Gly Asn Leu Glu Ala Ile
                245                 250                 255

Tyr Val Thr Asp Ser Asp Ala Asn Ala Ser Ile Gly Met Lys Lys Tyr
            260                 265                 270

Phe Val Gly Ile Asn Ala His Gly His Val Ala Ile Ser Ala Lys Lys
        275                 280                 285

Ile Glu Gly Glu Asn Ile Gly Ala Gln Val Leu Gly Leu Phe Thr Leu
    290                 295                 300

Ser Ser Gly Lys Asp Ile Trp Gln Lys Leu Ser
305                 310                 315


<210> SEQ ID NO 36
<211> LENGTH: 295
<212> TYPE: PRT
<213> ORGANISM: Artificial Sequence
<220> FEATURE:
<223> OTHER INFORMATION: IgG degrading enzyme amino acid sequence

<400> SEQUENCE: 36

Ser Val Trp Thr Lys Gly Val Thr Pro Leu Thr Pro Glu Gln Phe Arg
1               5                   10                  15

Tyr Asn Asn Glu Asp Val Ile His Ala Pro Tyr Leu Ala His Gln Gly
            20                  25                  30

Trp Tyr Asp Ile Thr Lys Ala Phe Asp Gly Lys Asp Asn Leu Leu Cys
        35                  40                  45

Gly Ala Ala Thr Ala Gly Asn Met Leu His Trp Trp Phe Asp Gln Asn
    50                  55                  60

Lys Thr Glu Ile Glu Ala Tyr Leu Ser Lys His Pro Glu Lys Gln Lys
65                  70                  75                  80

Ile Ile Phe Asn Asn Gln Glu Leu Phe Asp Leu Lys Ala Ala Ile Asp
                85                  90                  95

Thr Lys Asp Ser Gln Thr Asn Ser Gln Leu Phe Asn Tyr Phe Arg Asp
            100                 105                 110

Lys Ala Phe Pro Asn Leu Ser Ala Arg Gln Leu Gly Val Met Pro Asp
        115                 120                 125

Leu Val Leu Asp Met Phe Ile Asn Gly Tyr Tyr Leu Asn Val Phe Lys
```

```
    130                 135                 140

Thr Gln Ser Thr Asp Val Asn Arg Pro Tyr Gln Asp Lys Asp Lys Arg
145                 150                 155                 160

Gly Gly Ile Phe Asp Ala Val Phe Thr Arg Gly Asp Gln Thr Thr Leu
                165                 170                 175

Leu Thr Ala Arg His Asp Leu Lys Asn Lys Gly Leu Asn Asp Ile Ser
            180                 185                 190

Thr Ile Ile Lys Gln Glu Leu Thr Glu Gly Arg Ala Leu Ala Leu Ser
        195                 200                 205

His Thr Tyr Ala Asn Val Ser Ile Ser His Val Ile Asn Leu Trp Gly
    210                 215                 220

Ala Asp Phe Asn Ala Glu Gly Asn Leu Glu Ala Ile Tyr Val Thr Asp
225                 230                 235                 240

Ser Asp Ala Asn Ala Ser Ile Gly Met Lys Lys Tyr Phe Val Gly Ile
                245                 250                 255

Asn Ala His Gly His Val Ala Ile Ser Ala Lys Lys Ile Glu Gly Glu
            260                 265                 270

Asn Ile Gly Ala Gln Val Leu Gly Leu Phe Thr Leu Ser Ser Gly Lys
        275                 280                 285

Asp Ile Trp Gln Lys Leu Ser
    290                 295


<210> SEQ ID NO 37
<211> LENGTH: 314
<212> TYPE: PRT
<213> ORGANISM: Artificial Sequence
<220> FEATURE:
<223> OTHER INFORMATION: IgG degrading enzyme amino acid sequence

<400> SEQUENCE: 37

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Thr Gln Gly Glu Asp Val Ile His Ala Pro Tyr Leu Ala
        35                  40                  45

His Gln Gly Trp Tyr Asp Ile Thr Lys Ala Phe Asp Gly Lys Asp Asn
    50                  55                  60

Leu Leu Cys Gly Ala Ala Thr Ala Gly Asn Met Leu His Trp Trp Phe
65                  70                  75                  80

Asp Gln Asn Lys Thr Glu Ile Glu Ala Tyr Leu Ser Lys His Pro Glu
                85                  90                  95

Lys Gln Lys Ile Ile Phe Asn Asn Gln Glu Leu Phe Asp Leu Lys Ala
            100                 105                 110

Ala Ile Asp Thr Lys Asp Ser Gln Thr Asn Ser Gln Leu Phe Asn Tyr
        115                 120                 125

Phe Arg Asp Lys Ala Phe Pro Asn Leu Ser Ala Arg Gln Leu Gly Val
    130                 135                 140

Met Pro Asp Leu Val Leu Asp Met Phe Ile Asn Gly Tyr Tyr Leu Asn
145                 150                 155                 160

Val Phe Lys Thr Gln Ser Thr Asp Val Asn Arg Pro Tyr Gln Asp Lys
                165                 170                 175

Asp Lys Arg Gly Gly Ile Phe Asp Ala Val Phe Thr Arg Gly Asp Gln
            180                 185                 190

Thr Thr Leu Leu Thr Ala Arg His Asp Leu Lys Asn Lys Gly Leu Asn
```

```
        195                 200                 205

Asp Ile Ser Thr Ile Ile Lys Gln Glu Leu Thr Glu Gly Arg Ala Leu
    210                 215                 220

Ala Leu Ser His Thr Tyr Ala Asn Val Ser Ile Ser His Val Ile Asn
225                 230                 235                 240

Leu Trp Gly Ala Asp Phe Asn Ala Glu Gly Asn Leu Glu Ala Ile Tyr
                245                 250                 255

Val Thr Asp Ser Asp Ala Asn Ala Ser Ile Gly Met Lys Lys Tyr Phe
            260                 265                 270

Val Gly Ile Asn Ala His Gly His Val Ala Ile Ser Ala Lys Lys Ile
        275                 280                 285

Glu Gly Glu Asn Ile Gly Ala Gln Val Leu Gly Leu Phe Thr Leu Ser
    290                 295                 300

Ser Gly Lys Asp Ile Trp Gln Lys Leu Ser
305                 310


<210> SEQ ID NO 38
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 38

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala His Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Phe Asn Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
        115                 120                 125

Asp Lys Ala Phe Pro Asn Leu Ser Ala Arg Gln Leu Gly Val Met Pro
    130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

Leu Leu Thr Ala Arg His Asp Leu Lys Asn Lys Gly Leu Asn Asp Ile
        195                 200                 205

Ser Thr Ile Ile Lys Gln Glu Leu Thr Glu Gly Arg Ala Leu Ala Leu
    210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
```

```
                245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
        275                 280                 285

Glu Asn Ile Gly Ala Gln Val Leu Gly Leu Phe Thr Leu Ser Ser Gly
    290                 295                 300

Lys Asp Ile Trp Gln Lys Leu Ser
305                 310


<210> SEQ ID NO 39
<211> LENGTH: 313
<212> TYPE: PRT
<213> ORGANISM: Artificial Sequence
<220> FEATURE:
<223> OTHER INFORMATION: IgG degrading enzyme amino acid sequence

<400> SEQUENCE: 39

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Arg Tyr Asn Asn Glu Asp Val Ile His Ala Pro Tyr Leu Ala His
        35                  40                  45

Gln Gly Trp Tyr Asp Ile Thr Lys Ala Phe Asp Gly Lys Asp Asn Leu
    50                  55                  60

Leu Cys Gly Ala Ala Thr Ala Gly Asn Met Leu His Trp Trp Phe Asp
65                  70                  75                  80

Gln Asn Lys Thr Glu Ile Glu Ala Tyr Leu Ser Lys His Pro Glu Lys
                85                  90                  95

Gln Lys Ile Ile Phe Asn Asn Gln Glu Leu Phe Asp Leu Lys Ala Ala
            100                 105                 110

Ile Asp Thr Lys Asp Ser Gln Thr Asn Ser Gln Leu Phe Asn Tyr Phe
        115                 120                 125

Arg Asp Lys Ala Phe Pro Asn Leu Ser Ala Arg Gln Leu Gly Val Met
    130                 135                 140

Pro Asp Leu Val Leu Asp Met Phe Ile Asn Gly Tyr Tyr Leu Asn Val
145                 150                 155                 160

Phe Lys Thr Gln Ser Thr Asp Val Asn Arg Pro Tyr Gln Asp Lys Asp
                165                 170                 175

Lys Arg Gly Gly Ile Phe Asp Ala Val Phe Thr Arg Gly Asp Gln Thr
            180                 185                 190

Thr Leu Leu Thr Ala Arg His Asp Leu Lys Asn Lys Gly Leu Asn Asp
        195                 200                 205

Ile Ser Thr Ile Ile Lys Gln Glu Leu Thr Glu Gly Arg Ala Leu Ala
    210                 215                 220

Leu Ser His Thr Tyr Ala Asn Val Ser Ile Ser His Val Ile Asn Leu
225                 230                 235                 240

Trp Gly Ala Asp Phe Asn Ala Glu Gly Asn Leu Glu Ala Ile Tyr Val
                245                 250                 255

Thr Asp Ser Asp Ala Asn Ala Ser Ile Gly Met Lys Lys Tyr Phe Val
            260                 265                 270

Gly Ile Asn Ala His Gly His Val Ala Ile Ser Ala Lys Lys Ile Glu
        275                 280                 285

Gly Glu Asn Ile Gly Ala Gln Val Leu Gly Leu Phe Thr Leu Ser Ser
```

```
    290                 295                 300

Gly Lys Asp Ile Trp Gln Lys Leu Ser
305                 310


<210> SEQ ID NO 40
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 40

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala His Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Ile Asn Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
        115                 120                 125

Asp Lys Ala Phe Pro Asn Leu Ser Ala Arg Gln Leu Gly Val Met Pro
    130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

Leu Leu Thr Ala Arg His Asp Leu Lys Asn Lys Gly Leu Asn Asp Ile
        195                 200                 205

Ser Thr Ile Ile Lys Gln Glu Leu Thr Glu Gly Arg Ala Leu Ala Leu
    210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
        275                 280                 285

Glu Asn Ile Gly Ala Gln Val Leu Gly Leu Phe Thr Leu Ser Ser Gly
    290                 295                 300

Lys Asp Ile Trp Gln Lys Leu Ser
305                 310


<210> SEQ ID NO 41
<211> LENGTH: 312
<212> TYPE: PRT
```

```
<213> ORGANISM: Artificial Sequence
<220> FEATURE:
<223> OTHER INFORMATION: IgG degrading enzyme amino acid sequence

<400> SEQUENCE: 41

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala His Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Phe Arg Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
        115                 120                 125

Asp Lys Ala Phe Pro Asn Leu Ser Ala Arg Gln Leu Gly Val Met Pro
    130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

Leu Leu Thr Ala Arg His Asp Leu Lys Asn Lys Gly Leu Asn Asp Ile
        195                 200                 205

Ser Thr Ile Ile Lys Gln Glu Leu Thr Glu Gly Arg Ala Leu Ala Leu
    210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
        275                 280                 285

Glu Asn Ile Gly Ala Gln Val Leu Gly Leu Phe Thr Leu Ser Ser Gly
    290                 295                 300

Lys Asp Ile Trp Gln Lys Leu Ser
305                 310


<210> SEQ ID NO 42
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 42

Asp Asp Tyr Gln Arg Asn Ala Thr Glu Ala Tyr Ala Lys Glu Val Pro
1               5                   10                  15
```

```
His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala His Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Ile Arg Asn Gln Glu Leu Phe Asp Leu Lys Ala Ala Ile
            100                 105                 110

Asp Thr Lys Asp Ser Gln Thr Asn Ser Gln Leu Phe Asn Tyr Phe Arg
        115                 120                 125

Asp Lys Ala Phe Pro Asn Leu Ser Ala Arg Gln Leu Gly Val Met Pro
    130                 135                 140

Asp Leu Val Leu Asp Met Phe Ile Asn Gly Tyr Tyr Leu Asn Val Phe
145                 150                 155                 160

Lys Thr Gln Ser Thr Asp Val Asn Arg Pro Tyr Gln Asp Lys Asp Lys
                165                 170                 175

Arg Gly Gly Ile Phe Asp Ala Val Phe Thr Arg Gly Asp Gln Thr Thr
            180                 185                 190

Leu Leu Thr Ala Arg His Asp Leu Lys Asn Lys Gly Leu Asn Asp Ile
        195                 200                 205

Ser Thr Ile Ile Lys Gln Glu Leu Thr Glu Gly Arg Ala Leu Ala Leu
    210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
            260                 265                 270

Ile Asn Ala His Gly His Val Ala Ile Ser Ala Lys Lys Ile Glu Gly
        275                 280                 285

Glu Asn Ile Gly Ala Gln Val Leu Gly Leu Phe Thr Leu Ser Ser Gly
    290                 295                 300

Lys Asp Ile Trp Gln Lys Leu Ser
305                 310
```

<210> SEQ ID NO 43
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 43

```
Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Leu Ala Asn Gln
        35                  40                  45

Gly Trp Tyr Asp Ile Thr Lys Ala Phe Asp Gly Lys Asp Asn Leu Leu
    50                  55                  60
```

-continued

```
Cys Gly Ala Ala Thr Ala Gly Asn Met Leu His Trp Trp Phe Asp Gln
65                  70                  75                  80

Asn Lys Thr Glu Ile Glu Ala Tyr Leu Ser Lys His Pro Glu Lys Gln
                85                  90                  95

Lys Ile Ile Phe Arg Asn Gln Glu Leu Phe Asp Leu Lys Glu Ala Ile
            100                 105                 110

Arg Thr Lys Asp Ser Gln Thr Asn Ser Gln Leu Phe Glu Tyr Phe Arg
        115                 120                 125

Asp Lys Ala Phe Pro Tyr Leu Ser Ala Arg Gln Leu Gly Val Met Pro
    130                 135                 140

Asp Leu Val Leu Asp Met Phe Ile Asn Gly Tyr Tyr Leu Asn Val Phe
145                 150                 155                 160

Lys Thr Gln Ser Thr Asp Val Lys Arg Pro Tyr Gln Asp Lys Asp Lys
                165                 170                 175

Arg Gly Gly Ile Phe Asp Ala Val Phe Thr Arg Gly Asn Gln Thr Thr
            180                 185                 190

Leu Leu Thr Ala Arg His Asp Leu Lys Asn Lys Gly Leu Asn Asp Ile
        195                 200                 205

Ser Thr Ile Ile Lys Glu Glu Leu Thr Lys Gly Arg Ala Leu Ala Leu
    210                 215                 220

Ser His Thr Tyr Ala Asn Val Ser Ile Ser His Val Ile Asn Leu Trp
225                 230                 235                 240

Gly Ala Asp Phe Asn Ala Glu Gly Asn Leu Glu Ala Ile Tyr Val Thr
                245                 250                 255

Asp Ser Asp Ala Asn Ala Ser Ile Gly Met Lys Lys Tyr Phe Val Gly
            260                 265                 270

Ile Asn Lys His Gly His Val Ala Ile Ser Ala Lys Lys Ile Glu Gly
        275                 280                 285

Glu Asn Ile Gly Ala Gln Val Leu Gly Leu Phe Thr Leu Ser Ser Gly
    290                 295                 300

Lys Asp Ile Trp Gln Lys Leu Asn
305                 310
```

<210> SEQ ID NO 44
<211> LENGTH: 292
<212> TYPE: PRT
<213> ORGANISM: Artificial Sequence
<220> FEATURE:
<223> OTHER INFORMATION: IgG degrading enzyme amino acid sequence

<400> SEQUENCE: 44

```
Ser Val Trp Thr Lys Gly Val Thr Pro Pro Glu Gln Phe Thr Gln Gly
1               5                   10                  15

Glu Asp Val Ile His Ala Pro Tyr Leu Ala His Gln Gly Trp Tyr Asp
            20                  25                  30

Ile Thr Lys Ala Phe Asp Gly Lys Asp Asn Leu Leu Cys Gly Ala Ala
        35                  40                  45

Thr Ala Gly Asn Met Leu His Trp Trp Phe Asp Gln Asn Lys Thr Glu
    50                  55                  60

Ile Glu Ala Tyr Leu Ser Lys His Pro Glu Lys Gln Lys Ile Ile Phe
65                  70                  75                  80

Arg Asn Gln Glu Leu Phe Asp Leu Lys Ala Ala Ile Asp Thr Lys Asp
                85                  90                  95

Ser Gln Thr Asn Ser Gln Leu Phe Asn Tyr Phe Arg Asp Lys Ala Phe
            100                 105                 110
```

Pro Asn Leu Ser Ala Arg Gln Leu Gly Val Met Pro Asp Leu Val Leu
115 120 125

Asp Met Phe Ile Asn Gly Tyr Tyr Leu Asn Val Phe Lys Thr Gln Ser
130 135 140

Thr Asp Val Asn Arg Pro Tyr Gln Asp Lys Asp Lys Arg Gly Gly Ile
145 150 155 160

Phe Asp Ala Val Phe Thr Arg Gly Asn Gln Thr Thr Leu Leu Thr Ala
165 170 175

Arg His Asp Leu Lys Asn Lys Gly Leu Asn Asp Ile Ser Thr Ile Ile
180 185 190

Lys Gln Glu Leu Thr Glu Gly Arg Ala Leu Ala Leu Ser His Thr Tyr
195 200 205

Ala Asn Val Ser Ile Ser His Val Ile Asn Leu Trp Gly Ala Asp Phe
210 215 220

Asn Ala Glu Gly Asn Leu Glu Ala Thr Tyr Val Thr Asp Ser Asp Ala
225 230 235 240

Asn Ala Ser Ile Gly Met Lys Lys Tyr Phe Val Gly Ile Asn Ala His
245 250 255

Gly His Val Ala Ile Ser Ala Lys Lys Ile Glu Gly Glu Asn Ile Gly
260 265 270

Ala Gln Val Leu Gly Leu Phe Thr Leu Ser Ser Gly Lys Asp Ile Trp
275 280 285

Gln Lys Leu Ser
290

<210> SEQ ID NO 45
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 45

Asp Asp Tyr Gln Arg Asn Ala Thr Glu Ala Tyr Ala Lys Glu Val Pro
1 5 10 15

His Gln Ile Thr Ser Val Trp Thr Lys Gly Val Thr Pro Pro Glu Gln
20 25 30

Phe Thr Gln Gly Glu Asp Val Ile His Ala Pro Tyr Leu Ala His Gln
35 40 45

Gly Trp Tyr Asp Ile Thr Lys Ala Phe Asp Gly Ala Asp Asn Leu Leu
50 55 60

Cys Gly Ala Ala Thr Ala Gly Asn Met Leu His Trp Trp Phe Asp Gln
65 70 75 80

Asn Lys Thr Glu Ile Glu Ala Tyr Leu Ser Lys His Pro Glu Lys Gln
85 90 95

Lys Ile Ile Phe Arg Asn Gln Glu Leu Phe Asp Leu Lys Ala Ala Ile
100 105 110

Asp Thr Lys Asp Ser Gln Thr Asn Ser Gln Leu Phe Asn Tyr Phe Arg
115 120 125

Asp Lys Ala Phe Pro Asn Leu Ser Ala Arg Gln Leu Gly Val Met Pro
130 135 140

Asp Leu Val Leu Asp Met Phe Ile Asn Gly Tyr Tyr Leu Asn Val Phe
145 150 155 160

Lys Thr Gln Ser Thr Asp Val Asn Arg Pro Tyr Gln Asp Lys Asp Lys
165 170 175

Arg Gly Gly Ile Phe Asp Ala Val Phe Thr Arg Gly Asn Gln Thr Thr
180 185 190

Leu Leu Thr Ala Arg His Asp Leu Lys Asn Lys Gly Leu Asn Asp Ile
195 200 205

Ser Thr Ile Ile Lys Gln Glu Leu Thr Glu Gly Arg Ala Leu Ala Leu
210 215 220

Ser His Thr Tyr Ala Asn Val Ser Ile Ser His Val Ile Asn Leu Trp
225 230 235 240

Gly Ala Asp Phe Asn Ala Glu Gly Asn Leu Glu Ala Thr Tyr Val Thr
245 250 255

Asp Ser Asp Ala Asn Ala Ser Ile Gly Met Lys Lys Tyr Phe Val Gly
260 265 270

Ile Asn Ala His Gly His Val Ala Ile Ser Ala Lys Lys Ile Glu Gly
275 280 285

Glu Asn Ile Gly Ala Gln Val Leu Gly Leu Phe Thr Leu Ser Ser Gly
290 295 300

Lys Asp Ile Trp Gln Lys Leu Ser
305 310

<210> SEQ ID NO 46
<211> LENGTH: 292
<212> TYPE: PRT
<213> ORGANISM: Artificial Sequence
<220> FEATURE:
<223> OTHER INFORMATION: IgG degrading enzyme amino acid sequence

<400> SEQUENCE: 46

Ser Val Trp Thr Lys Gly Val Thr Pro Pro Glu Gln Phe Thr Gln Gly
1 5 10 15

Glu Asp Val Ile His Ala Pro Tyr Leu Ala His Gln Gly Trp Tyr Asp
20 25 30

Ile Thr Lys Ala Phe Asp Gly Ala Asp Asn Leu Leu Cys Gly Ala Ala
35 40 45

Thr Ala Gly Asn Met Leu His Trp Trp Phe Asp Gln Asn Lys Thr Glu
50 55 60

Ile Glu Ala Tyr Leu Ser Lys His Pro Glu Lys Gln Lys Ile Ile Phe
65 70 75 80

Arg Asn Gln Glu Leu Phe Asp Leu Lys Ala Ala Ile Asp Thr Lys Asp
85 90 95

Ser Gln Thr Asn Ser Gln Leu Phe Asn Tyr Phe Arg Asp Lys Ala Phe
100 105 110

Pro Asn Leu Ser Ala Arg Gln Leu Gly Val Met Pro Asp Leu Val Leu
115 120 125

Asp Met Phe Ile Asn Gly Tyr Tyr Leu Asn Val Phe Lys Thr Gln Ser
130 135 140

Thr Asp Val Asn Arg Pro Tyr Gln Asp Lys Asp Lys Arg Gly Gly Ile
145 150 155 160

Phe Asp Ala Val Phe Thr Arg Gly Asn Gln Thr Thr Leu Leu Thr Ala
165 170 175

Arg His Asp Leu Lys Asn Lys Gly Leu Asn Asp Ile Ser Thr Ile Ile
180 185 190

Lys Gln Glu Leu Thr Glu Gly Arg Ala Leu Ala Leu Ser His Thr Tyr
195 200 205

Ala Asn Val Ser Ile Ser His Val Ile Asn Leu Trp Gly Ala Asp Phe
210 215 220

Asn Ala Glu Gly Asn Leu Glu Ala Thr Tyr Val Thr Asp Ser Asp Ala
225 230 235 240

Asn Ala Ser Ile Gly Met Lys Lys Tyr Phe Val Gly Ile Asn Ala His
245 250 255

Gly His Val Ala Ile Ser Ala Lys Lys Ile Glu Gly Glu Asn Ile Gly
260 265 270

Ala Gln Val Leu Gly Leu Phe Thr Leu Ser Ser Gly Lys Asp Ile Trp
275 280 285

Gln Lys Leu Ser
290

<210> SEQ ID NO 47
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 47

Asp Asp Tyr Gln Arg Asn Ala Thr Glu Ala Tyr Ala Lys Glu Val Pro
1 5 10 15

His Gln Ile Thr Ser Val Trp Thr Lys Gly Val Thr Pro Pro Glu Gln
20 25 30

Phe Thr Gln Gly Glu Asp Val Ile His Ala Pro Tyr Leu Ala His Gln
35 40 45

Gly Trp Tyr Asp Ile Thr Lys Ala Phe Asp Gly Lys Asp Asn Leu Leu
50 55 60

Cys Gly Ala Ala Thr Ala Gly Asn Met Leu His Trp Trp Phe Asp Gln
65 70 75 80

Asn Lys Thr Glu Ile Glu Ala Tyr Leu Ser Lys His Pro Glu Lys Gln
85 90 95

Lys Ile Ile Phe Arg Asn Gln Glu Leu Phe Asp Leu Lys Ala Ala Ile
100 105 110

Asp Thr Lys Asp Ser Gln Thr Asn Ser Gln Leu Phe Asn Tyr Phe Arg
115 120 125

Asp Lys Ala Phe Pro Asn Leu Ser Ala Arg Gln Leu Gly Val Met Pro
130 135 140

Asp Leu Val Leu Asp Met Phe Ile Asn Gly Tyr Tyr Leu Asn Val Phe
145 150 155 160

Lys Thr Gln Ser Thr Asp Val Asn Arg Pro Tyr Gln Asp Lys Asp Lys
165 170 175

Arg Gly Gly Ile Phe Asp Ala Val Phe Thr Arg Gly Asn Gln Thr Thr
180 185 190

Leu Leu Thr Ala Arg His Asp Leu Lys Asn Lys Gly Leu Asn Asp Ile
195 200 205

Ser Thr Ile Ile Lys Gln Glu Leu Thr Glu Gly Arg Ala Leu Ala Leu
210 215 220

Ser His Thr Tyr Ala Asn Val Ser Ile Ser His Val Ile Asn Leu Trp
225 230 235 240

Gly Ala Asp Phe Asn Ala Glu Gly Asn Leu Glu Ala Thr Tyr Val Thr
245 250 255

Asp Ser Asp Ala Asn Ala Ser Ile Gly Met Lys Lys Tyr Phe Val Gly
260 265 270

Ile Asn Ala His Gly His Val Ala Ile Ser Ala Lys Lys Ile Glu Gly
275 280 285

Glu Asn Ile Gly Ala Gln Val Leu Gly Leu Phe Thr Leu Ser Ser Gly
290 295 300

Lys Asp Ile Trp Gln Lys Leu Ser
305 310

<210> SEQ ID NO 48
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 48

Asp Asp Tyr Gln Arg Asn Ala Thr Glu Ala Tyr Ala Lys Glu Val Pro
1 5 10 15

His Gln Ile Thr Ser Val Trp Thr Lys Gly Val Thr Pro Leu Thr Pro
20 25 30

Glu Gln Phe Thr Gln Gly Glu Asp Val Phe His Ala Pro Tyr Val Ala
35 40 45

Asn Gln Gly Trp Tyr Asp Ile Thr Lys Ala Phe Asp Gly Lys Asp Asn
50 55 60

Leu Leu Cys Gly Ala Ala Thr Ala Gly Asn Met Leu His Trp Trp Phe
65 70 75 80

Asp Gln Asn Lys Asp Gln Ile Lys Arg Tyr Leu Glu Glu His Pro Glu
85 90 95

Lys Gln Lys Ile Asn Phe Asn Gly Glu Asn Met Phe Asp Val Lys Lys
100 105 110

Ala Ile Asp Thr Lys Asn His Gln Leu Asp Ser Lys Leu Phe Asn Tyr
115 120 125

Phe Lys Glu Lys Ala Phe Pro Tyr Leu Ser Ala Lys His Leu Gly Val
130 135 140

Phe Pro Asp His Val Ile Asp Met Phe Ile Asn Gly Tyr Arg Leu Ser
145 150 155 160

Leu Thr Asn His Gly Pro Thr Pro Val Lys Glu Gly Ser Lys Asp Pro
165 170 175

Arg Gly Gly Ile Phe Asp Ala Val Phe Thr Arg Gly Asn Gln Ser Lys
180 185 190

Leu Leu Thr Ser Arg His Asp Phe Lys Asn Lys Asn Leu Asn Asp Ile
195 200 205

Ser Thr Ile Ile Lys Gln Glu Leu Thr Lys Gly Lys Ala Leu Gly Leu
210 215 220

Ser His Thr Tyr Ala Asn Val Arg Ile Asn His Val Ile Asn Leu Trp
225 230 235 240

Gly Ala Asp Phe Asn Ala Glu Gly Asn Leu Glu Ala Thr Tyr Val Thr
245 250 255

Asp Ser Asp Ser Asn Ala Ser Ile Gly Met Lys Lys Tyr Phe Val Gly
260 265 270

Val Asn Ala His Gly His Val Ala Ile Ser Ala Lys Lys Ile Glu Gly
275 280 285

Glu Asn Ile Gly Ala Gln Val Leu Gly Leu Phe Thr Leu Ser Thr Gly
290 295 300

Gln Asp Ser Trp Gln Lys Leu Ser
305 310

<210> SEQ ID NO 49
<211> LENGTH: 312

```
<212> TYPE: PRT
<213> ORGANISM: Artificial Sequence
<220> FEATURE:
<223> OTHER INFORMATION: IgG degrading enzyme amino acid sequence

<400> SEQUENCE: 49

Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Leu Thr Pro
            20                  25                  30

Glu Gln Phe Thr Gln Gly Glu Asp Val Phe His Ala Pro Tyr Val Ala
        35                  40                  45

Asn Gln Gly Trp Tyr Asp Ile Thr Lys Ala Phe Asp Gly Lys Asp Asn
    50                  55                  60

Leu Leu Cys Gly Ala Ala Thr Ala Gly Asn Met Leu His Trp Trp Phe
65                  70                  75                  80

Asp Gln Asn Lys Asp Gln Ile Lys Arg Tyr Leu Glu Glu His Pro Glu
                85                  90                  95

Lys Gln Lys Ile Asn Phe Arg Gly Glu Asn Met Phe Asp Val Lys Glu
            100                 105                 110

Ala Ile Arg Thr Lys Asn His Gln Leu Asp Ser Lys Leu Phe Glu Tyr
        115                 120                 125

Phe Lys Glu Lys Ala Phe Pro Tyr Leu Ser Ala Lys His Leu Gly Val
    130                 135                 140

Phe Pro Asp His Val Ile Asp Met Phe Ile Asn Gly Tyr Arg Leu Ser
145                 150                 155                 160

Leu Thr Asn His Gly Pro Thr Pro Val Lys Lys Gly Ser Lys Asp Pro
                165                 170                 175

Arg Gly Gly Ile Phe Asp Ala Val Phe Thr Arg Gly Asn Gln Ser Lys
            180                 185                 190

Leu Leu Thr Ser Arg His Asp Phe Lys Asn Lys Asn Leu Asn Asp Ile
        195                 200                 205

Ser Thr Ile Ile Lys Ser Glu Leu Thr Asn Gly Lys Ala Leu Gly Leu
    210                 215                 220

Ser His Thr Tyr Ala Asn Val Arg Ile Asn His Val Ile Asn Leu Trp
225                 230                 235                 240

Gly Ala Asp Phe Asn Ala Glu Gly Asn Leu Glu Ala Thr Tyr Val Thr
                245                 250                 255

Asp Ser Asp Ser Asn Ala Ser Ile Gly Met Lys Lys Tyr Phe Val Gly
            260                 265                 270

Val Asn Lys His Gly His Val Ala Ile Ser Ala Lys Lys Ile Glu Gly
        275                 280                 285

Glu Asn Ile Gly Ala Gln Val Leu Gly Leu Phe Thr Leu Ser Thr Gly
    290                 295                 300

Gln Asp Ser Trp Gln Lys Leu Asn
305                 310


<210> SEQ ID NO 50
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 50

Asp Asp Tyr Gln Arg Asn Ala Thr Glu Ala Tyr Ala Lys Glu Val Pro
1               5                   10                  15
```

His Gln Ile Thr Ser Val Trp Thr Lys Gly Val Thr Pro Leu Thr Pro
20 25 30

Glu Gln Phe Thr Gln Gly Glu Asp Val Phe His Ala Pro Tyr Val Ala
35 40 45

Asn Gln Gly Trp Tyr Asp Ile Thr Lys Thr Phe Asn Gly Lys Asp Asp
50 55 60

Leu Leu Cys Gly Ala Ala Thr Ala Gly Asn Met Leu His Trp Trp Phe
65 70 75 80

Asp Gln Asn Lys Asp Gln Ile Lys Arg Tyr Leu Glu Glu His Pro Glu
85 90 95

Lys Gln Lys Ile Asn Phe Asn Gly Glu Gln Met Phe Asp Val Lys Glu
100 105 110

Ala Ile Asp Thr Lys Asn His Gln Leu Asp Ser Lys Leu Phe Glu Tyr
115 120 125

Phe Lys Glu Lys Ala Phe Pro Tyr Leu Ser Thr Lys His Leu Gly Val
130 135 140

Phe Pro Asp His Val Ile Asp Met Phe Ile Asn Gly Tyr Arg Leu Ser
145 150 155 160

Leu Thr Asn His Gly Pro Thr Pro Val Lys Glu Gly Ser Lys Asp Pro
165 170 175

Arg Gly Gly Ile Phe Asp Ala Val Phe Thr Arg Gly Asn Gln Ser Lys
180 185 190

Leu Leu Thr Ser Arg His Asp Phe Lys Glu Lys Asn Leu Lys Glu Ile
195 200 205

Ser Asp Leu Ile Lys Gln Glu Leu Thr Glu Gly Lys Ala Leu Gly Leu
210 215 220

Ser His Thr Tyr Ala Asn Val Arg Ile Asn His Val Ile Asn Leu Trp
225 230 235 240

Gly Ala Asp Phe Asp Ala Glu Gly Asn Leu Lys Ala Ile Tyr Val Thr
245 250 255

Asp Ser Asp Ser Asn Ala Ser Ile Gly Met Lys Lys Tyr Phe Val Gly
260 265 270

Val Asn Ala Ala Gly Lys Val Ala Ile Ser Ala Lys Lys Ile Glu Gly
275 280 285

Glu Asn Ile Gly Ala Gln Val Leu Gly Leu Phe Thr Leu Ser Thr Gly
290 295 300

Gln Asp Ser Trp Asn Gln Thr Ser
305 310

<210> SEQ ID NO 51
<211> LENGTH: 312
<212> TYPE: PRT
<213> ORGANISM: Artificial Sequence
<220> FEATURE:
<223> OTHER INFORMATION: IgG degrading enzyme amino acid sequence

<400> SEQUENCE: 51

Asp Asp Tyr Gln Arg Asn Ala Thr Glu Ala Tyr Ala Lys Glu Val Pro
1 5 10 15

His Gln Ile Thr Ser Val Trp Thr Lys Gly Val Thr Pro Leu Thr Pro
20 25 30

Glu Gln Phe Thr Gln Gly Glu Asp Val Phe His Ala Pro Tyr Val Ala
35 40 45

Asn Gln Gly Trp Tyr Asp Ile Thr Lys Thr Phe Asn Gly Lys Asp Asp
50 55 60

```
Leu Leu Cys Gly Ala Ala Thr Ala Gly Asn Met Leu His Trp Trp Phe
65                  70                  75                  80

Asp Gln Asn Lys Asp Gln Ile Lys Arg Tyr Leu Glu Glu His Pro Glu
                85                  90                  95

Lys Gln Lys Ile Asn Phe Arg Gly Glu Gln Met Phe Asp Val Lys Glu
            100                 105                 110

Ala Ile Arg Thr Lys Asn His Gln Leu Asp Ser Lys Leu Phe Glu Tyr
        115                 120                 125

Phe Lys Glu Lys Ala Phe Pro Tyr Leu Ser Thr Lys His Leu Gly Val
    130                 135                 140

Phe Pro Asp His Val Ile Asp Met Phe Ile Asn Gly Tyr Arg Leu Ser
145                 150                 155                 160

Leu Thr Asn His Gly Pro Thr Pro Val Lys Lys Gly Ser Lys Asp Pro
                165                 170                 175

Arg Gly Gly Ile Phe Asp Ala Val Phe Thr Arg Gly Asn Gln Ser Lys
            180                 185                 190

Leu Leu Thr Ser Arg His Asp Phe Lys Glu Lys Asn Leu Lys Glu Ile
        195                 200                 205

Ser Asp Leu Ile Lys Glu Glu Leu Thr Lys Gly Lys Ala Leu Gly Leu
    210                 215                 220

Ser His Thr Tyr Ala Asn Val Arg Ile Asn His Val Ile Asn Leu Trp
225                 230                 235                 240

Gly Ala Asp Phe Asp Ala Glu Gly Asn Leu Lys Ala Ile Tyr Val Thr
                245                 250                 255

Asp Ser Asp Ser Asn Ala Ser Ile Gly Met Lys Lys Tyr Phe Val Gly
            260                 265                 270

Val Asn Lys Ala Gly Lys Val Ala Ile Ser Ala Lys Lys Ile Glu Gly
        275                 280                 285

Glu Asn Ile Gly Ala Gln Val Leu Gly Leu Phe Thr Leu Ser Thr Gly
    290                 295                 300

Gln Asp Ser Trp Asn Gln Thr Asn
305                 310
```

<210> SEQ ID NO 52
<211> LENGTH: 310
<212> TYPE: PRT
<213> ORGANISM: Artificial Sequence
<220> FEATURE:
<223> OTHER INFORMATION: IgG degrading enzyme amino acid sequence

<400> SEQUENCE: 52

```
Asp Asp Tyr Gln Arg Asn Ala Thr Glu Ala Tyr Ala Lys Glu Val Pro
1               5                   10                  15

His Gln Ile Thr Ser Val Trp Thr Lys Gly Val Thr Pro Pro Glu Gln
            20                  25                  30

Phe Thr Gln Gly Glu Asp Val Ile His Ala Pro Tyr Val Ala Asn Gln
        35                  40                  45

Gly Trp Tyr Asp Ile Thr Lys Ala Phe Asp Gly Lys Asp Asn Leu Leu
    50                  55                  60

Cys Gly Ala Ala Thr Ala Gly Asn Met Leu His Trp Trp Phe Asp Gln
65                  70                  75                  80

Asn Lys Asp Gln Ile Lys Arg Tyr Leu Glu Glu His Pro Glu Lys Gln
                85                  90                  95

Lys Ile Asn Phe Arg Gly Glu Gln Met Phe Asp Val Lys Lys Ala Ile
            100                 105                 110
```

-continued

```
Asp Thr Lys Asn His Gln Leu Asp Ser Lys Leu Phe Asn Tyr Phe Lys
        115                 120                 125

Glu Lys Ala Phe Pro Gly Leu Ser Ala Arg Arg Ile Gly Val Phe Pro
    130                 135                 140

Asp His Val Ile Asp Met Phe Ile Asn Gly Tyr Arg Leu Ser Leu Thr
145                 150                 155                 160

Asn His Gly Pro Thr Pro Val Lys Glu Gly Ser Lys Asp Pro Arg Gly
                165                 170                 175

Gly Ile Phe Asp Ala Val Phe Thr Arg Gly Asn Gln Ser Lys Leu Leu
            180                 185                 190

Thr Ser Arg His Asp Phe Lys Asn Lys Asn Leu Asn Asp Ile Ser Thr
        195                 200                 205

Ile Ile Lys Gln Glu Leu Thr Lys Gly Lys Ala Leu Gly Leu Ser His
    210                 215                 220

Thr Tyr Ala Asn Val Ser Ile Asn His Val Ile Asn Leu Trp Gly Ala
225                 230                 235                 240

Asp Phe Asn Ala Glu Gly Asn Leu Glu Ala Thr Tyr Val Thr Asp Ser
                245                 250                 255

Asp Ser Asn Ala Ser Ile Gly Met Lys Lys Tyr Phe Val Gly Val Asn
            260                 265                 270

Ala His Gly His Val Ala Ile Ser Ala Lys Lys Ile Glu Gly Glu Asn
        275                 280                 285

Ile Gly Ala Gln Val Leu Gly Leu Phe Thr Leu Ser Thr Gly Gln Asp
    290                 295                 300

Ser Trp Gln Lys Leu Ser
305                 310
```